US012687544B2

(12) United States Patent　　(10) Patent No.:　US 12,687,544 B2
Iida et al.　　　　　　　　　　　(45) Date of Patent:　　Jul. 21, 2026

(54) METHOD FOR DETECTING ANALYTE AND SYSTEM FOR DETECTING ANALYTE

(71) Applicant: University Public Corporation Osaka, Osaka (JP)

(72) Inventors: Takuya Iida, Sakai (JP); Shiho Tokonami, Sakai (JP); Ikuhiko Nakase, Sakai (JP)

(73) Assignee: University Public Corporation Osaka, Osaka (JP)

( * ) Notice: Subject to any disclaimer, the term of this patent is extended or adjusted under 35 U.S.C. 154(b) by 1002 days.

(21) Appl. No.: 17/639,087

(22) PCT Filed: Aug. 28, 2020

(86) PCT No.: PCT/JP2020/032758
§ 371 (c)(1),
(2) Date: Feb. 28, 2022

(87) PCT Pub. No.: WO2021/040021
PCT Pub. Date: Mar. 4, 2021

(65) Prior Publication Data
US 2022/0326249 A1　　Oct. 13, 2022

(30) Foreign Application Priority Data
Aug. 30, 2019　　(JP) ................................. 2019-158131

(51) Int. Cl.
*G01N 33/68*　　　(2006.01)
*B01L 3/00*　　　(2006.01)
(Continued)

(52) U.S. Cl.
CPC .... *G01N 33/6803* (2013.01); *B01L 3/502715* (2013.01); *G01N 21/6428* (2013.01);
(Continued)

(58) Field of Classification Search
None
See application file for complete search history.

(56) References Cited

U.S. PATENT DOCUMENTS 4,893,886 A * 1/1990 Ashkin ................. G01N 15/10
359/350
5,198,369 A 3/1993 Itoh et al.
(Continued)

FOREIGN PATENT DOCUMENTS

EP　　　0455125 A2　11/1991
EP　　　0556748 A2　8/1993
(Continued)

OTHER PUBLICATIONS

Mayu Ueda, Microflow-mediated optical assembly of nanoparticles with femtogram protein via shrinkage of light-induced bubbles Scilightfeatured, APL Photonics, Jan. 2019, vol. 4 No. 1, pp. 010802-1-010802-6, https://doi.org/10.1063/1.5079306.
(Continued)

*Primary Examiner* — Henry H Nguyen
(74) *Attorney, Agent, or Firm* — MARSHALL, GERSTEIN & BORUN LLP

(57)　　　　　　ABSTRACT

A method for detecting an analyte includes first to third steps. The first step is distributing a sample containing a bead modified with a host molecule that is specifically bound to the analyte in a microchannel using a syringe pump. The second step is irradiating the sample with non-resonant light that is light outside a wavelength range of electronic resonance of the bead. The third step is detecting the analyte based on a signal from a camera that receives the light from the sample.

9 Claims, 52 Drawing Sheets

(51) Int. Cl.
　　*G01N 21/64* 　　　(2006.01)
　　*G01N 33/58* 　　　(2006.01)

(52) U.S. Cl.
　　CPC .... *G01N 33/582* (2013.01); *B01L 2300/0654*
　　(2013.01); *B01L 2400/0478* (2013.01); *G01N*
　　*2021/6439* (2013.01)

(56) References Cited

U.S. PATENT DOCUMENTS

| | | | | |
|---|---|---|---|---|
| 6,934,022 B1* | 8/2005 | Engelhardt | .......... | G01N 21/554 |
| | | | | 356/336 |
| 7,515,269 B1* | 4/2009 | Alexander | ........... | G01N 21/658 |
| | | | | 356/445 |
| 10,876,946 B2* | 12/2020 | Ndukaife | .............. | G21K 1/006 |
| 2002/0064866 A1 | 5/2002 | Tajima et al. | | |
| 2003/0096302 A1* | 5/2003 | Yguerabide | ........... | G01N 21/47 |
| | | | | 435/7.1 |
| 2004/0067502 A1* | 4/2004 | Guenther | ............. | C12Q 1/6816 |
| | | | | 435/7.1 |
| 2006/0257992 A1* | 11/2006 | McDevitt | ................ | B01L 9/527 |
| | | | | 435/287.2 |
| 2007/0196937 A1 | 8/2007 | Itoh et al. | | |
| 2009/0101847 A1* | 4/2009 | Furuki | .............. | G01N 15/1459 |
| | | | | 250/492.1 |
| 2016/0123968 A1 | 5/2016 | Iida et al. | | |
| 2017/0074760 A1 | 3/2017 | Iida et al. | | |
| 2018/0071740 A1* | 3/2018 | Brueckner | ......... | G01N 35/1002 |

FOREIGN PATENT DOCUMENTS

| | | | | | |
|---|---|---|---|---|---|
| EP | 2993460 | A1 | 3/2016 | | |
| JP | H04-006465 | A | 1/1992 | | |
| JP | H0466873 | A | 3/1992 | | |
| JP | H05-296914 | A | 11/1993 | | |
| JP | H09-329602 | A | 12/1997 | | |
| WO | WO-2005/087654 | A1 | 9/2005 | | |
| WO | WO-2014/192937 | A1 | 12/2014 | | |
| WO | WO-2015139028 | A1 * | 9/2015 | ............. | G01N 21/47 |
| WO | WO-2015/170758 | A1 | 11/2015 | | |
| WO | WO-2018/003856 | A1 | 1/2018 | | |
| WO | WO-2018/207937 | A1 | 11/2018 | | |

OTHER PUBLICATIONS

Mayu Ueda, Microflow-mediated optical assembly of nanoparticles with femtogram protein via shrinkage of light-induced bubbles Scilightfeatured, APL Photonics, Jan. 2019, vol. 4 No. 1, pp. 010802-1-010802-6, https://doi.org/10.1063/1.507930.

Office Action, Japanese patent application No. 2021-543081, mailing date Aug. 6, 2024.

International Search Report issued in PCT Patent Application No. PCT/JP2020/032758 dated Nov. 17, 2020.

Suzuku, Y., "Introduction Course "Quantification of Total Protein,"" *Bunseki*, pp. 2-9 (2018.

Shiozaki, T. et al., "Self-assembly of nanoparticles by optical forces on wall surfaces of flow channels," Lecture proceedings of 2018 annual conference of the Japan Society of Mechanical Engineers (2018).

Extended European Search Report for corresponding European Application No. 20859031.5 dated Aug. 11, 2023.

\* cited by examiner

X

<DOWNWARD IRRADIATION>

<UPWARD IRRADIATION>

FIG.10

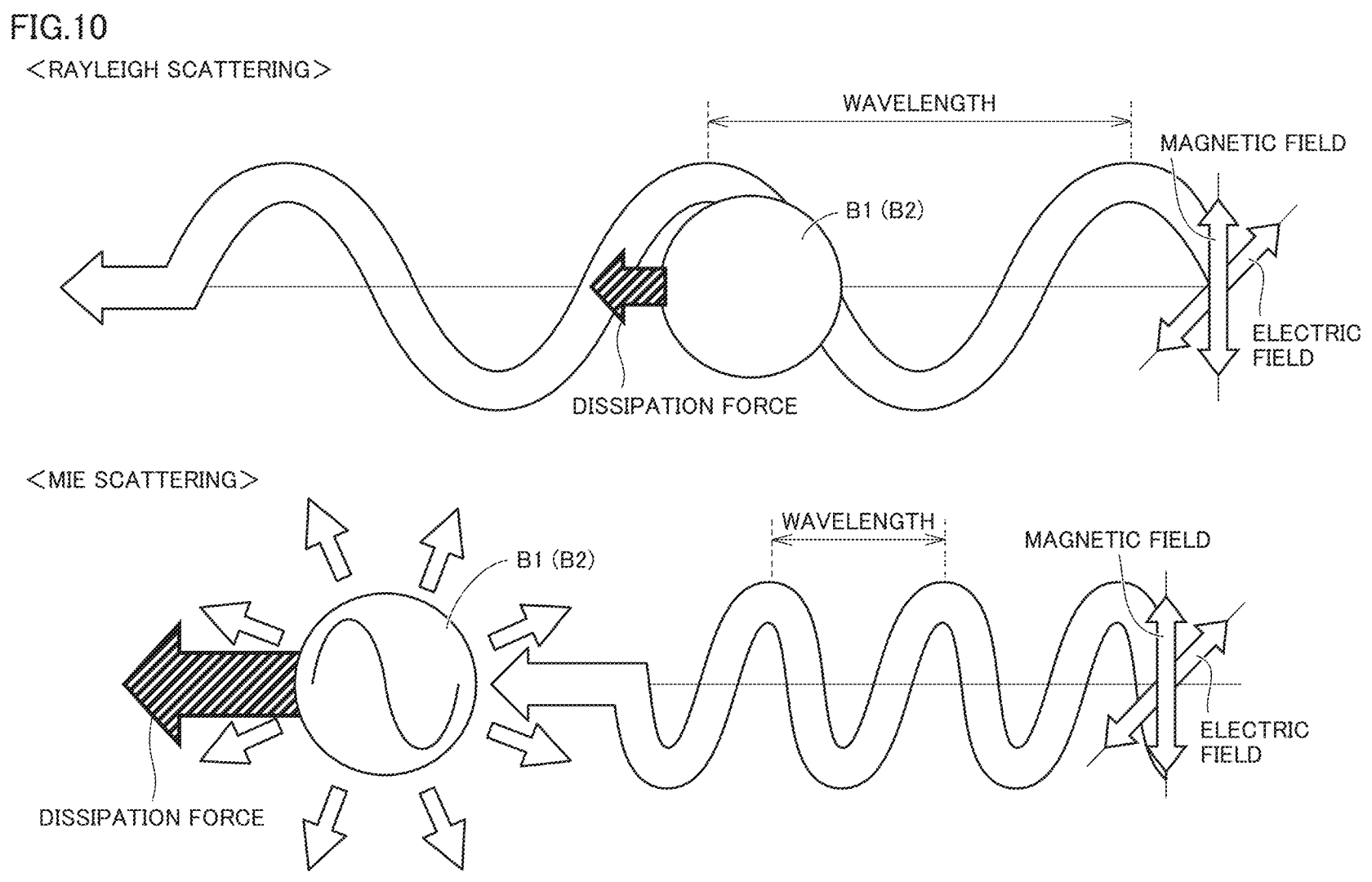

<RAYLEIGH SCATTERING>

MAGNETIC FIELD

ELECTRIC FIELD

WAVELENGTH

B1 (B2)

DISSIPATION FORCE

<MIE SCATTERING>

MAGNETIC FIELD

ELECTRIC FIELD

WAVELENGTH

B1 (B2)

DISSIPATION FORCE

<LOW FLOW SPEED>

<HIGH FLOW SPEED>

<FDP>

FIG.26

<LIGHT IRRADIATION TIME OF FOUR MINUTES>

AGGREGATION AREA A [$\mu$m$^2$]

TARGET CONCENTRATION [$\mu$g/mL]

<LIGHT IRRADIATION TIME OF FOUR MINUTES + WAITING FOR TEN SECONDS>

AGGREGATION AREA A [$\mu$m$^2$]

TARGET CONCENTRATION [$\mu$g/mL]

<DEFOCUS CONDITION>

<DEFOCUS CONDITION>

TARGET CONCENTRATION [pg/mL]

<FIRST MICROCHANNEL>

<SECOND MICROCHANNEL>

<THIRD MICROCHANNEL>

<FIRST MICROCHANNEL>

<SECOND MICROCHANNEL>

<THIRD MICROCHANNEL>

<FIRST MICROCHANNEL>

<SECOND MICROCHANNEL>

<THIRD MICROCHANNEL>

\<SECOND MICROCHANNEL\>

\<THIRD MICROCHANNEL\>

<COMPARATIVE EXAMPLE>

<THIRD MICROCHANNEL>

MULTILAYER RATIO [%]

$y = 0.1201x + 0.168$
$R^2 = 0.9371$

TARGET CONCENTRATION [pg/mL]

<FIRST SYRINGE PUMP> y = 0.1732x + 0.0259
$R^2$ = 0.9469

<SECOND SYRINGE PUMP> y = 0.1376x + 0.0037
$R^2$ = 0.9796

<CD9/CD63 COMPLEX EPITOPE + FLUORESCENT BEAD>

<CD9/CD63 COMPLEX EPITOPE + FLUORESCENT BEAD>

<NON-FLUORESCENT EXOSOME + FLUORESCENT BEAD>

<NON-FLUORESCENT EXOSOME + FLUORESCENT BEAD>

METHOD FOR DETECTING ANALYTE AND SYSTEM FOR DETECTING ANALYTE

TECHNICAL FIELD

The present disclosure relates to a method for detecting an analyte and a system for detecting the analyte.

BACKGROUND ART

Various techniques for detecting an analyte that may be contained in a sample have been put into practical use. Examples of the analyte include an allergen, a protein derived from a cancer cell, a nucleic acid, and a vesicle. For example, an enzyme-linked immuno sorbent assay (ELISA) method and a surface plasmon resonance (SPR) method are known as a protein detection technique. A lowest concentration (detection limit) of the analyte that can be detected by the ELISA method is about 0.3 [ng/mL], and the detection limit of the SPR method is about 1 [μg/mL]. In addition, it takes several hours to detect the analyte by any method.

A technique for detecting the analyte using light has been proposed. For example, a detection device for the analyte disclosed in WO 2014/192937 includes a plurality of metal nanoparticles, a light source, an objective lens, an optical receiver, and a detector. Each of the plurality of metal nanoparticles is modified with a host molecule to which the analyte can be specifically adhered. The light source emits polarized light to gather the plurality of metal nanoparticles. The objective lens collects the polarized light and introduces the collected polarized light into a liquid containing the sample and the plurality of metal nanoparticles. The optical receiver receives the light from the liquid. The detector detects the analyte based on a signal from the optical receiver.

There is always a demand for a technique for increasing the detection sensitivity of the analyte or shortening detection time of the analyte, in other words, a technique capable of rapidly detecting a trace amount of the analyte.

The present disclosure has been made to solve such a problem, and an object of the present disclosure is to quickly detect the analyte with high sensitivity.

SUMMARY OF INVENTION

A method for detecting an analyte according to one aspect of the present disclosure includes first to third steps. The first step is a step of distributing a liquid sample containing a plurality of fine particles each of which is modified with a host molecule that is specifically bound to the analyte in a microchannel using a pump. The second step is a step of irradiating the liquid sample with non-resonant light that is light outside a wavelength range of electronic resonance of the plurality of fine particles. The third step is a step of detecting the analyte based on a signal from an optical receiver that receives light (transmitted light, reflected light or scattered light) from the liquid sample.

The optical receiver includes a camera that captures the liquid sample. The detecting step (third step) includes: a step of calculating an index representing a size of an aggregate formed by aggregation of the analyte and the plurality of fine particles based on an image obtained by capturing the liquid sample with the camera; and a step of calculating a concentration of the analyte contained in the liquid sample from the calculated index by referring to a correspondence relationship obtained previously between the concentration of the analyte and the index.

The method for detecting the analyte further includes a step of stopping the irradiation with the non-resonant light after the irradiating step (first step). The detecting step (third step) includes a step of detecting the analyte based on a signal acquired from the optical receiver after standby for a predetermined period since the irradiation with the non-resonant light is stopped.

The detecting step (third step) includes determining whether the analyte is contained in the liquid sample, based on a change in intensity of a signal acquired from the optical receiver while the irradiation with the non-resonant light is continued.

Specific gravity of each of the plurality of fine particles is larger than specific gravity of a dispersion medium of the plurality of fine particles. The irradiating step (second step) includes a step of irradiating the liquid sample with the non-resonant light from above to below of the liquid sample.

The irradiating step (second step) includes a step of irradiating the liquid sample with the non-resonant light under a condition that a focal point of the non-resonant light is located behind the microchannel in an irradiation direction of the non-resonant light.

The irradiating step (second step) includes a step of irradiating the liquid sample with the non-resonant light while a region that is not irradiated with the non-resonant light remains locally.

The method for detecting the analyte further includes a step of adjusting a flow velocity of the liquid sample to a flow velocity at which the analyte and the plurality of fine particles can be prevented from splitting after aggregation prior to the distributing step (first step).

At least one of the analyte and the plurality of fine particles has a surface modified with a fluorescent molecule or has a fluorescent molecule doped (or expressed) in the analyte and the plurality of fine particles.

A combination of diameters of the plurality of fine particles and the wavelength range of the non-resonant light is determined such that the non-resonant light causes Mie scattering when the plurality of fine particles are irradiated with the non-resonant light.

A system for detecting an analyte according to another aspect of the present disclosure includes a holder, a pump, a light source, an optical receiver, and an arithmetic device. The holder is configured to hold a detection kit in which a microchannel is provided. The pump causes a liquid sample containing a plurality of fine particles each of which is modified with a host molecule that specifically binds to an analyte to flow through the microchannel. The light source that irradiates the liquid sample with non-resonant light that is light outside a wavelength range of electronic resonance of the plurality of fine particles. The optical receiver receives light (transmitted light, reflected light or scattered light) from the liquid sample. The arithmetic device executes process of detecting the analyte based on a signal from the optical receiver.

The light source irradiates the liquid sample with light having a wavelength range where Mie scattering is generated by the plurality of fine particles as the non-resonant light.

The optical receiver includes a camera that captures the liquid sample. In the detection process, the arithmetic device calculates an index representing a size of an aggregate formed by aggregation of the analyte and the plurality of fine particles from an image captured by the camera. The arithmetic device calculates a concentration of the analyte contained in the liquid sample from the calculated index by referring to a correspondence relationship obtained previously between the concentration of the analyte and the index.

The system for detecting the analyte further includes a confocal optical system. The confocal optical system irradiates the liquid sample with the non-resonant light from the light source and guides the transmitted light or reflected light from the liquid sample to the optical receiver. The arithmetic device calculates a volume of the aggregate as the index from a three-dimensional image captured by the camera.

According to the present disclosure, the analyte can be quickly detected with high sensitivity.

BRIEF DESCRIPTION OF DRAWINGS

FIG. 10 is a conceptual diagram illustrating a relationship between a size of the latex bead and a wavelength of the laser beam.

FIG. 20 is a view illustrating an image near the laser spot when the analyte is the CD80 and when a 10-power magnifying lens is used.

FIG. 23 is a view illustrating an image near the laser spot in Example 2 where the analyte is an FDP.

FIG. 26 is a view illustrating the relationship between the target concentration and the aggregation area of the latex bead during the upward irradiation when the analyte is the FDP.

FIG. 41 is a view illustrating the calibration curve obtained using the third microchannel.

DESCRIPTION OF EMBODIMENTS

Figure 1:
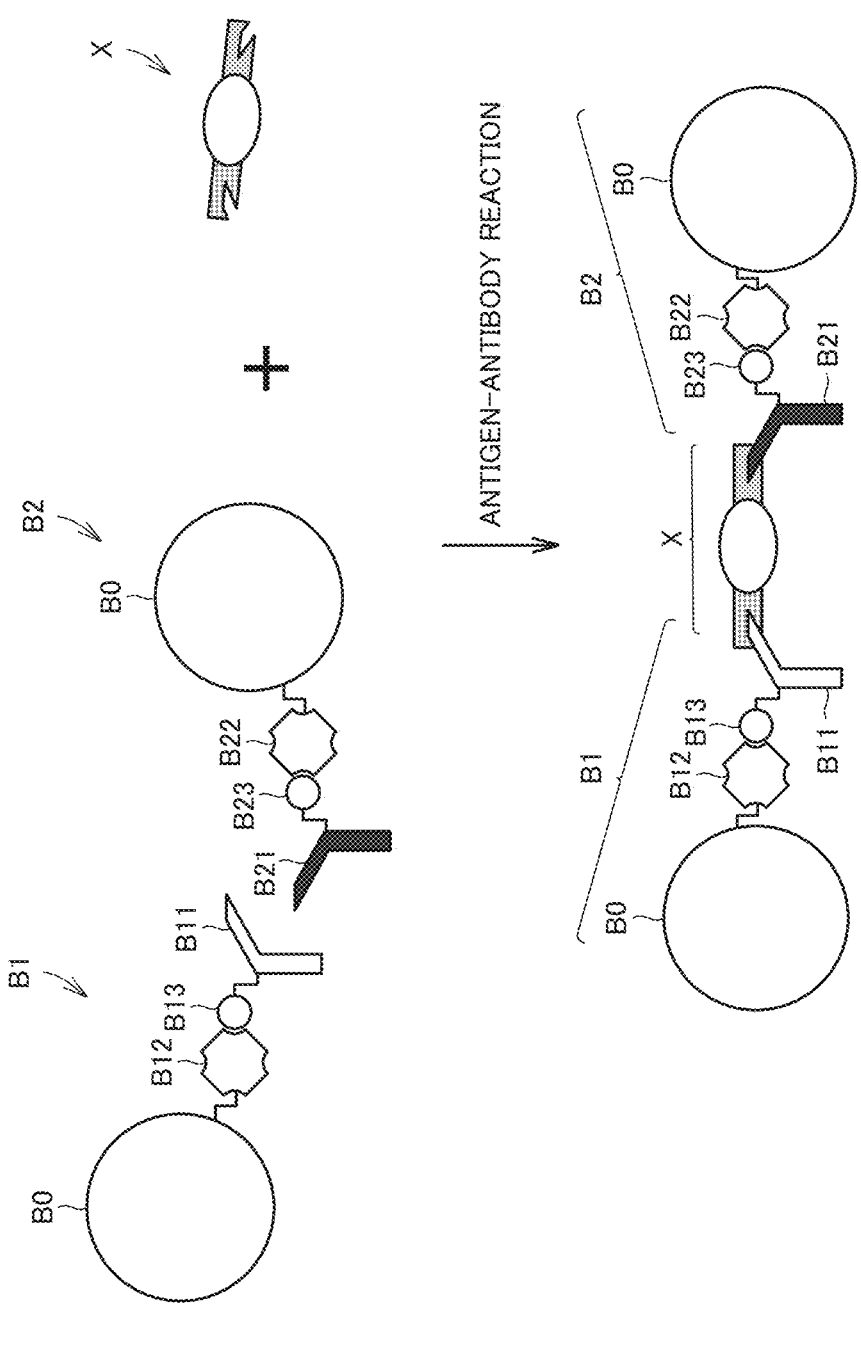
FIG. 1 is a conceptual diagram illustrating a detection principle of a certain analyte.

Hereinafter, embodiments will be described in detail with reference to the drawings. In the drawings, the same or corresponding portion is denoted by the same reference numeral, and the description thereof will not be repeated.
<Description of Terms>

In the present disclosure and the embodiments thereof, the "sample" means a material containing the analyte or a material that may contain the analyte. For example, the sample may be a biological sample from an animal (such as a human, a bovine, an equine, a porcine, a goat, a chicken, a rat, and a mouse). For example, the biological sample may include a blood, a tissue, a cell, a secretion, and a body fluid. The "sample" may include a dilution or a separation thereof (such as a serum and a plasma). The "liquid sample" is a liquid containing the sample.

In the present disclosure and the embodiments thereof, the "analyte" means a material that has a size from nanometer order to micrometer order and is detected using the detection kit. A shape of the analyte is not particularly limited, and is, for example, a spherical shape, an elliptical spherical shape, or a rod shape (pole shape). When the analyte has the elliptical spherical shape, at least one of a length in a minor axis direction and a length in a major axis direction of the elliptical sphere may be within a range from the nanometer order to the micrometer order. When the analyte has the rod shape, at least one of a width and the length of the rod may be in a range from the nanometer order to the micrometer order.

Examples of the analyte include a cell, a microorganism (bacteria, fungi, and the like), a vesicle (an exosomes, a microvesicle, an apoptotic body, and the like), a biopolymer (a protein, a nucleic acid, a lipid, a polysaccharide, and the like), an antigen (an allergen and the like), and a virus. Specific examples of the protein include an antibody classified into a cluster of differentiation (CD) such as CD9, CD63, CD80, and CD81, a cytokine such as IL-6, and an albumin. The nucleic acid includes DNA or RNA. Specifically, the nucleic acid includes free DNA (cell free DNA, cfDNA), blood tumor DNA derived from a cancer cell (circulating tumor DNA, ctDNA), messenger RNA (mRNA), microRNA (miRNA), and the like. However, the analyte is not limited to a material derived from a living body (biological material), but may be a resin bead metal nanoparticle, a metal nanoparticle assembly, a metal nanoparticle integrated structure, a semiconductor nanoparticle, an organic nanoparticle, or the like.

In the present disclosure and the embodiments thereof, the "fine particle" means a material having the size in the nanometer order to the micrometer order. The shape of the fine particles is not limited to a spherical shape, but may be the elliptical spherical shape, the rod shape, or the like. When the fine particle has the elliptical spherical shape, at least one of the length in the major axis direction and the length in the minor axis direction of the elliptical sphere may be within the range from the nanometer order to the micrometer order. When the fine particle has the rod shape, at least one of the width and the length of the rod may be within the range from the nanometer order to the micrometer order.

Examples of the fine particle include a metal nanoparticle, a metal nanoparticle aggregate, a metal nanoparticle integrated structure, a semiconductor nanoparticle, an organic nanoparticle, a resin bead, a magnetic bead, and a particulate matter (PM). The "metal nanoparticle" is a metal particle having the size of the nanometer order. The "metal nanoparticle assembly" is an assembly formed by aggregation of a plurality of metal nanoparticles. For example, the "metal nanoparticle assembly structure" is a structure in which the plurality of metal nanoparticles are fixed to the surface of the bead through an interaction site, and are arranged at intervals less than or equal to the diameter of the metal nanoparticle with gaps therebetween. The "semiconductor nanoparticle" is a semiconductor particle having the size of the nanometer order. The "organic nanoparticle" is a particle made of an organic compound having the size of nanometer order. The "resin bead" is a particle made of the resin having the size from the nanometer order to the micrometer order. The "magnetic bead" is a magnetized particle (polymer fine particle in which a magnetic body is dispersed or embedded) having the size from the nanometer order to the micrometer order. The "PM" is a particulate material having the size of the micrometer order.

In the present disclosure and the embodiments thereof, the "nanometer order" includes a range of 1 nm to 1000 nm (=1 μm). The "micrometer order" includes a range from 1 μm to 1000 μm (=1 mm). Accordingly, "from the nanometer order to the micrometer order" includes the range of 1 nm to 1000 μm. The term "from the nanometer order to the micrometer order" typically means the range from several nanometers to several hundred micrometers, preferably from 100 nm to 100 μm, and more preferably from 1 μm to several tens of micrometers.

In the present disclosure and the embodiments thereof, the "host molecule" means a material capable of being specifically bound to (may be specifically adhered to) the analyte. Examples of the combination of the host molecule and the analyte include an antigen and an antibody, a sugar chain and a protein, a lipid and a protein, a low molecular weight compound (ligand) and a protein, a protein and a protein, and a single-stranded DNA and a single-stranded DNA. When one of the two having specific affinities is an analyte, the other can be used as the host molecule. That is, for example, when the antigen is the analyte, the antibody can be used as the host molecule. Conversely, when the antibody is the analyte, the antigen can be used as the host molecule.

In DNA hybridization, the analyte is target DNA, and the host molecule is probe DNA. An anti-DNA antibody (for example, anti-dsDNA that is specifically bound to double-stranded DNA or anti-ssDNA that is specifically bound to single-stranded DNA) that is specifically bound to DNA can also be used as the host molecule. The antigen may include an allergen, a microorganism (such as a bacterium and a fungus), a virus, and a vesicle. It is also possible to change the types of detectable allergen, microorganism or virus by changing the type of antibody. Accordingly, the type of detectable allergen, microorganism, or virus of the present disclosure is not particularly limited. When the analyte is a heavy metal, a material capable of collecting a heavy metal ion can be used as the host molecule.

The host molecule is fixed to the surface of the fine particle by interaction between the host molecule and the fine particle. The type of the interaction used to fix the host molecule to the fine particle surface is determined according to the type of the fine particle. The interactions include covalent bonding, ionic bonding, metal bonding, van der Waals force, an electrostatic interaction, a hydrophobic interaction, intermolecular force (for example, hydrogen bonding), and adsorption force.

In the present disclosure and the exemplary embodiments thereof, the "microchannel" means a channel in which a section of a channel through which a liquid is distributed is on the micrometer order. For example, when the channel section is rectangular, the length of at least one of the short side and the long side of the rectangle may be on the micrometer order. When the channel section is circular, the length of the diameter may be on the micrometer order.

In the present disclosure and the embodiments thereof, "light-induced force" is used as a generic term for dissipative force, gradient force, and inter-object light-induced force. The dissipative force is force generated when momentum of light is given to the material in a dissipation process such as light scattering or light absorption. The gradient force is force that moves the material to a stable point of an electromagnetic potential when the material in which light-induced polarization is generated is placed in an uneven electromagnetic field. The inter-material light-induced force is a sum of force due to a longitudinal electric field and force due to a transverse electric field (radiant field) generated from induced polarization in a plurality of materials that are optically excited.

In the present disclosure and the exemplary embodiments thereof, the term "resonance light" means light that causes the large light-induced polarization derived from electron excitation in the fine particle by incidence of the light on the fine particle. The light-induced polarization is electric polarization generated when electrons in the material are excited by light. For example, the "wavelength range of electronic resonance of fine particles" is a wavelength range corresponding to a full width at half maximum of the peak of localized surface plasmon resonance when the fine particle is the metal nanoparticle. This wavelength range is determined depending on the size of the fine particle, and the wavelength range is typically included in the wavelength range of visible light of 400 nm to 700 nm when the fine particle is the metal nanoparticle. When the fine particle is the semiconductor fine particle or the organic fine particle (the fine particle made of an organic material such as polystyrene), the wavelength range of the electronic resonance such as interband transition or exciton resonance (electron-hole pair resonance) becomes the wavelength range of resonance light. When the fine particle is the organic fine particle, the "wavelength range of the electronic resonance of the fine particle" is typically included in the wavelength range shorter than 400 nm.

On the other hand, the "non-resonant light" means light in which the light-induced polarization generated in the fine particle by the incidence on the fine particle is small. For example, when the fine particle is the metal fine particle, the "outside the wavelength range of the electronic resonance of the fine particle" is the wavelength range outside the full width at half maximum of the peak of the localized surface plasmon resonance. This wavelength range is determined depending on the size of the fine particle, and the wavelength range is typically included in the infrared wavelength range when the fine particle is the metal nanoparticle. The "infrared wavelength range" refers to the wavelength range of 700 nm to 10,000 μm (=1 mm), preferably the wavelength range of 700 nm to 2,500 nm, and more preferably the wavelength range of 700 nm to 1,400 nm. Sometimes "outside the wavelength range of the localized surface plasmon resonance of the fine particle" is included in an ultraviolet wavelength range (wavelength range of 10 nm to 400 nm). When the fine particle is the organic fine particle, "outside the wavelength range of the electronic resonance of the fine particle" is the wavelength range outside the wavelength range of the electronic resonance such as the interband transition or the exciton resonance (resonance of electron-hole pair). The wavelength range is included in a wavelength range longer than 400 nm.

In the present disclosure and the embodiments thereof, the "white light" means light having the wavelength range (for example, a wavelength range of 200 nm to 1100 nm) from an ultraviolet region to a near infrared region. The white light may be continuous light or pulsed light.

First Embodiment

<Detection Principle of Analyte>

FIG. 1 is a conceptual diagram illustrating a detection principle of a certain analyte. In the first embodiment, the analyte is detected using what is called a latex aggregation method. More particularly, in the example of FIG. 1, two types of beads B1, B2 are prepared.

Each of beads B1, B2 includes a common bead body B0. Bead body B0 is a resin bead (latex bead) made of polystyrene. Bead body B0 has a size in micrometer order (typically, a size of about 1 μm to about 5 μm in diameter) similarly to a general latex bead. A material of bead body B0 may be another resin such as acrylic, polyolefin, polyethylene, or polypropylene.

In bead B1, bead body B0 is modified with a first antibody B11. Avidin B12 and biotin B13 are used for modification of first antibody B11. Avidin B12 is fixed to the surface of bead body B0 by interaction between avidin B12 and bead body B0. Biotin B13 labels first antibody B11 by binding to first antibody B11. First antibody B11 is modified on the surface of bead body B0 by strong affinity between avidin B12 and biotin B13.

In bead B2, bead body B0 is modified with second antibody B21. Similarly to first antibody B11, second antibody B21 is also modified on the surface of bead body B0 with avidin B22 and biotin B23.

An analyte X in the example in FIG. 1 is an antigen. Specifically, the CD80 or the like can be used as analyte X. The CD80 may also be referred to as B7-1. Analyte X may be a material other than the antigen, an "epitope" meaning a site where an antibody binds to the antigen being provided in the material. Analyte X may be a material containing a plurality of epitopes. Such materials include a CD9/CD63 complex epitope.

Analyte X causes an antigen-antibody reaction with first antibody B11 and also causes an antigen-antibody reaction with second antibody B21. Accordingly, in existence of analyte X, bead B1 and bead B2 are bound through analyte X. FIG. 1 illustrates an example in which bead B1 is modified with only one first antibody B11. However, actual bead B1 is modified with more first antibody B11. The same applies to bead B2. Consequently, when the plurality of beads B1, B2 are introduced into the sample containing analyte X, the plurality of beads B1, B2 are aggregated by the antigen-antibody reaction to form the aggregates of beads B1, B2.

Figure 2:
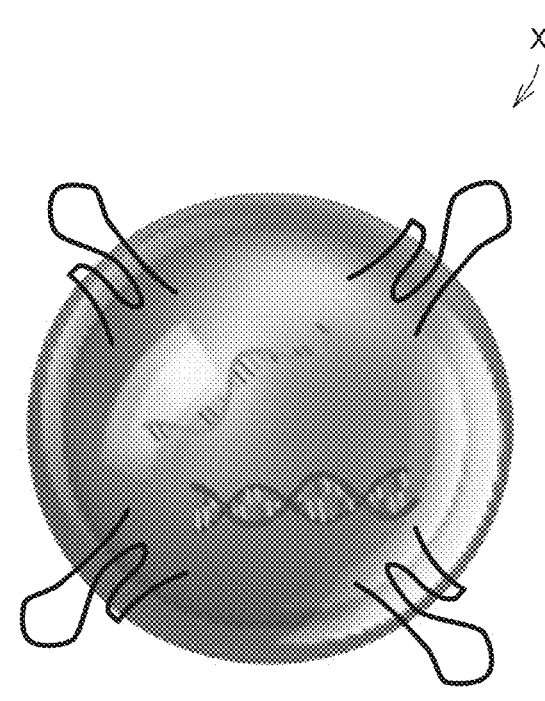
FIG. 2 is a view illustrating another example of the analyte.
Figure 3:
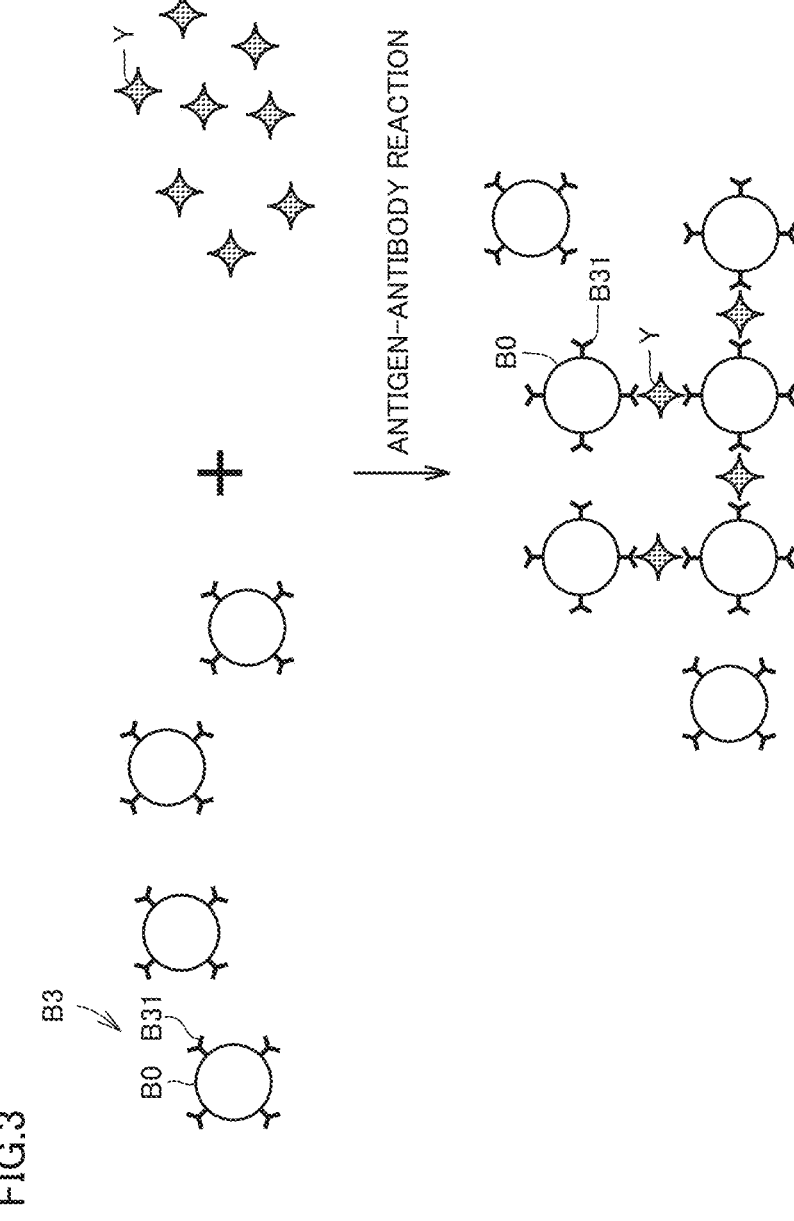
FIG. 3 is a conceptual diagram illustrating another detection principle of an analyte.

FIG. 2 is a view illustrating another example of analyte X. Analyte X may be an extracellular nanoparticle having various membrane proteins on the surface. Specifically, an exosome (extracellular vesicle) secreted from a cell can be used as analyte X. Exosomes derived from cancer cells such as large bowel cancer cells, lung cancer cells, and cervical cancer cells are known. The exosome is being studied for various applications such as utilization for a diagnosis as a biomarker. FIG. 3 schematically illustrates the exosome having a four-time transmembrane membrane protein (specifically, tetraspanin) on the surface thereof. A typical size of the exosome is about 30 nm to about 150 nm in diameter.

FIG. 3 is a conceptual diagram illustrating another detection principle of an analyte. The two kinds of beads are not necessarily required depending on the kind of the analyte. In the example of FIG. 3, only one type of bead B3 is prepared. Bead B3 includes bead body B0 and an antibody B31 modifying bead body B0.

An analyte Y in this example is also the antigen, specifically, for example, a fibrinogen fibrin degradation product (FDP). Even when the plurality of beads B3 and analyte Y are combined, the plurality of beads B3 are aggregated by the antigen-antibody reaction with analyte Y, and the aggregate of the beads B3 is formed.

<Entire Configuration of Detection System>

Figure 4:
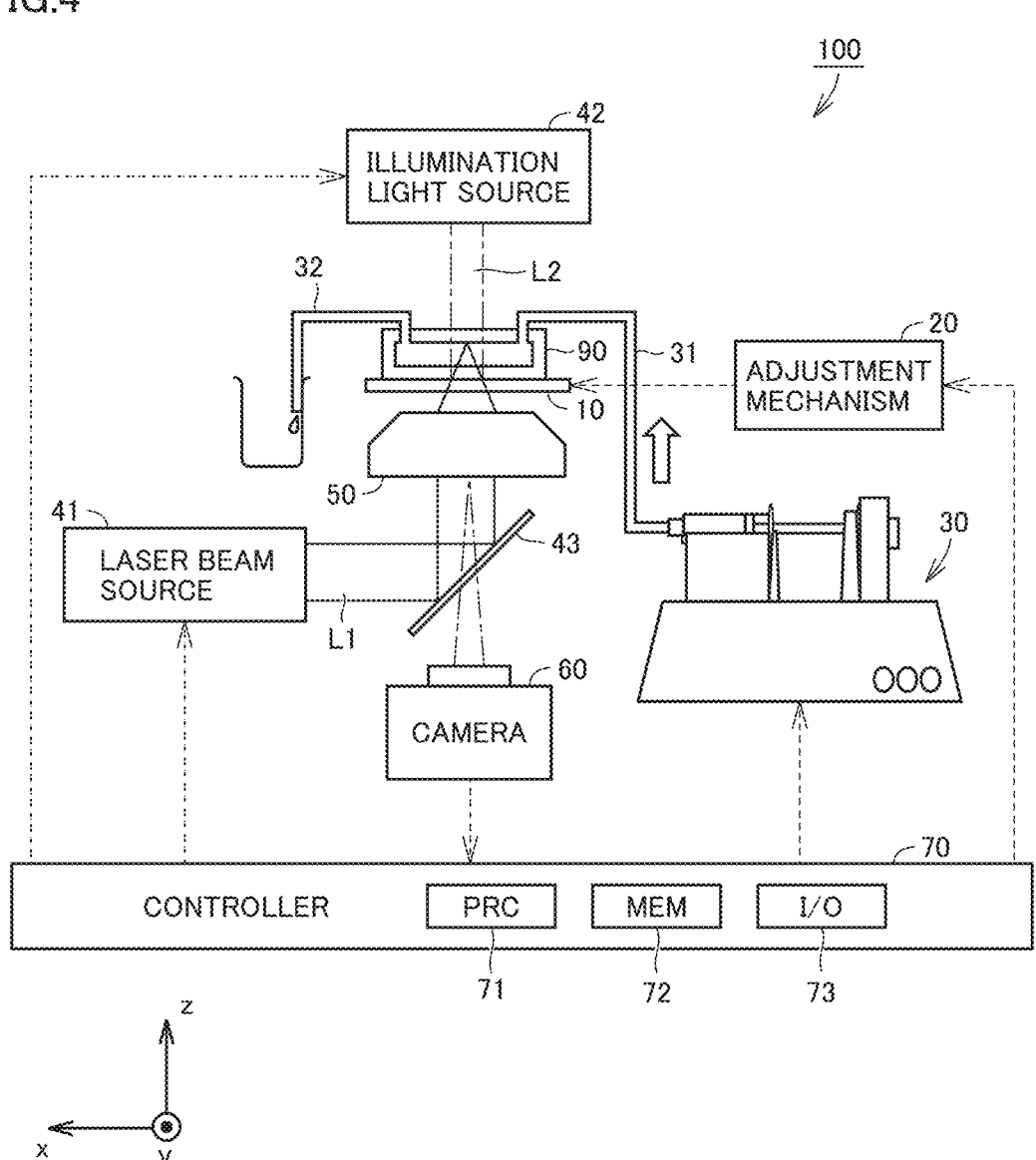
FIG. 4 is a schematic diagram illustrating an overall configuration of an antigen detection system according to a first embodiment.

FIG. 4 is a schematic diagram illustrating an overall configuration of an antigen detection system of the first embodiment. A configuration for detecting analyte X such as the CD80 (see FIG. 1) and the exosome (see FIG. 2) will be representatively described below. An x-direction and a y-direction represent a horizontal direction. The x-direction and the y-direction are orthogonal to each other. A z-direction represents a vertical direction. The direction of gravity is downward in the z-direction.

Referring to FIG. 4, an antigen detection system 100 of the first embodiment includes an XYZ-axis stage 10, an adjustment mechanism 20, a syringe pump 30, a laser beam source 41, an illumination light source 42, a dichroic mirror 43, an objective lens 50, a camera 60, and a controller 70.

Figure 5:
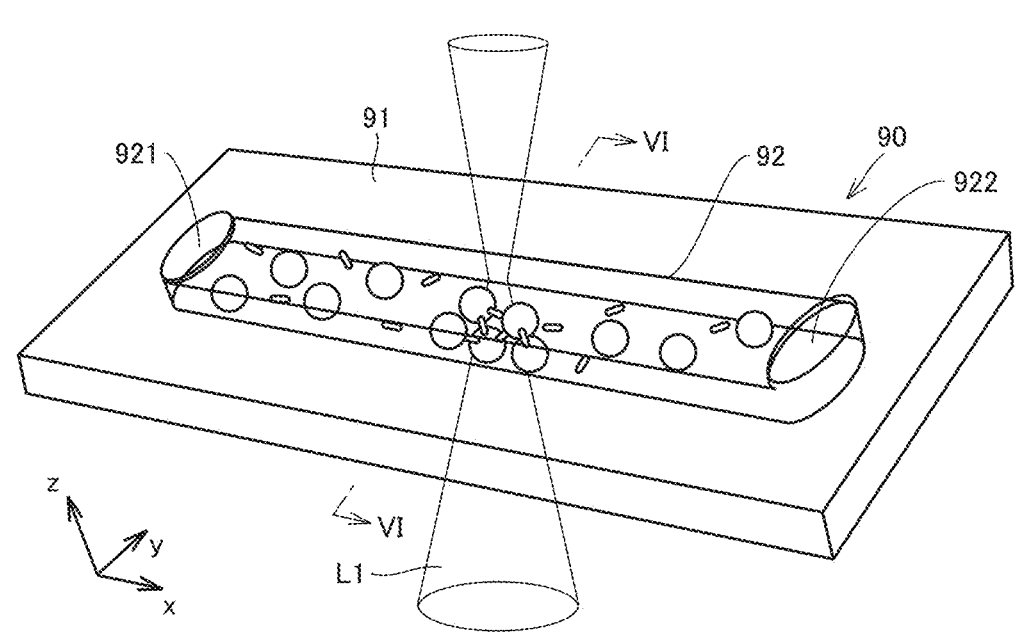
FIG. 5 is a schematic view illustrating a state of a detection kit during irradiation with a laser beam.
Figure 6:
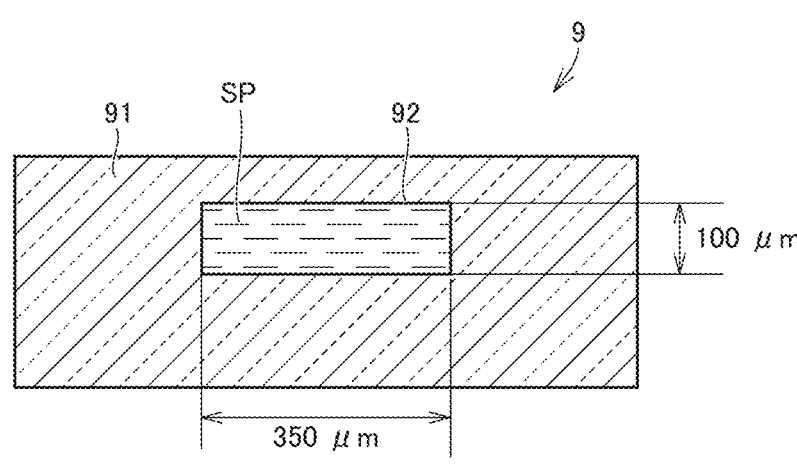
FIG. 6 is a sectional view of the detection kit taken along line VI-VI in FIG. 5.
Figure 6:
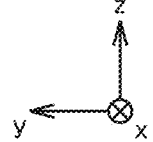

XYZ-axis stage 10 is configured to hold a detection kit 90. Detection kit 90 is a microchannel chip in which a microchannel 92 through which a sample SP is distributed is provided on a substrate 91. Sample SP is a liquid sample possibly containing analyte X. With reference to FIGS. 5 and 6, a detailed configuration of detection kit 90 will be described. A capillary 31 introducing sample SP into microchannel 92 and a capillary 32 discharging sample SP from microchannel 92 are connected to detection kit 90. XYZ-axis stage 10 corresponds to the "holder" according to the present disclosure.

Adjustment mechanism 20 adjusts the positions in the x-direction, the y-direction, and the z-direction of XYZ-axis stage 10 on which detection kit 90 is installed in response to a command from controller 70. In the first embodiment, a position of objective lens 50 is fixed. Consequently, the relative positional relationship between detection kit 90 and objective lens 50 is adjusted by adjusting the position of XYZ-axis stage 10. For example, a drive mechanism such as a servomotor and a focusing handle attached to a microscope can be used as adjustment mechanism 20. However, a specific configuration of adjustment mechanism 20 is not particularly limited. Adjustment mechanism 20 may adjust the position of objective lens 50 with respect to fixed detection kit 90.

Although not illustrated, a laser displacement meter may be provided in antigen detection system 100. The laser displacement meter measures a distance in the vertical direction between a laser emission port of the laser displacement meter and detection kit 90, and measures displacement of detection kit 90 in the horizontal direction. Adjustment mechanism 20 can adjust the position of XYZ-axis stage 10 based on the measurement result of the laser displacement meter, thereby adjusting the position (described later) of a beam waist of a laser beam L1 emitted from laser beam source 41.

Syringe pump 30 is connected to capillary 31 provided on an upstream side of microchannel 92. Syringe pump 30 adjusts a pressure driven flow in response to a command from controller 70 to discharge sample SP to capillary 31, thereby causing sample SP to be distributed in detection kit 90. Furthermore, syringe pump 30 is configured to adjust a flow velocity (hereinafter, described as a "flow velocity V") of sample SP by the pressure driven flow.

Syringe pump 30 corresponds to the "pump" according to the present disclosure. The "pump" may be configured to feed sample SP by action such as pressure, centrifugal force, or rotational force. The "pump" is not necessarily an electric type, and may be a manual type. For this reason, for example, a dispenser or a micropipette may be adopted instead of syringe pump 30.

Figure 11:
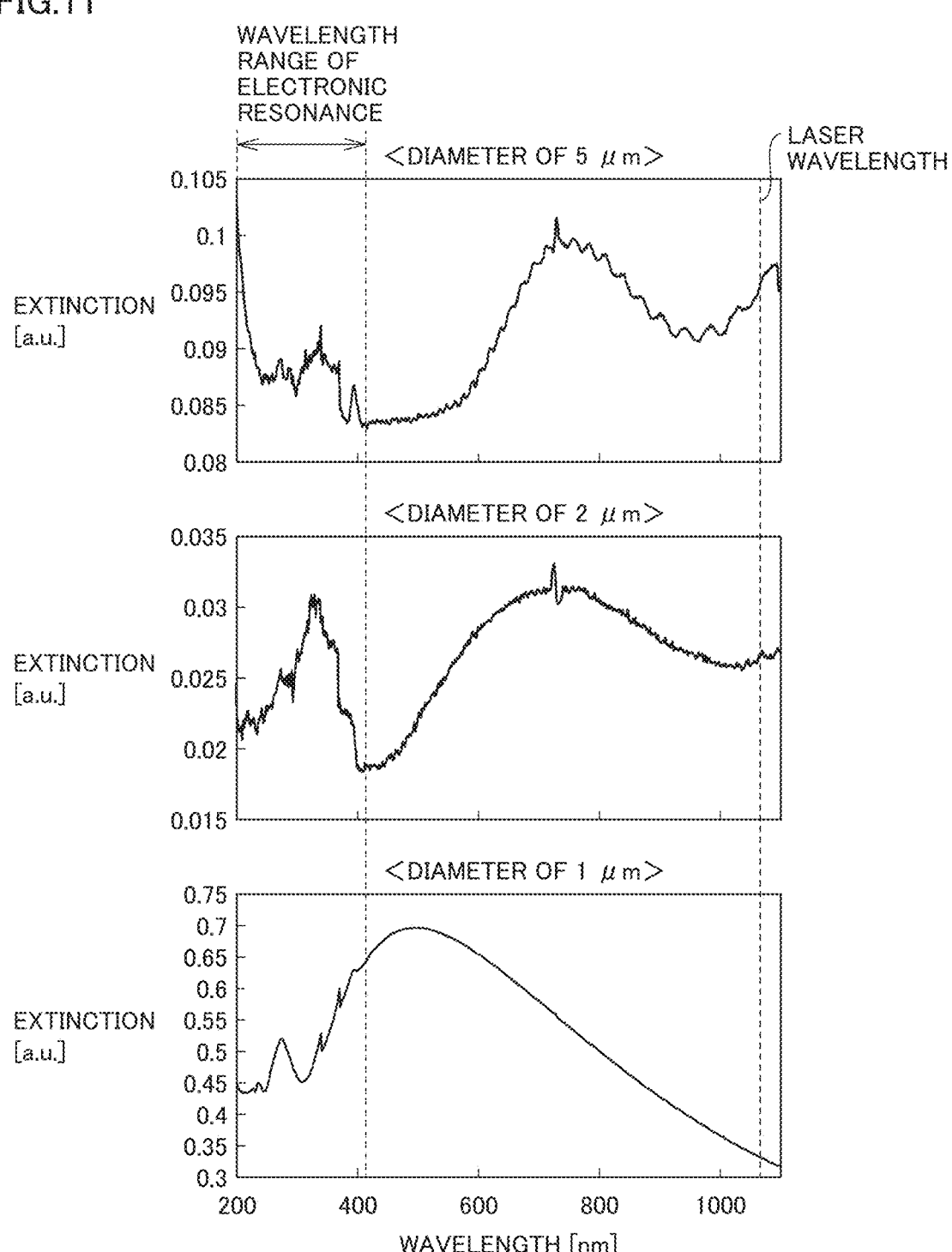
FIG. 11 is a view illustrating an example of a measurement result of an extinction spectrum of the latex bead.

Laser beam source 41 emits laser beam L1 in response to the command from controller 70. Laser beam L1 is used to capture fine particles in sample SP by generating the light-induced force. Laser beam L1 is the "non-resonant light" having a wavelength outside a wavelength range of the electronic resonance of beads B1, B2. The wavelength range of the electronic resonance varies depending on the size (diameter) of beads B1, B2. Beads B1, B2 in the first embodiment have a diameter of 2 μm. In this case, the wavelength range of the electronic resonance of beads B1, B2 has a wavelength range less than 400 nm. On the other hand, the wavelength of laser beam L1 is a wavelength outside the wavelength range of the electronic resonance, and for example, is a wavelength (1064 nm in the first embodiment) included in a near-infrared region. As described above, by adopting an appropriate combination of the diameter of beads B1, B2 and the wavelength of laser beam L1, the condition that laser beam L1 causes Mie scattering can be satisfied when beads B1, B2 are irradiated with laser beam L1. With reference to FIG. 11, the Mie scattering will be described in detail. Laser beam source 41 corresponds to the "light source" according to the present disclosure.

Illumination light source 42 emits white light L2 illuminating sample SP in detection kit 90 in response to the command from controller 70. As an example, a halogen lamp can be used as illumination light source 42.

Dichroic mirror 43 reflects laser beam L1 from laser beam source 41 and transmits white light L2 from illumination light source 42. For example, dichroic mirror 43 and objective lens 50 can be incorporated into an inverted microscope body or an upright microscope body.

Objective lens 50 condenses laser beam L1 that is emitted from laser beam source 41 and reflected by dichroic mirror 43. Detection kit 90 (more specifically, microchannel 92 (see FIG. 5)) is irradiated with the light condensed by objective lens 50. Objective lens 50 is also used to capture white light L2 emitted from illumination light source 42 to detection kit 90. White light L2 taken in by objective lens 50 is guided to camera 60 by dichroic mirror 43.

In response to the command from controller 70, camera 60 captures sample SP in detection kit 90 irradiated with white light L2, and outputs the captured image to controller 70. Camera 60 may be a steel camera that captures a still image or a video camera that captures a moving image. Camera 60 corresponds to the "optical receiver" according to the present disclosure. The "optical receiver" according to the present disclosure is not limited to a device that outputs image data, but may include a photodiode, a photomultiplier (PMT), and the like.

Controller 70 is a microcomputer including a processor 71 such as a central processing unit (CPU), a memory 72 such as a random access memory (RAM) and a read only memory (ROM), and an input and output port 73. Controller 70 controls each device (adjustment mechanism 20, syringe pump 30, laser beam source 41, illumination light source 42, and camera 60) in antigen detection system 100. In addition, controller 70 executes "antigen detection process" of detecting the antigen by applying predetermined image processing to the image captured by camera 60. The antigen detection process by controller 70 will be described in detail later. Controller 70 corresponds to the "arithmetic device" according to the present disclosure.

An optical system of antigen detection system 100 is not limited to the configuration in FIG. 4 as long as detection kit 90 can be irradiated with laser beam L1 from laser beam source 41 while white light L2 from detection kit 90 can be taken into camera 60. For example, the irradiation direction of laser beam L1 with respect to detection kit 90 can be appropriately changed as described later with reference to FIG. 7. The optical system of antigen detection system 100 may include other optical components (such as a mirror, a beam splitter, a prism, and an optical fiber) instead of or in addition to dichroic mirror 43. In antigen detection system 100, adjustment mechanism 20 and illumination light source 42 are not essential components.

<Configuration of Detection Kit>

FIG. 5 is a schematic view illustrating a state of detection kit 90 during irradiation with laser beam L1. As described above, microchannel 92 is formed in substrate 91 of detection kit 90. In the example of FIG. 5, microchannel 92 is an unbranched channel in which one outlet 922 is formed for one inlet 921. Hereinafter, the distribution direction of sample SP in microchannel 92 is set to the x-direction.

Detection kit 90 can be made of a material transparent to laser beam L1 and white light L2. Preferably the material used in detection kit 90 is a material such as glass or quartz, that does not exhibit anisotropy with respect to laser beam L1 that is polarized light.

FIG. 6 is a sectional view of detection kit 90 taken along line VI-VI in FIG. 5. As illustrated in FIG. 6, for example, a section of microchannel 92 has a rectangular shape. As an example, the width (channel width, length in y-direction) of the rectangle is 350 μm, and the height (length in z-direction) of the rectangle is 100 μm. Sample SP is distributed in microchannel 92 in the state in which microchannel 92 is filled with sample SP (that is, in the state of not containing air).

Figure 7:
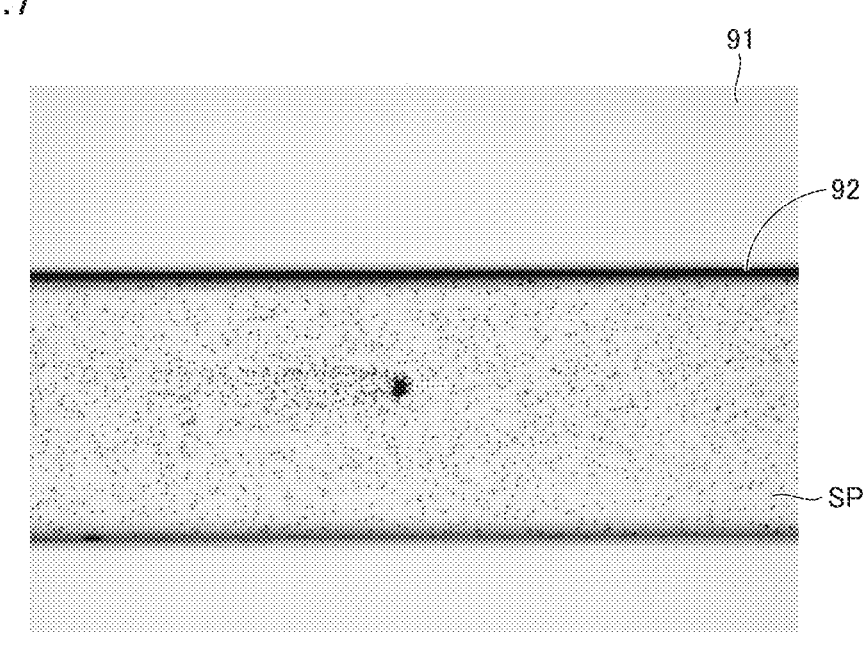
FIG. 7 is an image obtained by capturing the detection kit during the irradiation with the laser beam.
Figure 7:
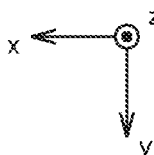

FIG. 7 is an image obtained by capturing detection kit 90 during the irradiation with laser beam L1. Each of minute black spots in microchannel 92 is bead B1 or bead B2. The distribution direction of sample SP is a direction (x-direction) from the right side to the left side of the image. It can be confirmed that the aggregates of beads B1, B2 are formed near the center of the image.

<Upward Irradiation and Downward Irradiation>

Figure 8:
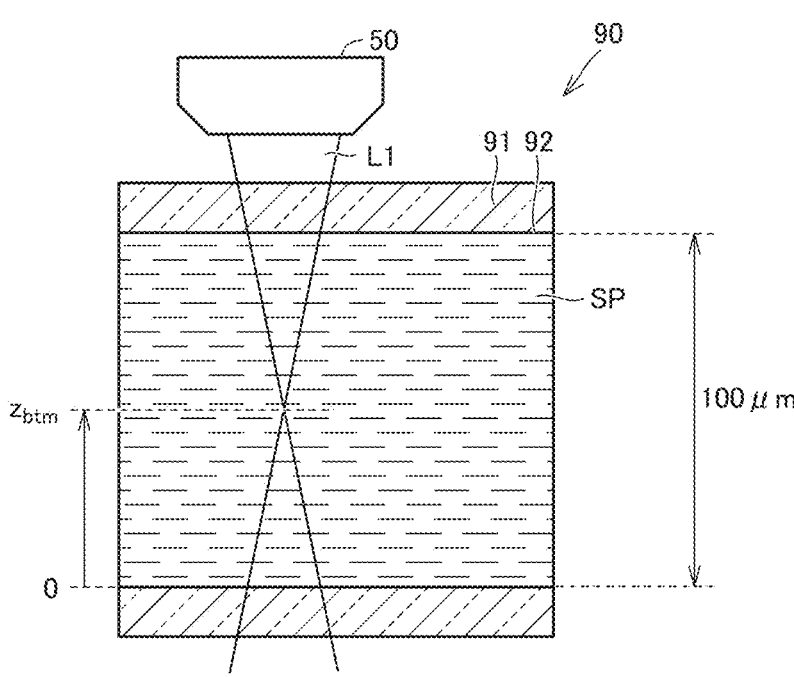
FIG. 8 is a view illustrating a mode in which the detection kit is irradiated with the laser beam.
Figure 8:
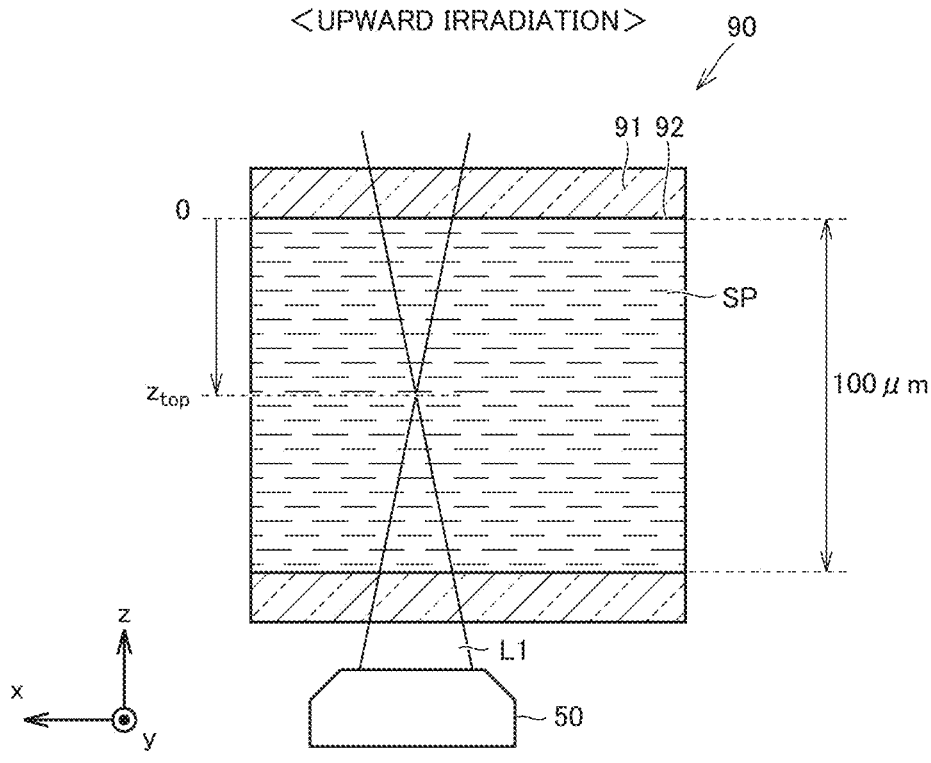

FIG. 8 is a view illustrating a mode in which detection kit 90 is irradiated with laser beam L1. In the first embodiment, the optical system of antigen detection system 100 is configured such that detection kit 90 is irradiated with laser beam L1 in any one of two irradiation modes. Hereinafter, the irradiation mode of laser beam L1, in which objective lens 50 is disposed above detection kit 90 and laser beam L1 is irradiated from the upper side to the lower side of detection kit 90, is also referred to as "downward irradiation". On the other hand, the irradiation mode of laser beam L1, in which objective lens 50 is disposed below detection kit 90 and laser beam L1 is irradiated from the lower side to the upper side of detection kit 90, is also referred to as the "upward irradiation".

The beam waist of laser beam L1 is formed at the focal point of objective lens 50. A beam diameter (minimum spot diameter $\varphi_0$) at the beam waist is for example several μm to several tens μm. An irradiation area of laser beam L1 with respect to sample SP flowing through microchannel 92 increases as minimum spot diameter $\varphi_0$ increases. Accordingly, when intensity of laser beam L1 is sufficiently high, there is a possibility that beads B1, B2 can be more accumulated. In addition, the amount of beads B1, B2 passing through microchannel 92 without being irradiated with laser beam L1 can be reduced as minimum spot diameter $\varphi_0$ is larger.

In some measurement examples (FIGS. 15, 17, 18, and the like) described later, the relative positional relationship between detection kit 90 and objective lens 50 is adjusted such that the beam waist is located inside microchannel 92 in both the downward irradiation and the upward irradiation (focus condition). The height of the beam waist is known from the wavelength of laser beam L1 and the specifications (magnification and the like) of objective lens 50. Accordingly, the beam waist can be adjusted to a target height by adjusting the position in the vertical direction of XYZ-axis stage 10 using adjustment mechanism 20.

In the downward irradiation, the position (z-coordinate) in the vertical direction of the beam waist of laser beam L1 is described as $z_{btm}$ when the bottom surface of microchannel 92 is set to a reference (z=0). For example, in the case of $z_{btm}=0$, the beam waist of laser beam L1 is located on the bottom surface of microchannel 92. In the case of $z_{btm}=50$ μm, the beam waist of laser beam L1 is located above the bottom surface of microchannel 92 by 50 μm. On the other hand, in the upward irradiation, the position (z-coordinate) in the vertical direction of the beam waist of laser beam L1 is described as $z_{top}$ when the upper surface of microchannel 92 is set to a reference (z=0).

Minimum spot diameter $\varphi_0$ of laser beam L1 may vary depending on the position $z_{btm}$ (or $z_{top}$) of the beam waist in addition to the magnification of objective lens 50. In a certain measurement example, minimum spot diameter $\varphi_0=4.66$ μm when the magnification of objective lens 50 was 10 times and $z_{btm}=0$. Minimum spot diameter $\varphi_0=19.7$ μm when the magnification of objective lens 50 was 10 times and $z_{btm}=50$ μm.

<Aggregation Mechanism>

Figure 9:
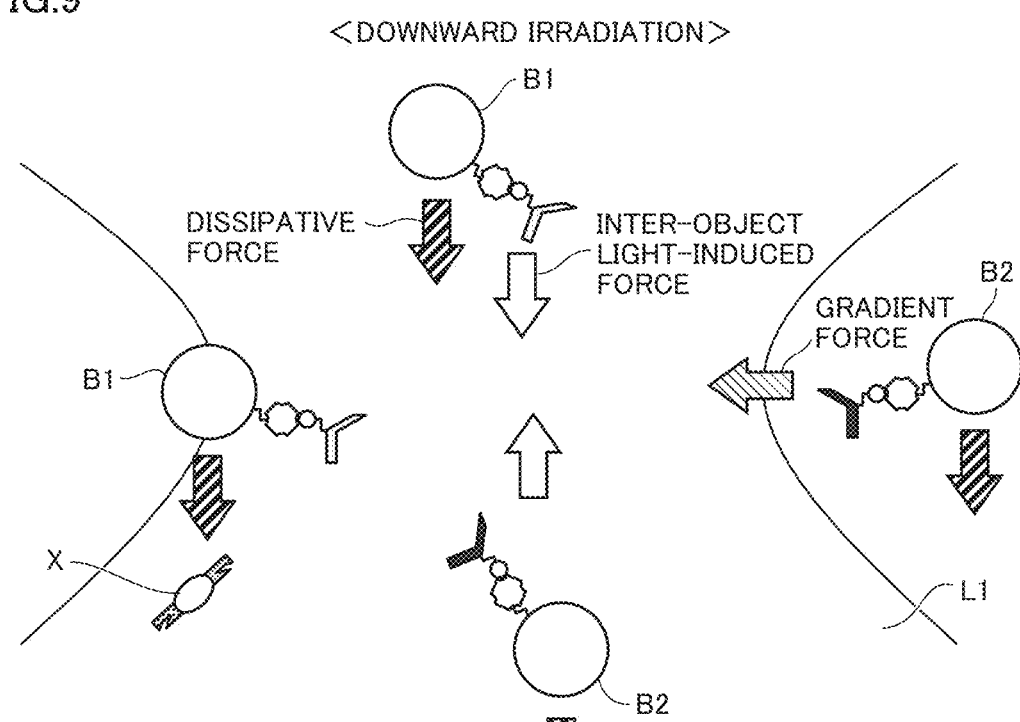
FIG. 9 is a view illustrating an aggregation mechanism of a latex bead when the detection kit is irradiated with the laser beam.
Figure 9:
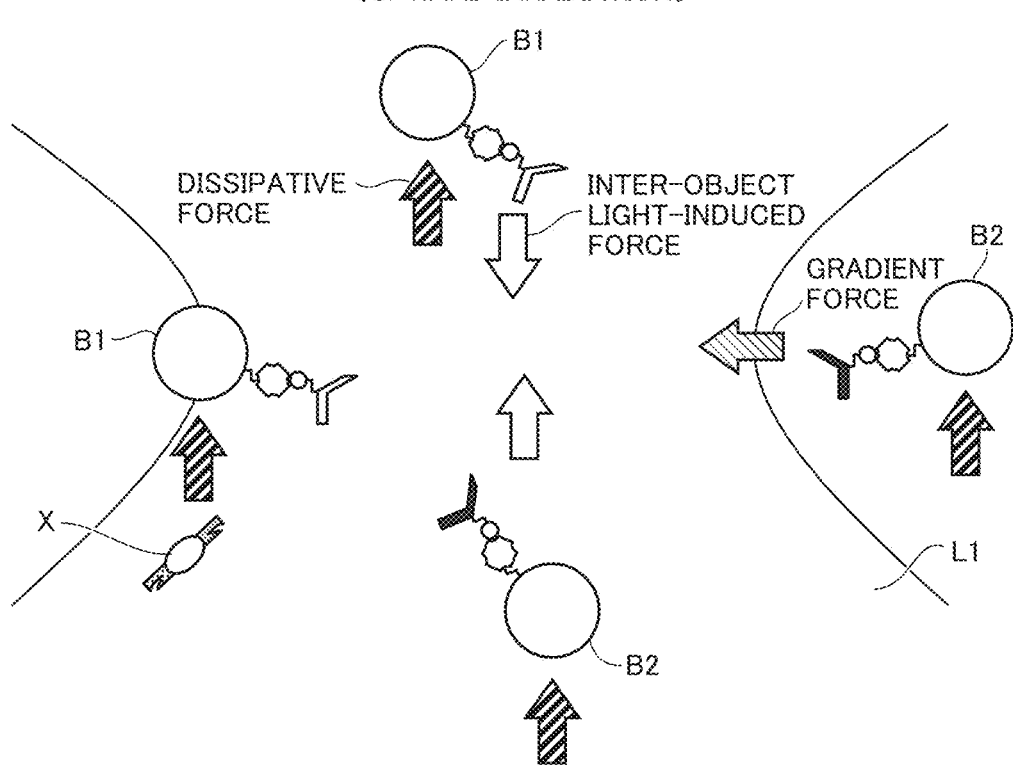

FIG. 9 is a view illustrating an aggregation mechanism of beads B1, B2 when detection kit 90 is irradiated with laser beam L1. When detection kit 90 is irradiated with laser beam L1 after the beam waist of laser beam L1 is adjusted to be located in sample SP, beads B1, B2 gather near the beam waist by the light-induced force (more particularly, the inter-object light-induced force and the gradient force). Thus, the density of beads B1, B2 near the beam waist is locally higher than the density of beads B1, B2 at other positions (positions sufficiently distant from the beam waist).

When analyte X exists around the beam waist, as described in FIG. 1, the antigen-antibody reaction occurs between first antibody B11 modified on the surface of bead B1 and analyte X and between second antibody B21 modified on the surface of bead B2 and analyte X, and bead B1 and bead B2 are bound through analyte X. In antigen detection system 100, because new analyte X is sequentially supplied around the beam waist by distributing sample SP using syringe pump 30, the antigen-antibody reaction is easily to occur as compared with in the stationary liquid. The aggregates of beads B1, B2 are formed by repeating the antigen-antibody reaction.

As the size of the aggregates of beads B1, B2 increases, a probability that analyte X existing around the aggregate encounters the aggregate increases, so that a frequency at which the antigen-antibody reaction occurs increases. In other words, according to antigen detection system 100 of the first embodiment, "light-induced acceleration" that accelerates the aggregation of beads B1, B2 by the irradiation with laser beam L1 can be implemented. As a result, the aggregates in which beads B1, B2 are densely aggregated are formed in a short time. Then, by optically detecting the formed aggregate, sample SP can be quickly determined to contain analyte X.

The dissipative force acts on beads B1, B2 in the same direction as the irradiation direction of laser beam L1 in addition to the inter-object light-induced force and the gradient force. In the case of the upward irradiation, beads B1, B2 are pressed against the upper surface of microchannel 92 by application of the dissipative force from the lower side to the upper side. On the other hand, in the case of the downward irradiation, beads B1, B2 are pressed against the bottom surface of microchannel 92 by application of the dissipative force from the upper side to the lower side.

A specific gravity of the latex bead is about 1.04 [g/cm³], which is equivalent to the specific gravity of water, whereas the specific gravity of a magnetic bead is about 1.6 [g/cm³]. When the specific gravity (mass density) of the fine particle is sufficiently larger than the specific gravity of a surrounding dispersion medium (in this example, pure water) like the magnetic bead, the fine particle tends to settle in sample SP after stirring and standing and disperse at the position close to the bottom surface of microchannel 92. Consequently, the downward irradiation in which the aggregate is formed on the bottom surface of microchannel 92 is more effective than the upward irradiation in which the aggregate is formed on the upper surface of microchannel 92, and the aggregate of fine particle can be more efficiently formed.

FIG. 10 is a conceptual diagram illustrating a relationship between a size of beads B1, B2 and a wavelength of laser beam L1. As described above, typical diameters of beads B1, B2 are about 1 μm to about 5 μm (in examples described later, about 2 μm). The wavelength range of the electronic resonance of beads B1, B2 is determined according to the diameters of beads B1, B2, and is the wavelength range shorter than 400 nm with respect to the diameter.

When laser beam L1 has the wavelength sufficiently longer than the diameters of beads B1, B2 (for example, the wavelength greater than or equal to 10 times), most of laser beam L1 passes through beads B1, B2 without stopping. More particularly, laser beam L1 emitted to beads B1, B2 causes Rayleigh scattering. The dissipative force generated by the Rayleigh scattering is proportional to the sixth power of the diameters of beads B1, B2. Accordingly, only the weak light-induced force is generated in the Rayleigh scattering.

On the other hand, in the first embodiment, laser beam L1 is the non-resonant light having the wavelength outside the wavelength range of the electronic resonance. Specifically, laser beam L1 has the wavelength of 1064 nm, namely, the wavelength equivalent to the diameters of beads B1, B2.

FIG. 11 is a view illustrating an example of a measurement result of an extinction spectrum of beads B1, B2. FIG. 11 illustrates extinction spectra in order from the top in the case where the diameters of beads B1, B2 are 5 μm, in the case where the diameters of beads B1, B2 are 2 μm, and in the case where the diameters of beads B1, B2 are 1 μm. The extinction spectrum is obtained by adding a scattering spectrum and an absorption spectrum.

As can be seen from FIG. 11, the particularly large extinction is caused around the wavelength of 1064 nm when the diameters of beads B1, B2 are 5 μm or 2 μm. This is because the Mie scattering occurs after laser beam L1 is confined in beads B1, B2 when laser beam L1 has the wavelength equivalent to the diameter of beads B1, B2 (see FIG. 10).

The strong light-induced force is generated because the dissipative force generated by the Mie scattering is proportional to the square of the diameters of beads B1, B2. Beads B1, B2 can be more strongly pressed against the upper surface (in the case of the upward irradiation) or the bottom surface (in the case of the downward irradiation) of microchannel 92 by the strong light-induced force. As a result, the aggregates of beads B1, B2 can be more efficiently formed.

As described above, the combination of the diameters of beads B1, B2 and the wavelength of laser beam L1 is desirably selected such that laser beam L1 causes the Mie scattering when beads B1, B2 are irradiated. It has been described that the diameters of beads B1, B2 are first determined, and then the wavelength of laser beam L1 is selected according to the diameters of beads B1, B2. However, the diameters of beads B1, B2 used may be selected according to the wavelength of laser beam L1.

<Antigen Detection Flow>

Subsequently, two types of antigen detection process in the first embodiment will be described. First antigen detection process is process of detecting whether analyte X is contained in sample SP. Second antigen detection process is process of quantifying the concentration of analyte X contained in sample SP.

Figure 12:
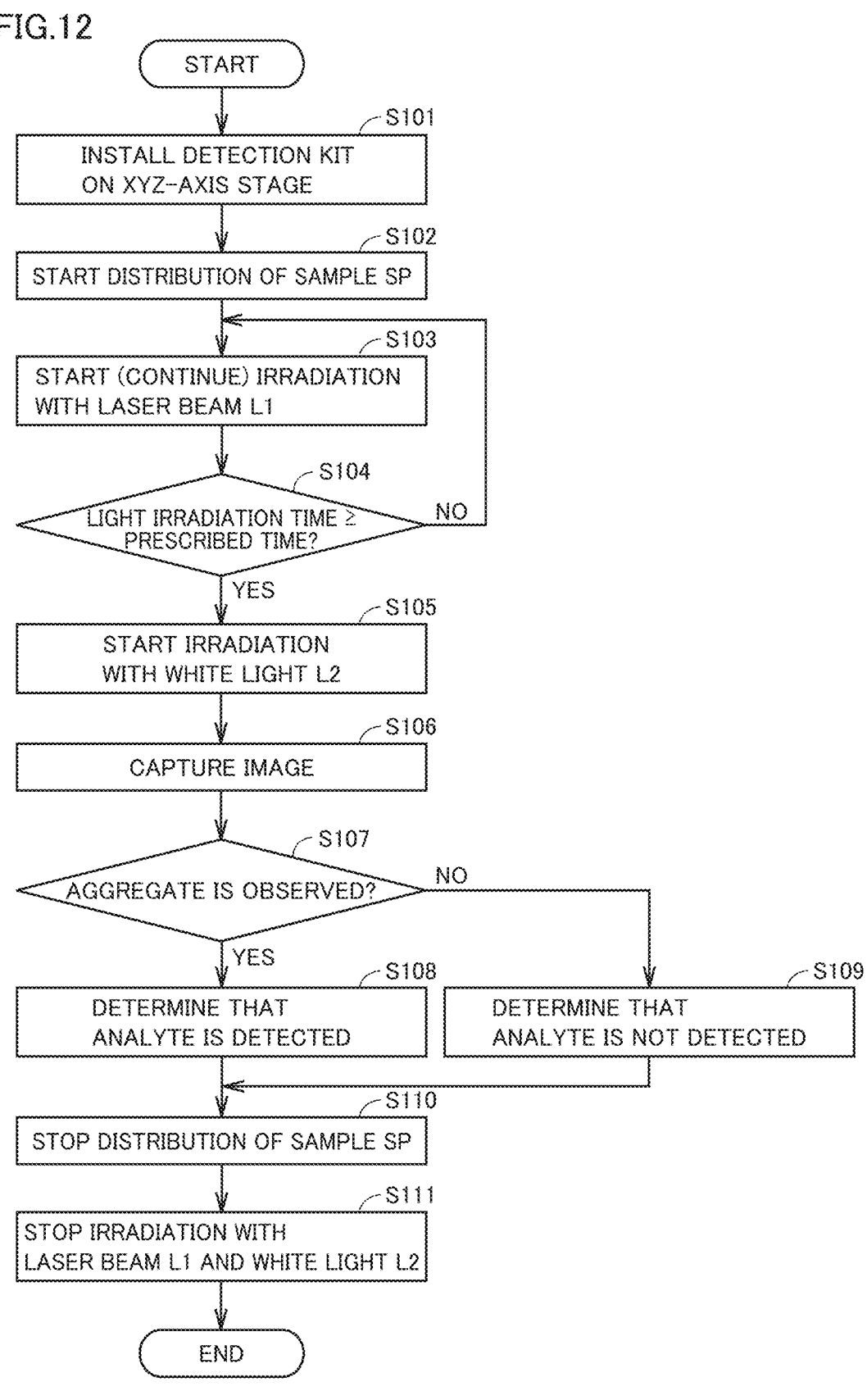
FIG. 12 is a flowchart illustrating first antigen detection process in the first embodiment.

FIG. 12 is a flowchart illustrating first antigen detection process in the first embodiment. The flowcharts in FIG. 12 and FIG. 13 described later are executed when a predetermined condition is satisfied (for example, when the user operates a start button (not illustrated)). Each step included in these flowcharts is basically implemented by software processing by controller 70, and a part or all of the steps may be implemented by hardware (electric circuit) manufactured in controller 70. Hereinafter, the step is simply referred to as "S".

The position ($z_{btm}$ that is the z-coordinate when the bottom surface of microchannel 92 is set to the reference (z=0), or $z_{top}$ that is the z-coordinate when the upper surface of microchannel 92 is set to the reference (z=0)) of the beam waist of laser beam L1 is previously set to a desired value.

Referring to FIG. 12, in S101, controller 70 installs detection kit 90 on XYZ-axis stage 10. For example, this process can be implemented by a feeding mechanism (not illustrated) of detection kit 90. However, the user may manually install detection kit 90.

In S102, controller 70 controls syringe pump 30 so as to start the distribution of sample SP to detection kit 90. At this time, controller 70 preferably controls syringe pump 30 such that flow velocity V of sample SP becomes an appropriate flow velocity previously experimentally obtained. Here, flow velocity V is a time average of the flow velocity of sample SP from the start of the flow velocity to the end of the distribution.

In step S103, controller 70 controls laser beam source 41 to start (or continue) the irradiation of detection kit 90 with laser beam L1. As a result, when analyte X is contained in sample SP, analyte X encounters beads B1, B2 captured by the light-induced force, and analyte X and beads B1, B2 are bound to each other, whereby the aggregates of beads B1, B2 are formed. The aggregates of beads B1, B2 grow as the irradiation time of laser beam L1 becomes longer.

In step S104, controller 70 determines whether elapsed time from the start of the irradiation with laser beam L1 reaches prescribed time (in the example described later, three minutes or four minutes). When the light irradiation time does not reach the prescribed time (NO in S4), controller 70 returns the process to S103. Thus, the irradiation with laser beam L1 is continued. When the light irradiation time reaches the prescribed time (YES in S104), controller 70 advances the process to S105.

In S105, controller 70 controls illumination light source 42 to start the irradiation of detection kit 90 with white light L2. Then, controller 70 controls camera 60 to capture the image of detection kit 90 at the irradiation position of laser beam L1 (step S106).

In S107, controller 70 determines whether the aggregates of beads B1, B2 are observed in the image by performing predetermined image processing on the image captured in S106. For the image processing, various known image processing techniques can be used. For example, in the region where the aggregates of beads B1, B2 are formed, the transmitted light of white light L2 decreases and the color of the image becomes deep (see FIG. 17 and the like described later). Accordingly, whether the aggregates of beads B1, B2 are formed can be determined based on the existence of the region where the color of the image becomes deep (or the size of the area of the region). Alternatively, whether the aggregates are formed can be determined by extracting features of the shapes of the aggregates of beads B1, B2 using a pattern recognition technique.

Furthermore, when another optical receiver (photodiode or the like) is used instead of the camera, the existence of the aggregates of beads B1, B2 can be determined based on the signal intensity from the optical receiver. More specifically, when the aggregates of beads B1, B2 are formed, white light L2 is blocked by the aggregates of beads B1, B2. For this reason, when the aggregates of beads B1, B2 are formed, the signal intensity from the optical receiver decreases as compared with the case where the aggregates of beads B1, B2 are not formed. Accordingly, the existence of the aggregates of beads B1, B2 can be determined by whether the signal intensity from the optical receiver decreased during the irradiation with laser beam L1.

When the aggregates of beads B1, B2 are observed (YES in S107), controller 70 determines that analyte X is contained in sample SP (S108). On the other hand, when the aggregates of beads B1, B2 are not observed (NO in S107), controller 70 determines that analyte X is not detected (not contained in sample SP) (S109).

Then, controller 70 controls syringe pump 30 so as to stop the distribution of sample SP (S110). Furthermore, controller 70 controls laser beam source 41 so as to stop the irradiation with laser beam L1, and controls illumination light source 42 so as to stop the irradiation with white light L2 (S111). Thus, a series of process ends.

The order of the process of starting the distribution of sample SP (the process in S102), the process of starting the irradiation with laser beam L1 (the process in S103), and the process of starting the irradiation with white light L2 (the process in S105) can be appropriately changed. For example, the distribution of sample SP may be started while the image (in this case, the moving image) of detection kit 90 is captured under the irradiation with white light L2, and then the irradiation with laser beam L1 may be started. Conversely, the irradiation with laser beam L1 may be started during the capture of the moving image, and then the distribution of sample SP may be started.

Figure 13:
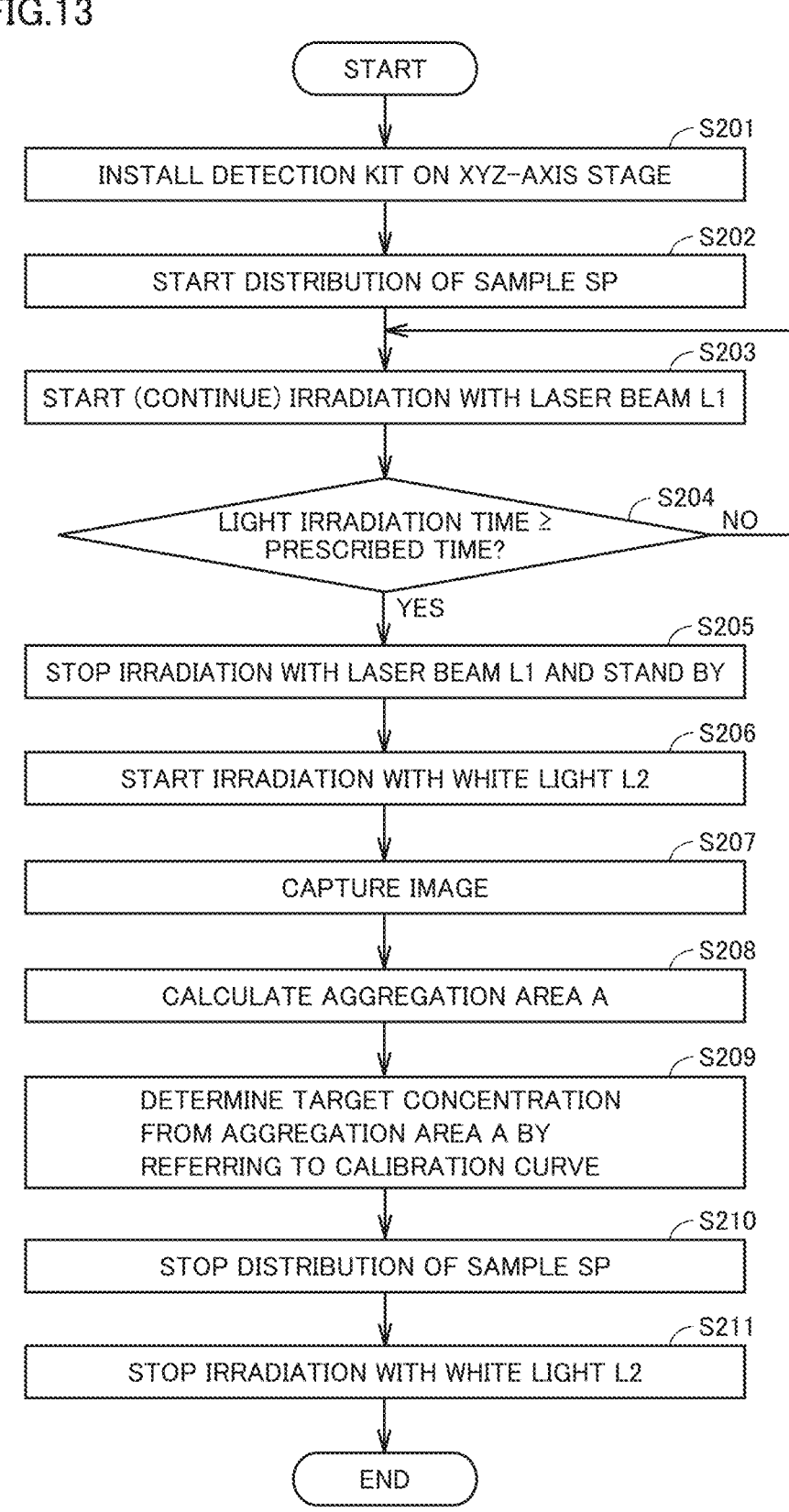
FIG. 13 is a flowchart illustrating second antigen detection process in the first embodiment.

FIG. 13 is a flowchart illustrating second antigen detection process in the first embodiment. Referring to FIG. 13, the process of S201 to S204 is similar to the process of S101 to S104 in the first antigen detection process (see FIG. 12), so that the description will not be repeated.

In step S205, controller 70 controls laser beam source 41 to stop the irradiation with laser beam L1. Furthermore, controller 70 stands by for a predetermined time (in the example described later, 10 seconds) after stopping the irradiation with laser beam L1.

In S206, controller 70 controls illumination light source 42 to start the irradiation of detection kit 90 with white light L2. Then, controller 70 controls camera 60 to capture the image of detection kit 90 at the irradiation position of laser beam L1 (step S207).

In S208, controller 70 performs image processing on the image captured in S207, and calculates the area of the region where the color of the image becomes deep by the aggregation of beads B1, B2. Hereinafter, the area of the region is referred to as an "aggregation area A". Aggregation area A is an example of the "index representing the size of the aggregate" according to the present disclosure.

In S209, the concentration of analyte X is determined from aggregation area A calculated in S207 using a previously-prepared calibration curve. Hereinafter, the concentration of analyte X may be abbreviated as "target concentration".

Figure 14:
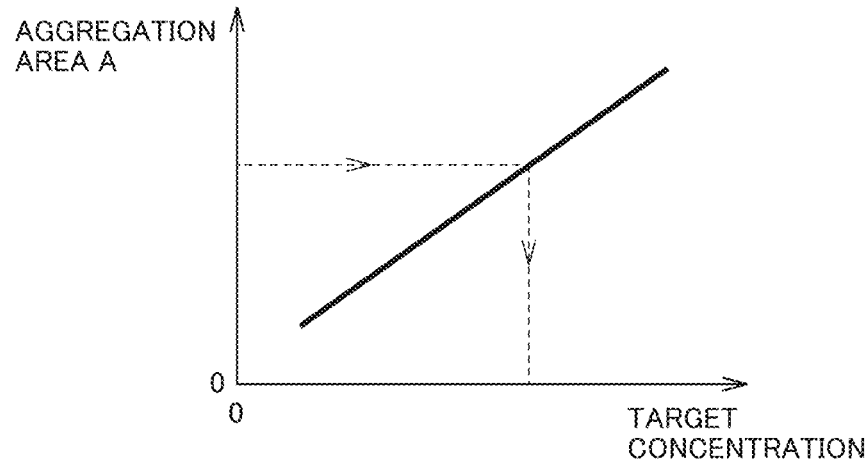
FIG. 14 is a conceptual diagram illustrating an example of a calibration curve calculating a concentration (target concentration) of a target antigen.
Figure 15:
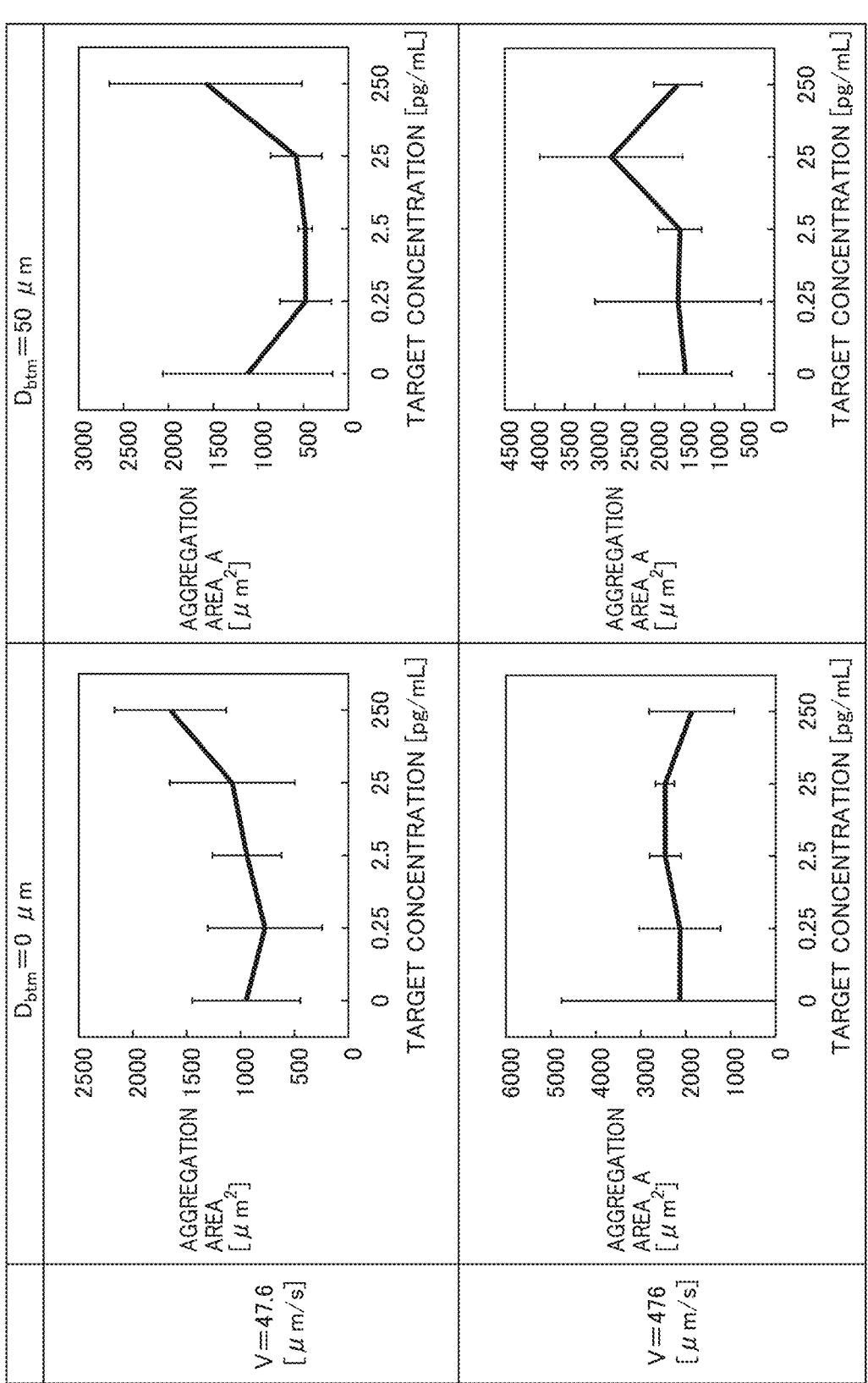
FIG. 15 is a view illustrating a measurement result of a relationship between a target concentration and an aggregation area of the latex bead.

FIG. 14 is a conceptual diagram illustrating an example of the calibration curve calculating the concentration of analyte X. In FIG. 14 and FIG. 15 and the like described later, the horizontal axis represents the concentration (target concentration) of analyte X. The vertical axis represents aggregation area A of beads B1, B2.

There is a correspondence relationship between the target concentration and aggregation area A of beads B1, B2. As illustrated in FIG. 14, the higher the target concentration, larger aggregation area A of beads B1, B2. Such a correspondence relationship is obtained by a preliminary experiment for each measurement condition (conditions regarding the intensity and irradiation time of laser beam L1, the magnification of objective lens 50, the position $z_{top}$ or $z_{btm}$ of the beam waist of laser beam L1, and the like), and stored in memory 72 of controller 70 as the calibration curve. Accordingly, controller 70 can determine the target concentration from aggregation area A of beads B1, B2 by reading the calibration curve corresponding to the measurement conditions from memory 72.

Returning to FIG. 13, the subsequent process of S210 and S211 is similar to the process of S110 and S111 in the flowchart of FIG. 12. As the process of S211 ends, a series of process ends. The process (process in S206) of stopping the irradiation with laser beam L1 to stand by in advance of the imaging of detection kit 90 is not essential. The effect of the standby process will be described later.

In the following Examples 1 to 4, the detection result of the analyte (concentration measurement result of the analyte) using antigen detection system 100 will be described. In Examples 1 to 4, the concentration of analyte X was measured using two kinds of beads B1, B2. Analyte X was CD80, and the surfaces of beads B1, B2 were modified with an anti-CD80 antibody.

Example 1

<Concentration Dependency of Target Antigen>

FIG. 15 is a view illustrating the measurement results of the relationship between the target concentration and aggregation area A of beads B1, B2 when analyte X is CD80. FIG. 15 illustrates measurement results when position $z_{btm}$ of the beam waist of laser beam L1 from the bottom surface of microchannel 92 in the downward irradiation is set to two ways ($z_{btm}$=0 μm, 50 μm) and when flow velocity V of sample SP is set to two ways (V=47.6 [μm/s], 476 [μm/s]) (that is, there are four measurement conditions depending on the combination of position $z_{btm}$ and flow velocity V).

Figure 18:
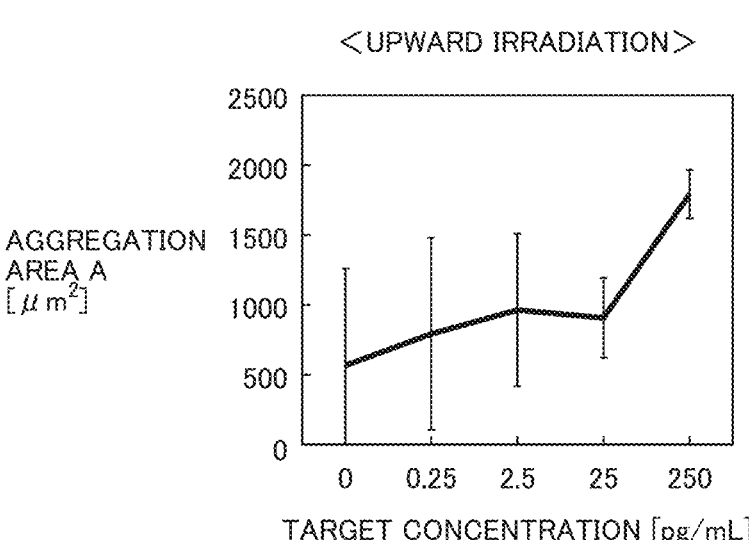
FIG. 18 is a view that illustrates the relationship between the target concentration and the aggregation area when the analyte is the CD80, the relationship being obtained from the image in FIG. 17.

In FIG. 15 and FIG. 18 described later and the like, an error bar represents a measurement error of a result of performing the measurement a plurality of times at each target concentration, specifically, a standard deviation of aggregation area A of beads B1, B2. In FIG. 15, error bars of four measurement results are illustrated in the case of flow velocity V=47.6 [μm/s], and error bars of three measurement results are illustrated in the case of flow velocity V=476 [μm/s].

Five types of target concentrations (mass concentration of analyte X) were prepared in a concentration range of 0 [pg/mL] to 250 [pg/mL]. The concentrations are extremely low, and the amount of analyte X contained in sample SP is extremely small. The magnification of objective lens 50 was 10 times.

Referring to FIG. 15, the proportional tendency was confirmed as illustrated in FIG. 14 that aggregation area A of beads B1, B2 basically increases with the increase in the target concentration under any of the four measurement conditions. Thus, it can be said that the target concentration can be detected from aggregation area A. On the other hand, because the error bars become long at many target concentrations, it can be seen that there is room for improvement in optimization of the measurement conditions.

Example 2

<Influence of Flow Velocity of Sample>

Figure 16:
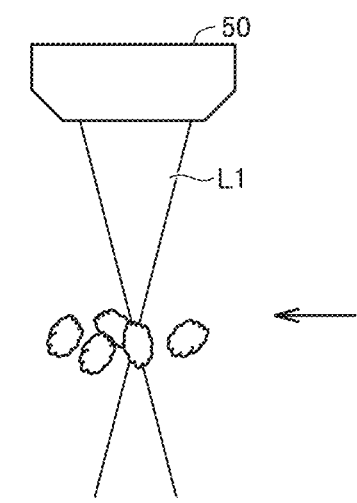
FIG. 16 is a conceptual diagram illustrating an influence of a flow velocity of a sample on aggregation of the latex bead.
Figure 16:
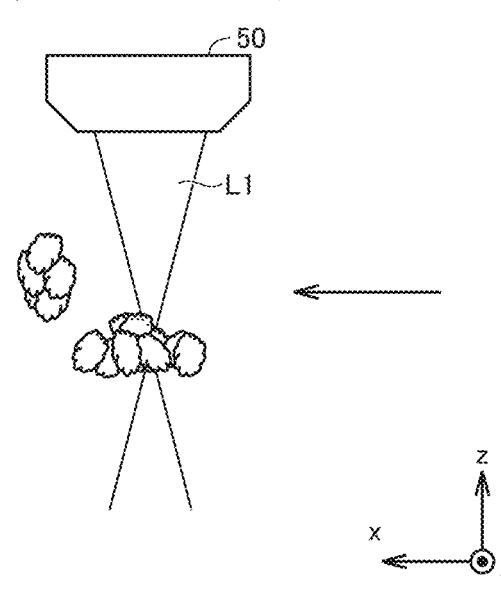

FIG. 16 is a conceptual diagram illustrating an influence of flow velocity V of sample SP on the aggregation of beads B1, B2. Whether beads B1, B2 and analyte X are encountered and bound is a stochastic event. However, when flow velocity V is slow (for example, when V=47.6 [μm/s]), the supply amounts of beads B1, B2 and analyte X per unit time to the beam waist of laser beam L1 are relatively small, so that the encounter probability between beads B1, B2 and analyte X is low. Consequently, there may be the case where beads B1, B2 are bound through analyte X until the light irradiation time of several minutes elapses and the growth of the aggregate proceeds to some extent, or there may be the case where beads B1, B2 cannot be bound much without encountering analyte X and the growth of the aggregate is difficult to proceed (see the upper drawing in FIG. 16). Accordingly, it is considered that the error bar becomes large when flow velocity V is excessively low (V=47.6 [μm/s]).

On the other hand, when flow velocity V is high (for example, when V=476 [μm/s]), supply amounts of beads B1, B2 and analyte X per unit time are relatively large. For this reason, the growth of the aggregates of beads B1, B2 easily proceeds during the light irradiation time of three minutes. However, because the aggregates of beads B1, B2 have large resistance received from the fluid at a high flow velocity, there is a possibility that the aggregates that are being formed may be split (some of the aggregates may be torn off) (see the lower drawing in FIG. 16). Because the size of the split and flowed aggregate varies, the size of the remaining aggregate also varies. Accordingly, it is considered that the error bar becomes large even when flow velocity V is excessively high (V=476 [μm/s]).

For this reason, flow velocity V has an appropriate range depending on, for example, a characteristic of microchannel 92 (such as a shape and hydrophilicity/hydrophobicity of a channel inner wall), characteristics of beads B1, B2 (such as a shape, a size, a concentration, hydrophilicity/hydrophobicity, and charging), and a characteristic of sample SP (such as viscosity of a solvent). Accordingly, desirably flow velocity V is optimized prior to the start of the execution of the antigen detection process. Flow velocity V from syringe pump 30 is adjusted to the optimum flow velocity at which beads B1, B2 specifically bind to analyte X to advance the growth of the aggregates before the start of the distribution of sample SP. Syringe pump 30 that can adjust flow velocity V with high accuracy near a desired value is desirably adopted as will be described later in Example 10 (see FIG. 44).

Example 3

<Influence of Irradiation Direction of Laser Beam>

Next, the measurement result in the case of the upward irradiation with laser beam L1 is compared with the measurement result in the case of the downward irradiation with laser beam L1 (see FIG. 15).

Figure 17:
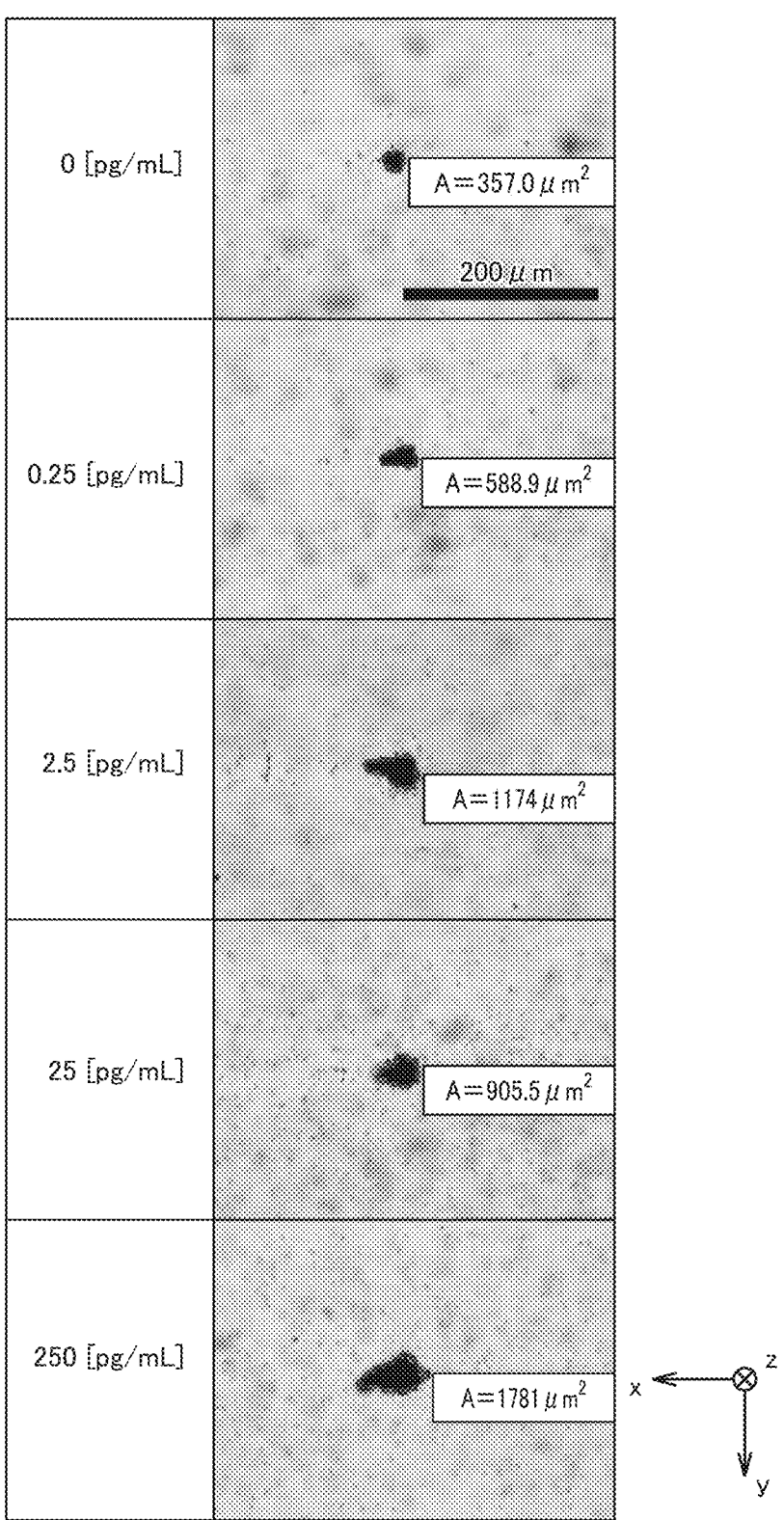
FIG. 17 is a view illustrating an image near a laser spot when the analyte is CD80 and when the detection kit is irradiated with the laser beam from a lower side to an upper side (during upward irradiation).

FIG. 17 is a view illustrating an image near a laser spot when the analyte is CD80 and when detection kit 90 is irradiated with laser beam L1 from the lower side to the upper side (during the upward irradiation). Also in Example 3, objective lens 50 having the magnification of 10 times was used. In addition, the position $z_{top}$ of the beam waist with respect to the upper surface of microchannel 92 was set to 0 μm. Furthermore, flow velocity V of sample SP was set to 119 [μm/s]. The distribution direction of sample SP was the direction from the right side to the left side in the drawing.

Also in the upward irradiation, it was confirmed that aggregation area A of beads B1, B2 tended to increase as the target concentration became higher. It was also found that the shapes of the aggregates of beads B1, B2 were a shape extending in the distribution direction of sample SP.

FIG. 18 is a view that illustrates the relationship between the target concentration and aggregation area A when analyte X is CD80, the relationship being obtained from the image in FIG. 17. FIG. 18 illustrates an average of four measurement results and the error bars. From FIG. 18, it is understood that the correspondence relationship (calibration curve) between the target concentration and aggregation area A can be acquired in the upward irradiation similarly to in the downward irradiation.

During the downward irradiation, the dissipative force of laser beam L1 acts on beads B1, B2 from the upper side to the lower side. Although the specific gravity of beads B1, 2 is about the same as the specific gravity of water (0.98 to 1.04 [g/cm$^3$]), beads B1, B2 forming the aggregates are easily deposited or settled on the bottom surface of microchannel 92. This may cause an error in the calculation result of aggregation area A. Accordingly, for the purpose of preventing the deposition or settlement of beads B1, B2 and removing this error factor, it is conceivable to adopt the upward irradiation instead of the downward irradiation. However, the error bar of aggregation area A obtained by the upward irradiation had the same length as the error bar of aggregation area A obtained by the downward irradiation (see FIG. 15).

Figure 19:
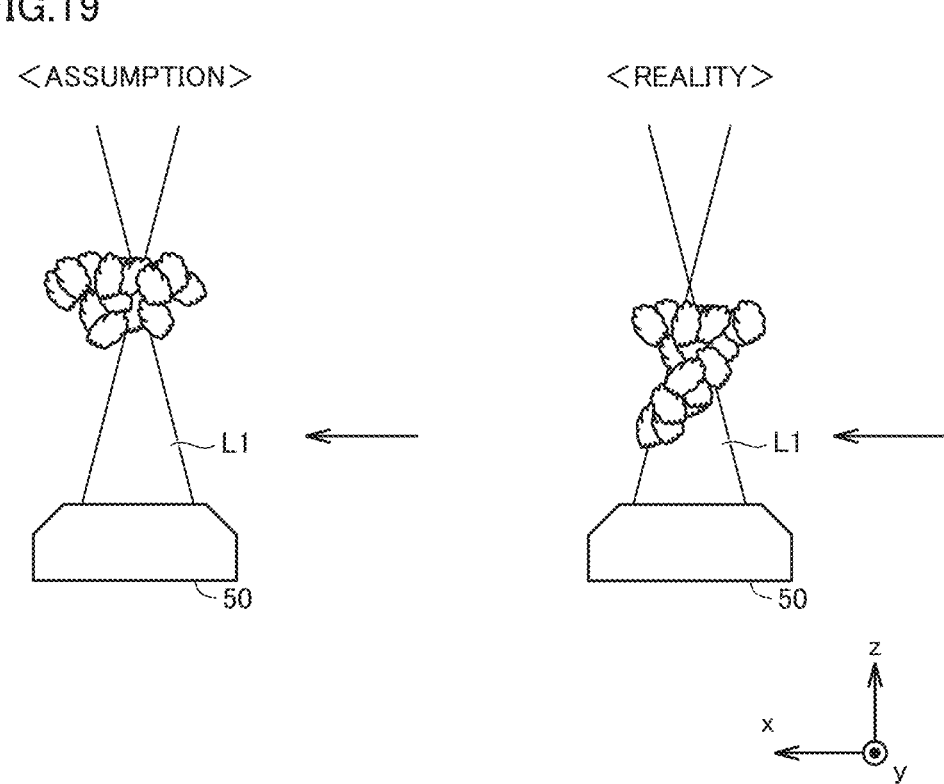
FIG. 19 is a conceptual diagram illustrating a reason why an error is generated in the aggregation area even during the upward irradiation.

FIG. 19 is a conceptual diagram illustrating a reason why the error is generated in aggregation area A even during the upward irradiation. New beads B1 and B2 are supplied to and bound to the aggregates of beads B1, B2 formed at the positions of the beam waist of laser beam L1 along with the distribution of sample SP, whereby the aggregates grow. At this time, due to the influence of gravity, the aggregate hardly extends above the beam waist and easily extends below the beam waist. When the aggregate extends below the beam waist, beads B1, B2 constituting the aggregate overlap each other when the aggregate is observed in the vertical direction. Because the overlapping portion is not reflected in aggregation area A, the error may be generated between the actual size of the aggregate and aggregation area A, and calculation accuracy of aggregation area A may be reduced (for details, see also the description of FIG. 25 described later).

Example 4

<Influence of Magnification of Objective Lens>

The influence of the magnification of objective lens 50 on the aggregates of beads B1, B2 will be described below. Hereinafter, objective lens 50 having the magnifying power of 10 is also referred to as a "10-power magnifying lens", and objective lens 50 having the magnifying power of 40 is also referred to as a "40-power magnifying lens".

Figure 20:
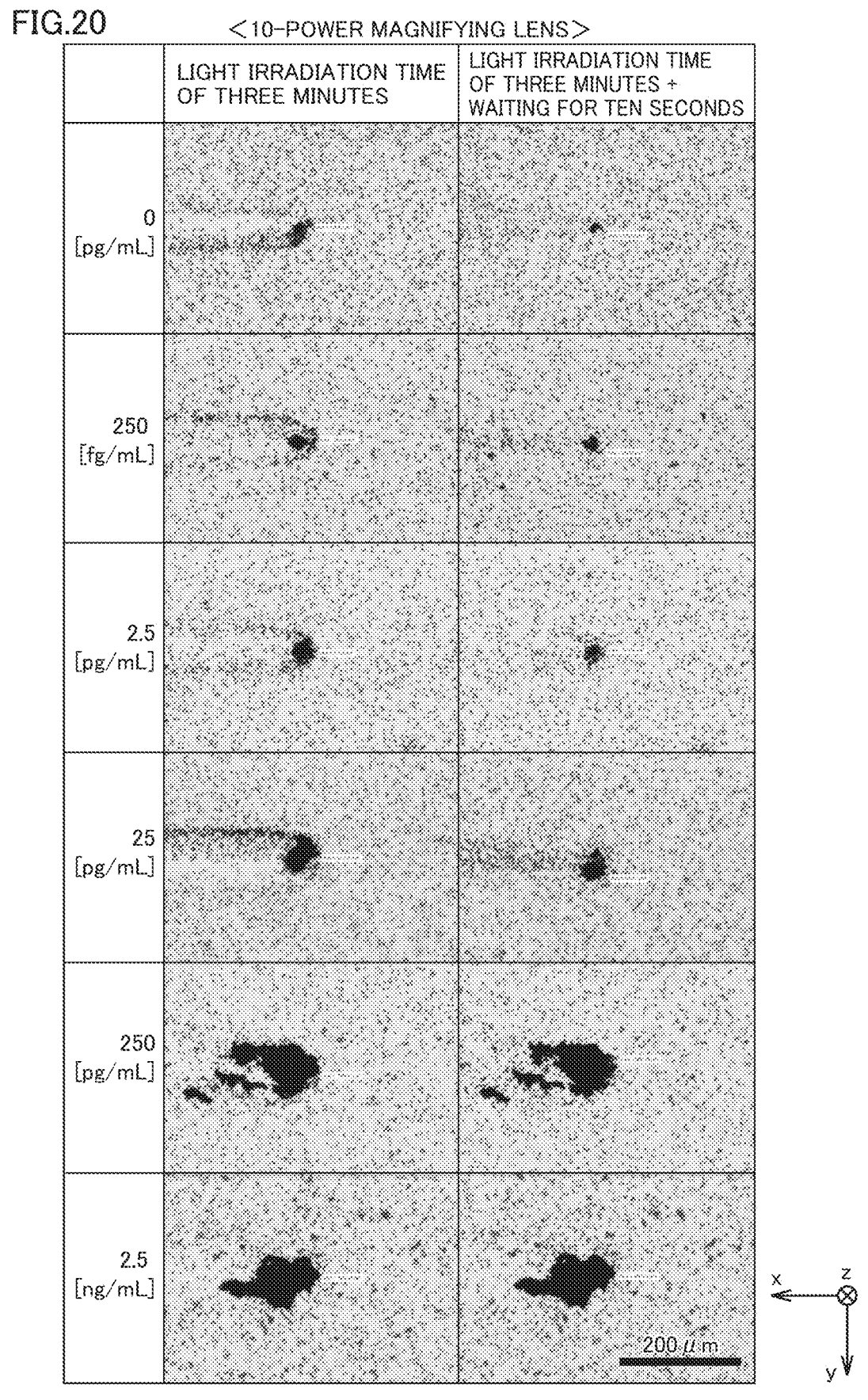
Figure 21:
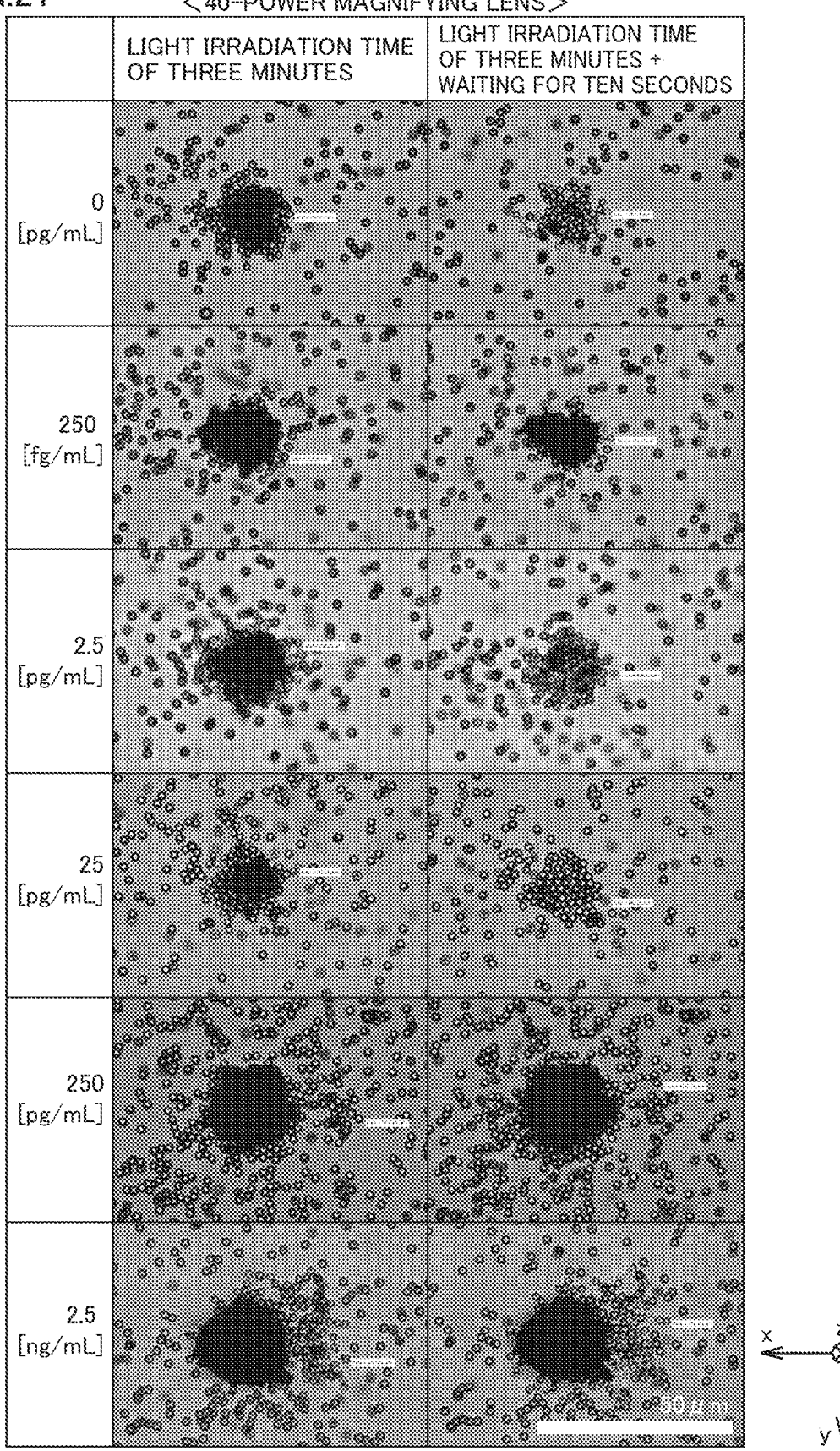
FIG. 21 is a view illustrating an image near the laser spot when the analyte is the CD80 and when a 40-power magnifying lens is used.

FIG. 20 is a view illustrating an image near the laser spot when analyte X is CD80 and when the 10-power magnifying lens is used. FIG. 21 is a view illustrating an image near the laser spot when analyte X is CD80 and when the 40-power magnifying lens is used. FIGS. 20 and 21 illustrate images acquired by the downward irradiation with the target concentration set in 6 ways in the concentration range from 0 [pg/mL] to 2.5 [ng/mL] (=2500 [pg/mL]). In FIGS. 20 and 21, the image on the left side is the image acquired after the irradiation with laser beam L1 for three minutes. The image on the right side is the image acquired when the irradiation with laser beam L1 is stopped after the irradiation with laser beam L1 for three minutes, and then ten seconds elapses.

As illustrated in FIGS. 20 and 21, in the embodiment 1, the aggregates of beads B1, B2 were observed in about three minutes by the light-induced acceleration. That is, the time required for detecting analyte X (CD80) was only about three minutes. Taking onto account that the detection time is about two hours in a method in which the light-induced acceleration is not performed (for example, the ELISA method), it can be seen that the detection time of analyte X is greatly shortened according to the first embodiment.

In addition, when compared under the condition where the target concentrations were equal, it was observed that the size of the aggregates of beads B1, B2 was larger in the case of the 40-power magnifying lens than in the case of the 10-power magnifying lens. The reason is considered as follows. In the case of the 40-power magnifying lens, the electric field intensity and the electric field intensity gradient at the beam waist become stronger by the smaller size of the beam waist compared with the case of the 10-power magnifying lens. Then, the light-induced force (the inter-object light-induced force and the gradient force) acting on beads B1, B2 becomes stronger, and thus beads B1, B2 are easy to aggregate.

Figure 22:
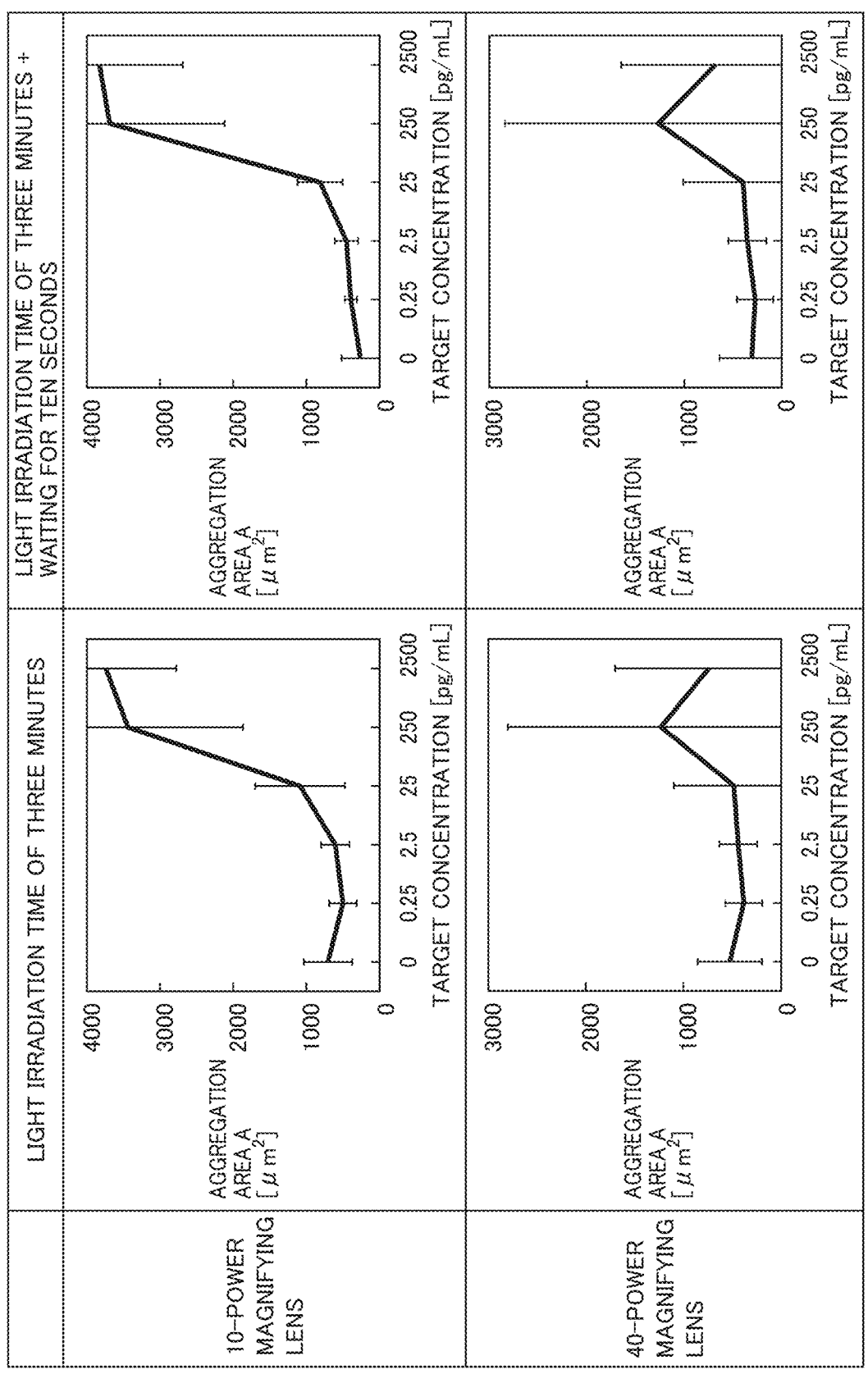
FIG. 22 is a view illustrating the relationship between the target concentration and the aggregation area of the latex bead when the analyte is the CD80, the relationship being obtained from the images in FIGS. 20 and 21.

FIG. 22 is a view illustrating the relationship between the target concentration and aggregation area A of beads B1, B2 when analyte X is the CD80, the relationship being obtained from the images in FIGS. 20 and 21. FIG. 22 illustrates an average of four measurement results and the error bars. The position $z_{btm}$ of the beam waist based on the bottom surface of microchannel 92 was set to 0 μm. Flow velocity V of sample SP was set to 119 [μm/s].

Referring to FIG. 22, in the case of the 10-power magnifying lens, it was observed that aggregation area A of beads B1, B2 tended to increase as the target concentration was higher. However, even when the target concentration increased from 250 [pg/mL] to 2500 [pg/mL], the increase in aggregation area A associated with the increase was relatively small. For this reason, even when the target concentration is increased higher, there is a possibility that aggregation area A is not monotonically increased.

In addition, when a significance test was performed, a two-sided probability of a group with the target concentration of 25 [pg/mL] became 0.011. The two-sided probability was within 0.05 (=5%), a significant difference between the group of 25 [pg/mL] and the group of 2.5 [pg/mL] was confirmed. Accordingly, a detection limit of analyte X (CD80) in Example 4 was estimated to be 2.5 [pg/mL]. Because the detection limit of the ELISA method in which the light-induced acceleration is not performed is about 20 [pg/mL], it can be seen that the detection limit of analyte X in Example 4 is about one order of magnitude lower (that is, the detection sensitivity is one order higher.).

On the other hand, when the 40-power magnifying lens was used, aggregation area A at the target concentration of 2500 [pg/mL] was smaller than aggregation area A at the target concentration of 250 [pg/mL]. In addition, the error bars were very large when the target concentration was 250 [pg/mL] or 2500 [pg/mL]. This is considered that the aggregates of beads B1, B2 grew excessively large due to the use of the 40-power magnifying lens, and as a result, a part of the aggregates of beads B1, B2 is split and flowed in the distribution direction of sample SP.

Example 5

<Concentration Dependency of FDP>

In Examples 5 to 7, concentration measurement results when analyte Y is the fibrinogen and fibrin degradation product (FDP) will be described. As described in FIG. 3, bead B3 modified with one kind of anti-FDP antibody is used for the detection of analyte Y (FDP).

Figure 23:
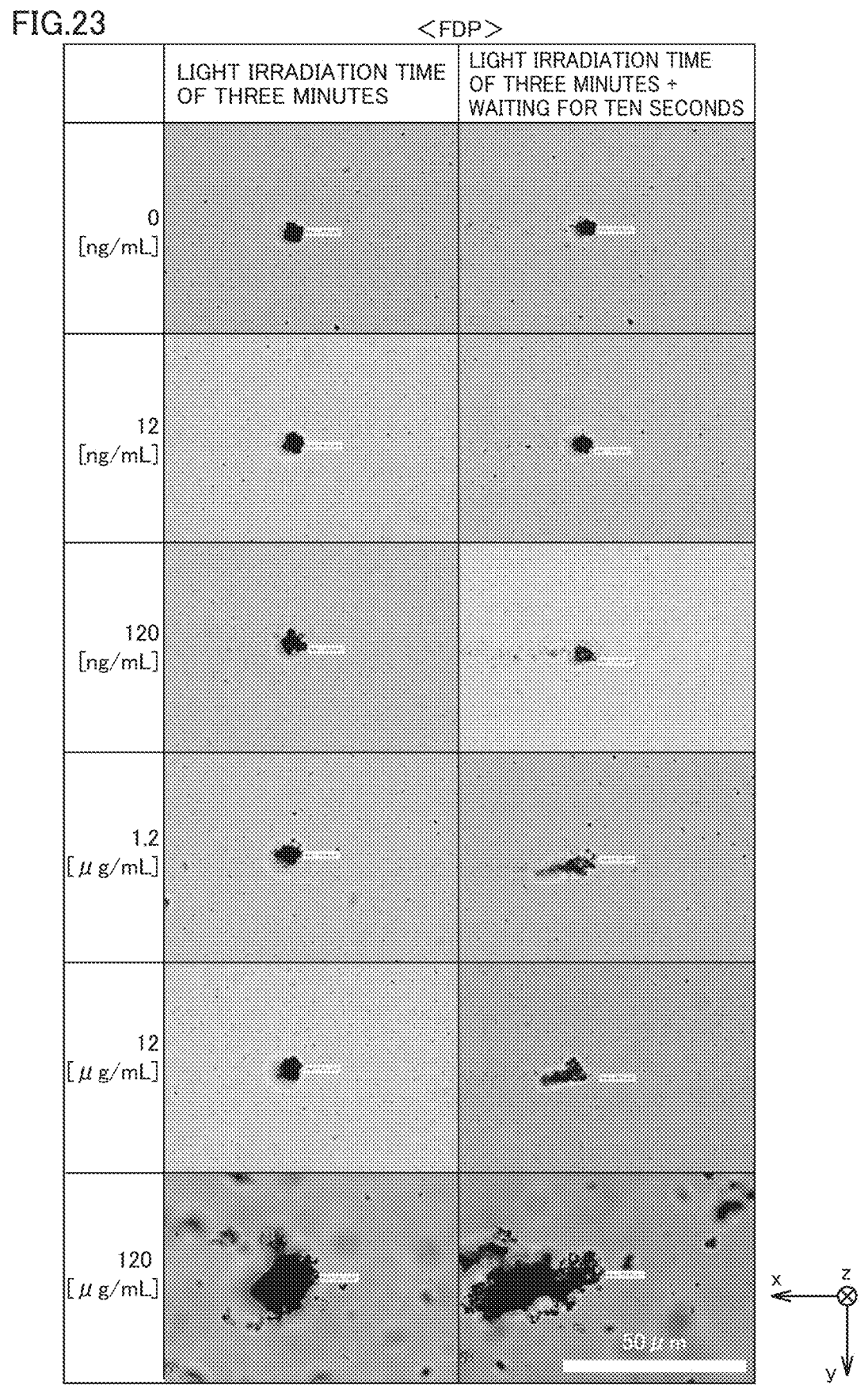
Figure 26:
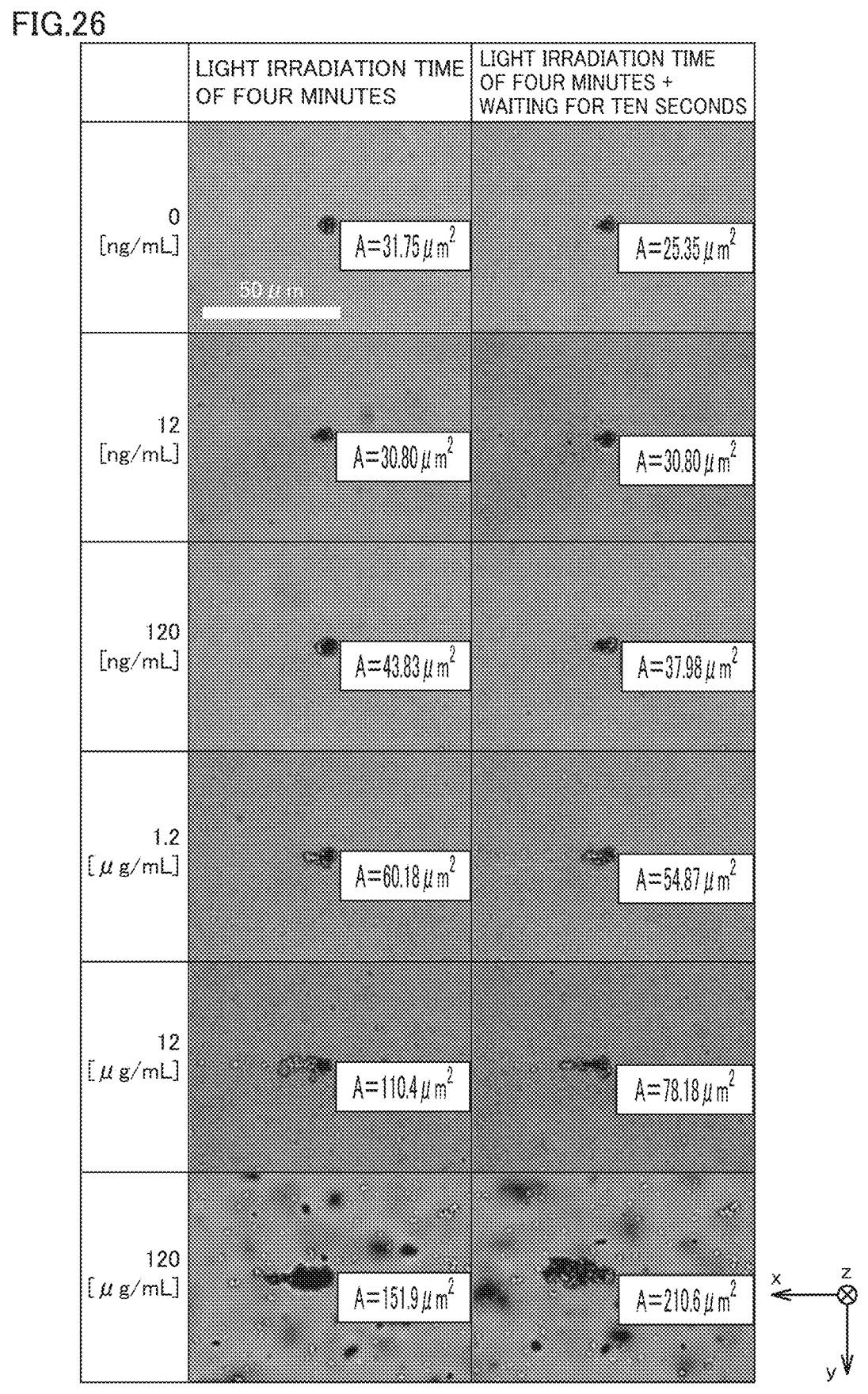

FIG. 23 is a view illustrating an image near the laser spot in Example 2 where analyte Y is the FDP. FIG. 23 and FIG. 26 described later illustrate the images acquired at each target concentration when the concentration (target concentration) of analyte Y is set to six ways in the concentration range of 0 [ng/mL] to 120 [pg/mL]. The left side of FIG. 23 illustrates the image acquired after the downward irradiation with laser beam L1 for three minutes. The right side illustrates the image acquired when the irradiation with laser beam L1 is stopped after the downward irradiation with laser beam L1 for three minutes and ten seconds elapse.

As illustrated in FIG. 23, when analyte Y was the FDP, the aggregate of beads B3 were confirmed.

Figure 24:
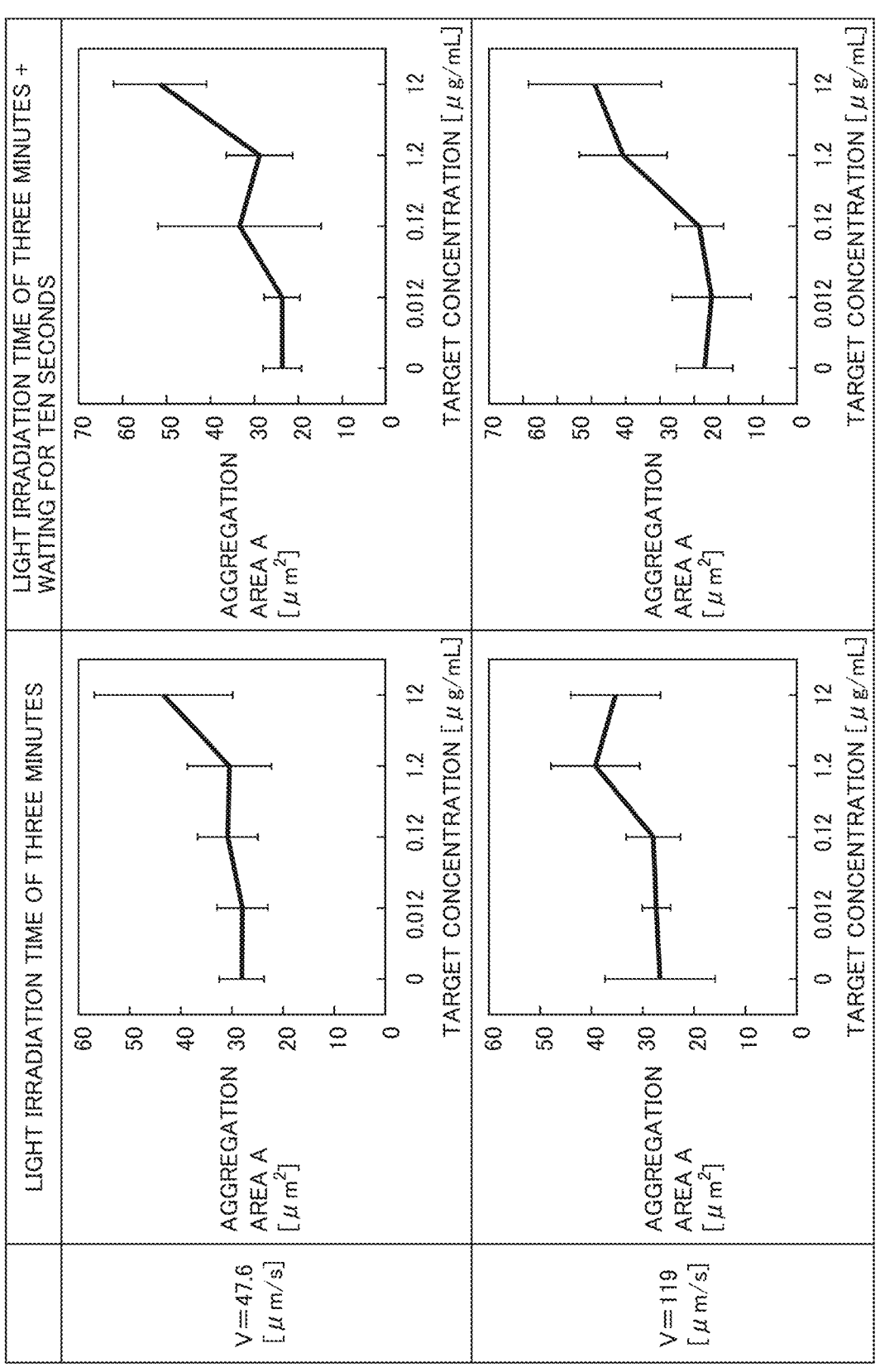
FIG. 24 is a view illustrating the relationship between the target concentration and the aggregation area of the latex bead when the analyte is the FDP.

FIG. 24 is a view illustrating the relationship between the target concentration and aggregation area A of bead B3 when analyte Y is the FDP. In the example, in the downward irradiation, flow velocity V of sample SP was set in two ways (V=47.6 [μm/s], 119 [μm/s]). In addition, the case of the standby for ten seconds after the irradiation with laser beam L1 for three minutes was compared with the case of not the standby for ten seconds. The error bar represents a measurement error when the measurement is performed four times under each measurement condition.

Referring to FIG. 24, under any measurement condition, aggregation area A when the target concentration is 12 [μg/mL] is different from aggregation area A when the target concentration is less than or equal to 0.12 [μg/mL] (=120 [ng/mL]). Accordingly, it can be seen that when the target concentration is 12 [μg/mL], analyte Y can be detected regardless of the measurement condition.

Among them, as illustrated in the lower right view, when flow velocity V is set to 119 [μm/s] and when the standby is performed for ten seconds after the irradiation with laser beam L1 for three minutes, there is a possibility that analyte Y can be detected even when the target concentration is 1.2 [μg/mL]. As described above, by providing the standby time of 10 seconds after the irradiation with laser beam L1 is stopped, there is a possibility that the detection accuracy of analyte Y is improved to widen the range of the detectable concentration of analyte Y (the detection limit is lower concentration) as compared with the case where the standby time is not provided (see the lower left view).

Example 6

<Setting of Standby Time>

Figure 25:
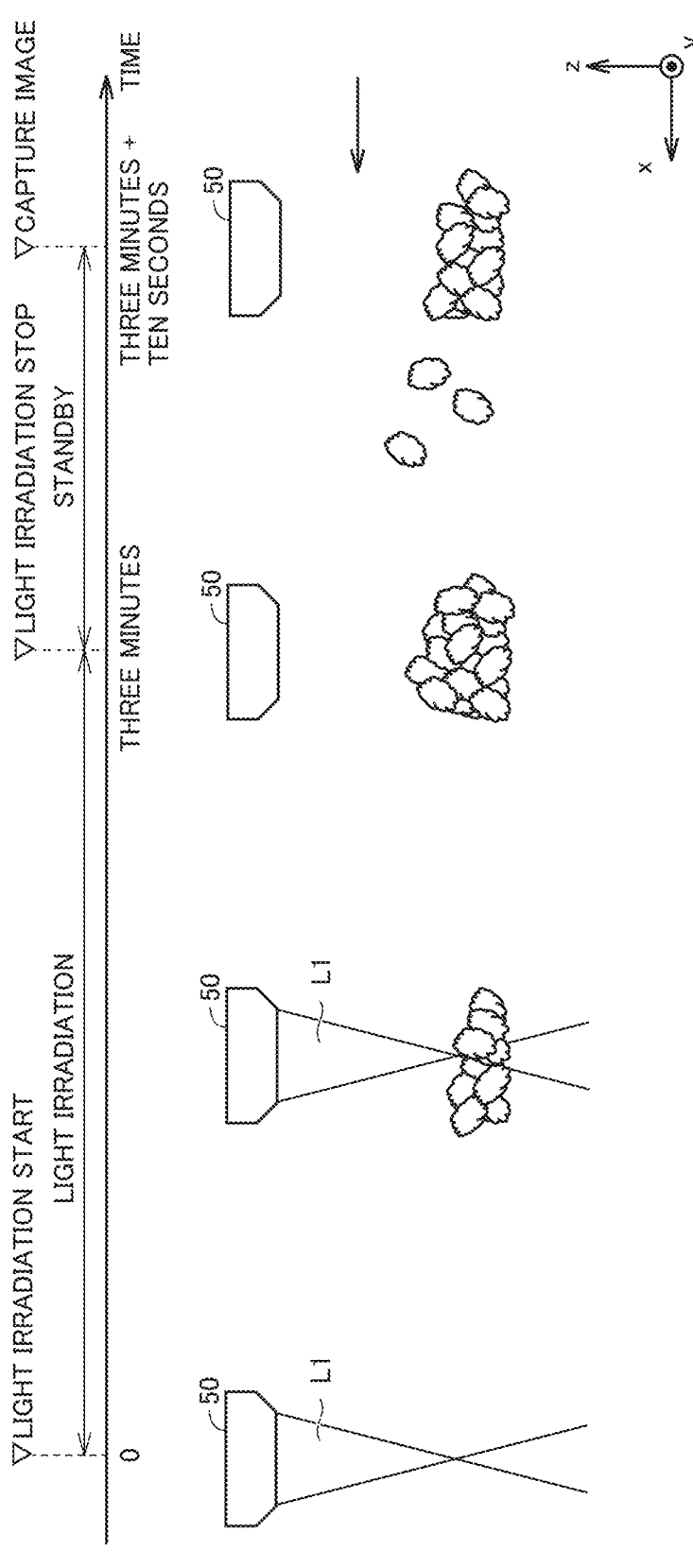
FIG. 25 is a conceptual diagram illustrating meaning of provision of standby time after stop of the irradiation with the laser beam.

FIG. 25 is a conceptual diagram illustrating meaning of provision of the standby time after stop of the irradiation with the laser beam L1. The reason why the detection accuracy of analyte Y is improved by providing the standby time is considered to be the following two points.

First, after the start of the irradiation with laser beam L1, the growth of aggregate of bead B3 progresses with the lapse of time. At a time point when three minutes elapse after the start of the irradiation with laser beam L1, there is bead B3 that is captured near the beam waist by the light-induced force of laser beam L1 but is not bound to the aggregate of beads B3. The amount of such unbound beads B3 varies greatly from measurement to measurement. Accordingly, unbound beads B3 can be an error factor in calculating aggregation area A. By providing the standby time after the irradiation with laser beam L1 is stopped, unbound bead B3 flows in the distribution direction of sample SP, so that the error factor is reduced.

Second, the parameter directly correlated with the target concentration is a three-dimensional size (volume) of the aggregate of bead B3. However, it is difficult to capture the three-dimensional shape of the aggregate with one camera 60. For this reason, instead of the size of the aggregate of bead B3, aggregation area A that is the area obtained by projecting the aggregate on a horizontal plane is used for quantification of the target concentration. Here, the aggregate of bead B3 has portions overlapping each other in the vertical direction (z-direction), but the overlapping portion is not captured by camera 60. Accordingly, the size of the overlapping portion is not reflected in aggregation area A, and there is a possibility that the correspondence between the size of the aggregate and aggregation area A is degraded. During the standby period, the overlapping portion extends in the distribution direction (x-direction) of sample SP as compared with immediately after the irradiation with laser beam L1 is stopped, so that the overlapping portion is reduced. As a result, the correspondence between the size of the aggregate of bead B3 and aggregation area A can be improved.

For the above two reasons, the target concentration can be more accurately quantified from aggregation area A of bead B3 by providing the standby time.

Example 7

<Irradiation Direction Dependency and Influence of Light Irradiation Time>

FIG. 26 is a view illustrating the relationship between the target concentration and aggregation area A of bead B3 during the upward irradiation when analyte Y is the FDP. The left side of FIG. 26 illustrates the image acquired after the irradiation with laser beam L1 for four minutes. The right side illustrates the image acquired when the irradiation with laser beam L1 is stopped after the irradiation with laser beam L1 for four minutes and then ten seconds elapse.

Figure 27:
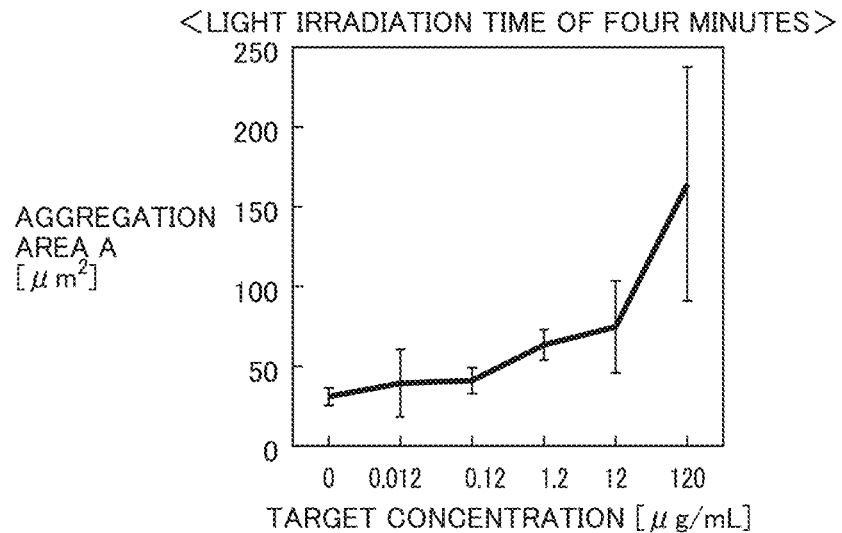
FIG. 27 is a view illustrating the relationship between the target concentration and the aggregation area of the latex bead when the analyte is FDP, the relationship being obtained from the image in FIG. 26.
Figure 27:
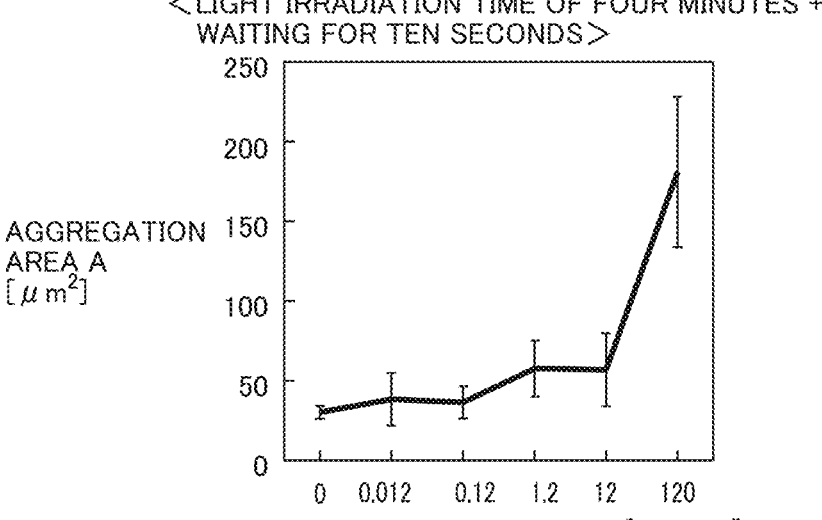

FIG. 27 is a view illustrating the relationship between the target concentration and aggregation area A of bead B3 when analyte Y is FDP, the relationship being obtained from the image in FIG. 26. Referring to FIG. 27, in the upward irradiation, the length of the error bar in the case where the standby time was provided after the irradiation with laser beam L1 (see the lower view) was about the same as the length of the error bar in the case where the standby time was not provided (see the upper view). From this, it can be seen that the effect of providing the standby time during the upward irradiation is small unlike the downward irradiation (see FIG. 24).

Furthermore, comparing FIG. 24 with FIG. 27, the error bar at each target concentration was shortened by increasing the irradiation time of laser beam L1 from three minutes to four minutes. Thus, it can be seen that the optimization of the irradiation time of laser beam L1 is required as part of the optimization of the measurement condition.

Example 8

<Defocus Condition>

Results of the light-induced acceleration performed under the condition that the beam waist of laser beam L1 deviates from microchannel 92 when analyte X is the CD80 or the CD9/CD63 complex epitope will be described in Examples 8, 9. Hereinafter, this condition is also referred to as a "defocus condition".

Figure 28:
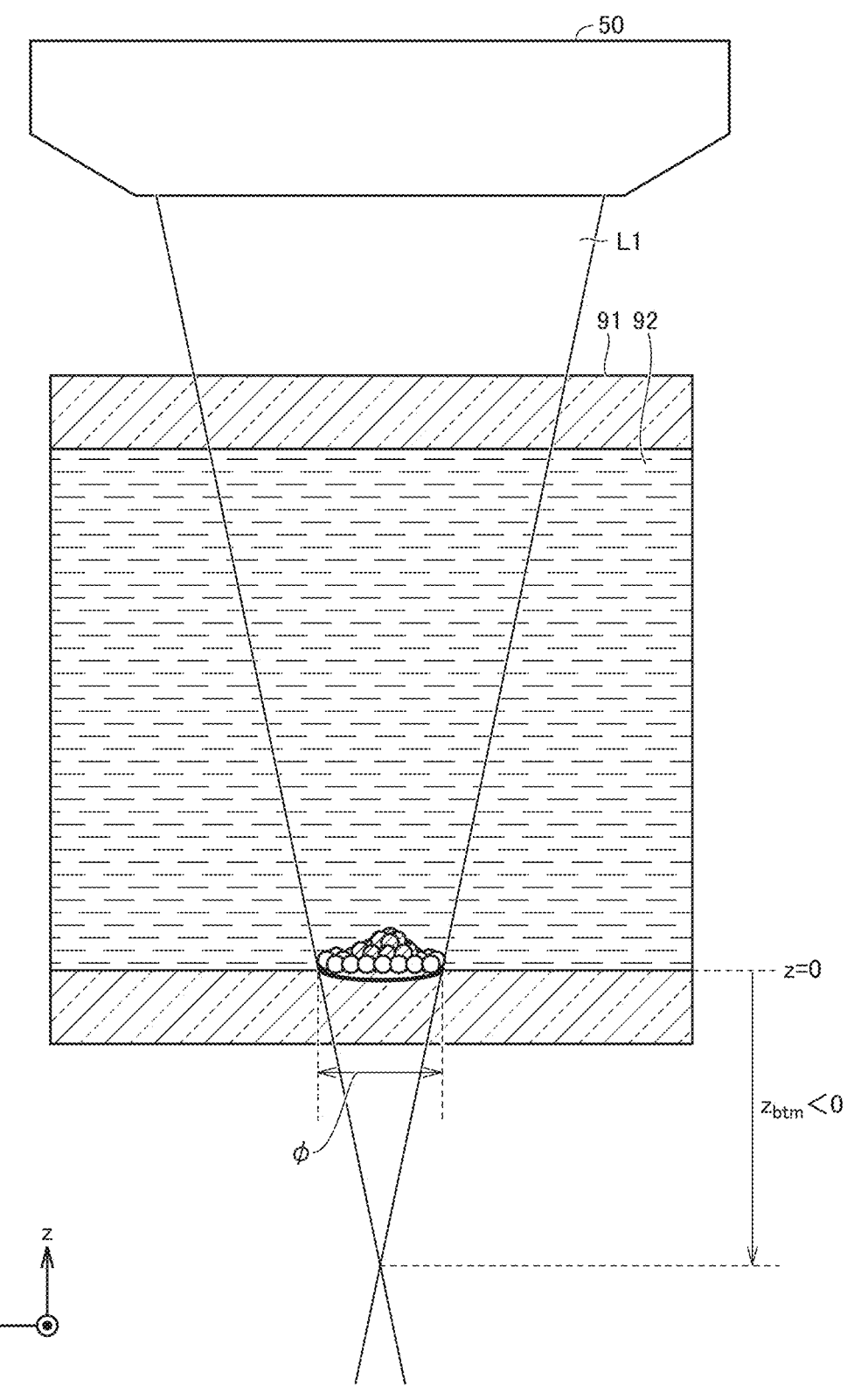
FIG. 28 is a view illustrating a defocus condition.

FIG. 28 is a view illustrating the defocus condition. Referring to FIG. 28, the defocus condition is more specifically a condition that the beam waist of laser beam L1 is located behind microchannel 92 in the irradiation direction of laser beam L1. FIG. 28 illustrates the condition that the beam waist is located below the bottom surface of microchannel 92 in the downward irradiation. This condition can be paraphrased as a condition that the position $z_{btm}$ of the beam waist becomes negative when the bottom surface of microchannel 92 is set to the reference (z=0).

Figure 29:
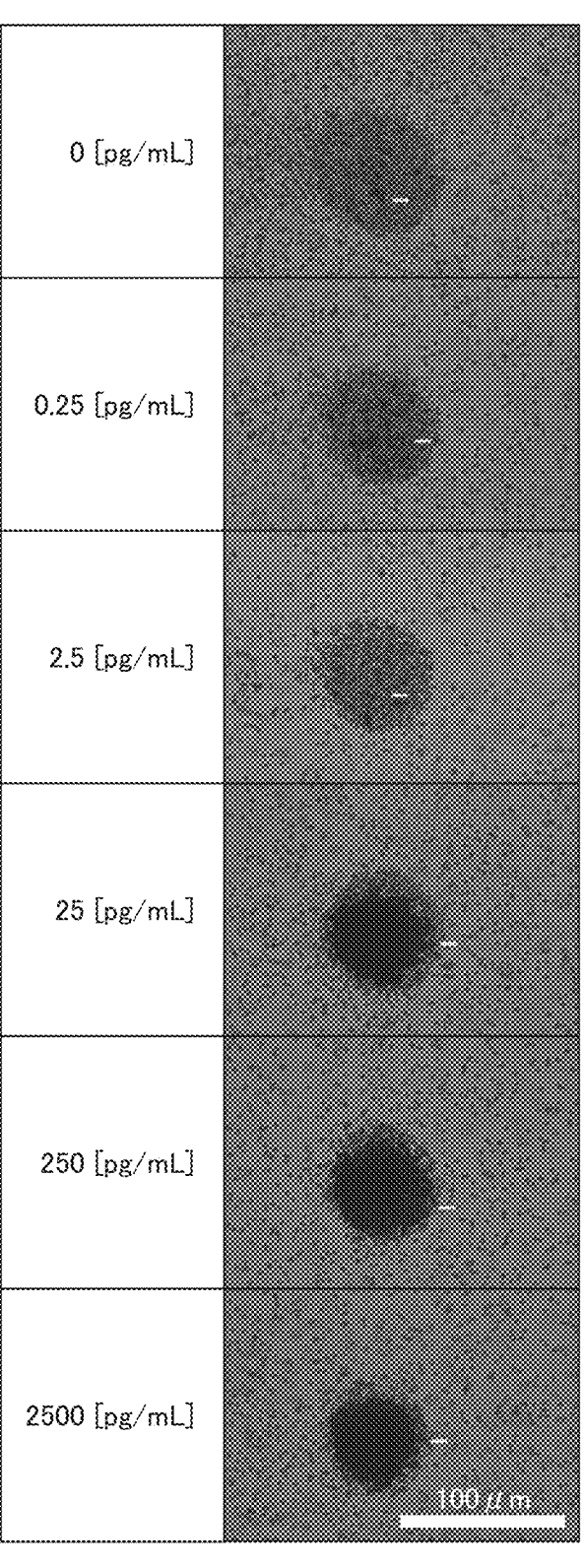
FIG. 29 is a view illustrating an image of the aggregates generated on a bottom surface of a microchannel under the defocus condition when the analyte is the CD80.
Figure 29:
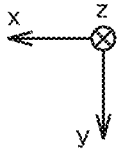

FIG. 29 is a view illustrating an image of the aggregate generated on the bottom surface of microchannel 92 under the defocus condition when analyte X is the CD80. The beam waist was adjusted downward by 65 μm from the bottom surface of microchannel 92 ($z_{btm}$=−65 μm). The laser output after the transmission through the 40-power magnifying lens was 0.53 W. Flow velocity V of sample SP was set to 119 [μm/s].

As illustrated in FIG. 29, when the target concentration was relatively high (particularly, when the target concentration was greater than or equal to 25 [pg/mL]), a region where the color of the image was relatively light (hereinafter, also referred to as a "light color region") was set as an outline, and the existence of a region where the color of the image was relatively deep (hereinafter, also referred to as a "deep color region") could be confirmed. On the other hand, the light color region could be confirmed even when the target concentration was extremely low (when the target concentration was less than or equal to 2.5 [pg/mL]). This means that the aggregation of beads B1, B2 occurs even when the target concentration is low.

Figure 30:
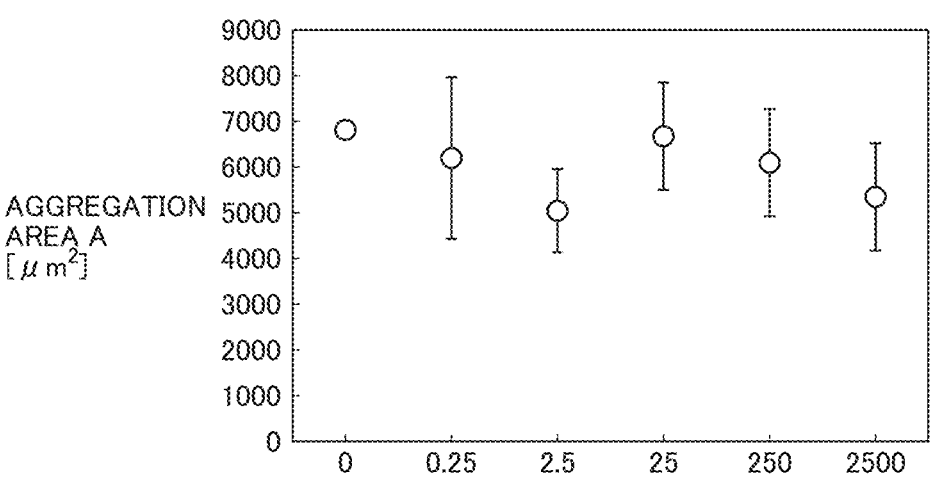
FIG. 30 is a view illustrating the relationship between the target concentration and the aggregation area under the defocus condition.

FIG. 30 is a view illustrating the relationship between the target concentration and aggregation area A under the defocus condition. Under the defocus condition, unlike the measurement results under the focus condition described above (the condition that the beam waist of laser beam L1 is located in microchannel 92), the proportional tendency that aggregation area A of beads B1, B2 increases with increasing target concentration was not confirmed. This is considered to be due to the aggregation mechanism of beads B1, B2 specific to the defocus condition.

Figure 31:
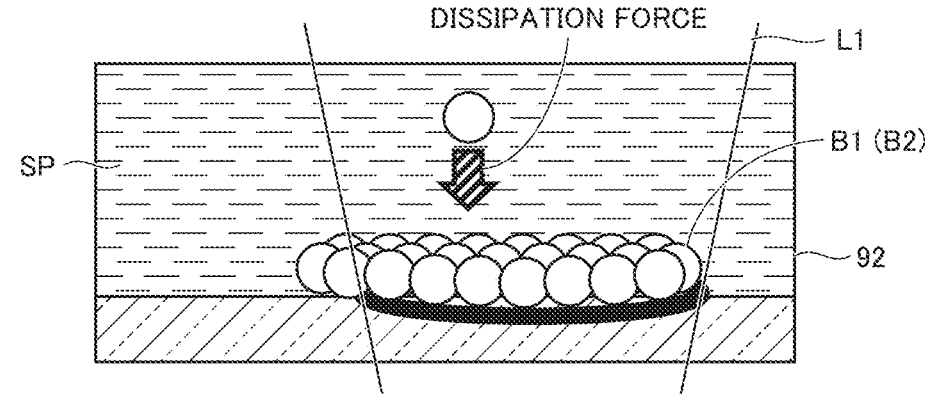
FIG. 31 is a view illustrating an aggregation mechanism of the latex bead under the defocus condition.
Figure 31:
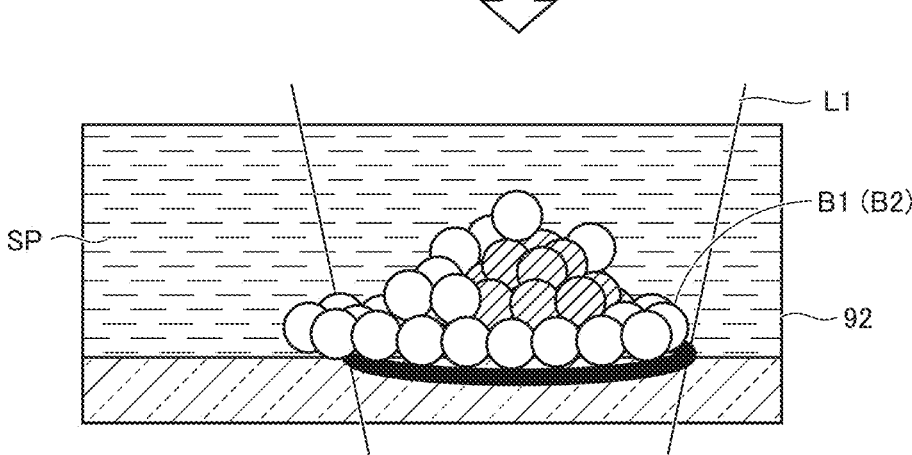
Figure 31:
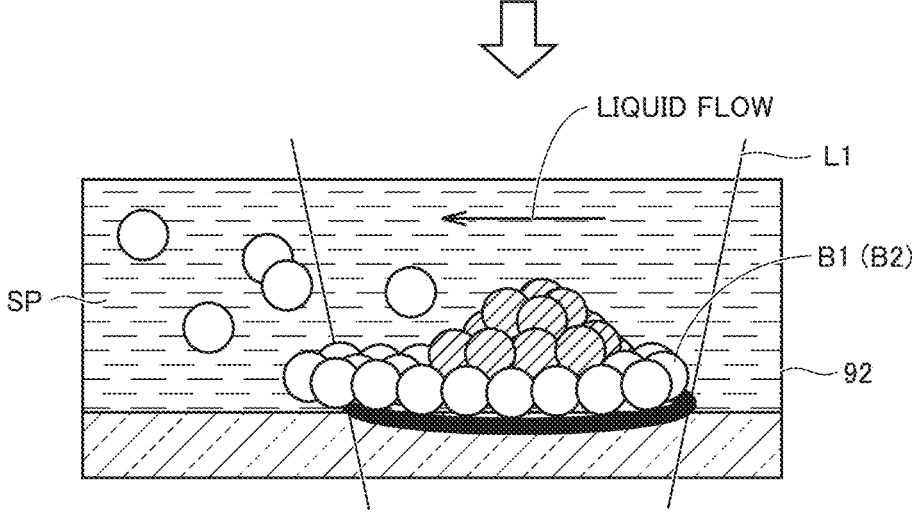

FIG. 31 is a view illustrating the aggregation mechanism of beads B1, B2 under the defocus condition. In FIG. 31, laser beam L1 (laser spot) on the bottom surface of microchannel 92 is indicated by a black circle.

Beads B1, B2 irradiated with laser beam L1 are pressed against the bottom surface of microchannel 92 by the light-induced force (in particular, dissipative force) of laser beam L1. Thus, beads B1, B2 are arranged in a single layer on the bottom surface of microchannel 92 (see the upper view). When other beads B1, B2 are further pressed onto the single layer, a multilayer structure of beads B1, B2 is formed (see the middle view). However, beads B1, B2 that are not bound through analyte X are washed away in the distribution direction of sample SP (see the lower drawing). As a result of such what is called a "washing effect", a region where the multilayer structure of beads B1, B2 bound through analyte X is formed remains. The deep color region in FIG. 29 is considered to be a region where the multilayer structure of beads B1, B2 is maintained as a result of the antigen-antibody reaction.

As described above, the deep color region is a region depending on the amount of beads B1, B2 bound through analyte X. On the other hand, the light color region is basically a region determined according to the size of the laser spot regardless of whether beads B1, B2 are bound through analyte X. Accordingly, under the defocus condition, the target concentration can be quantified with high accuracy using the area of the deep color region instead of aggregation area A in which gradation of the image is not distinguished.

In Example 8, the area of the deep color region is normalized for convenience. Specifically, the ratio of the area of the deep color region to the area of the light color region (the total area in the outline in which the color of the image is light) is defined as a "multilayer ratio".

$$\text{Multilayer ratio=area of deep color region/total area}$$

Figure 32:
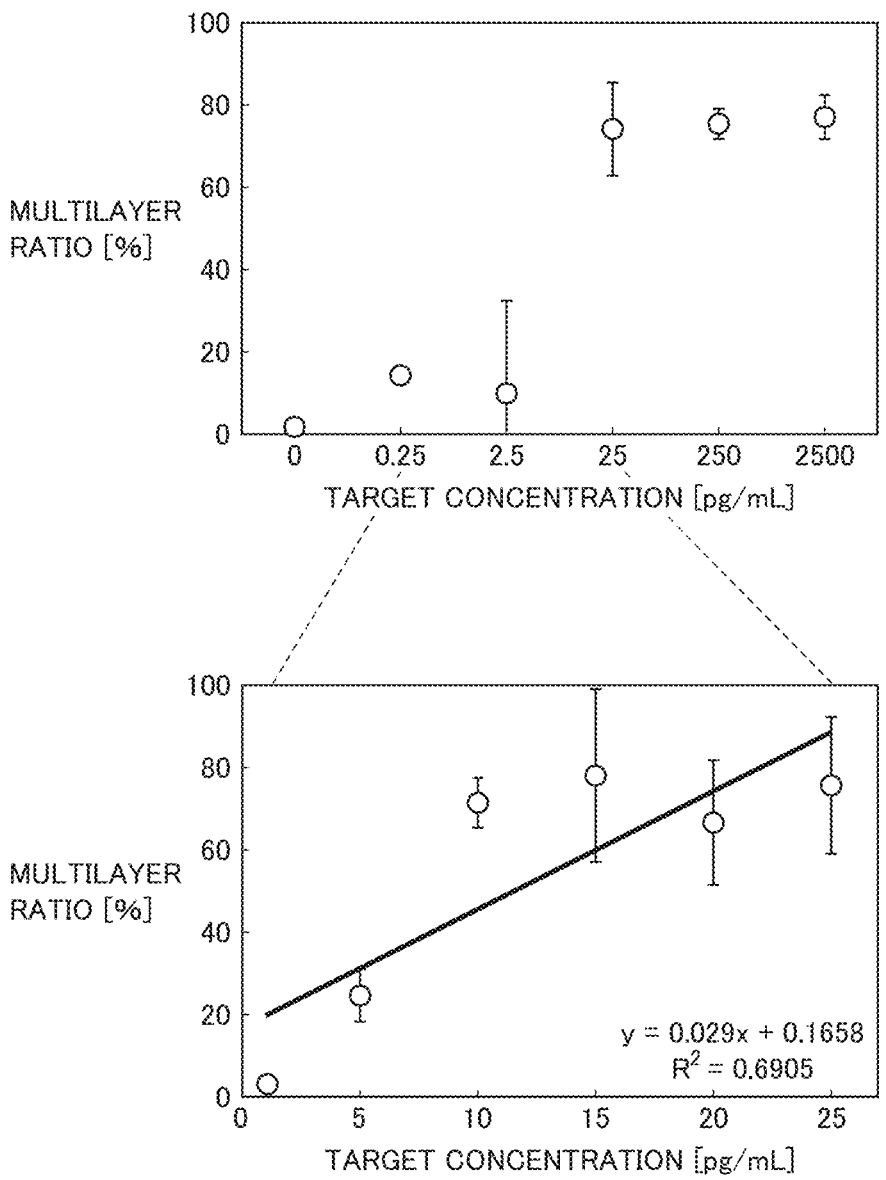
FIG. 32 is a view illustrating a relationship between the target concentration and a multilayer ratio under the defocus condition.

FIG. 32 is a view illustrating a relationship between the target concentration and the multilayer ratio under the defocus condition. In FIG. 32, the horizontal axis represents the target concentration and the vertical axis represents the multilayer ratio. The same holds true for FIG. 33 and the like described later.

As illustrated in the upper part of FIG. 32, a clear difference was confirmed between the target concentrations of 2.5 [pg/mL] and 25 [pg/mL]. Accordingly, the result of the measurement of the target concentrations between 2.5 [pg/mL] and 25 [pg/mL] at intervals of 5 [pg/mL] in more detail is illustrated in the lower part of FIG. 32. As illustrated in the lower part of FIG. 32, under the defocus condition, the proportional tendency that the multilayer ratio increased with increasing target concentration was confirmed in the concentration range of 1 [pg/mL] to 10 [pg/mL]. This result suggests the possibility that the target concentration can be detected even in the order of several [pg/mL], which is one order of magnitude lower than that in the conventional detection method such as the ELISA method.

Figure 33:
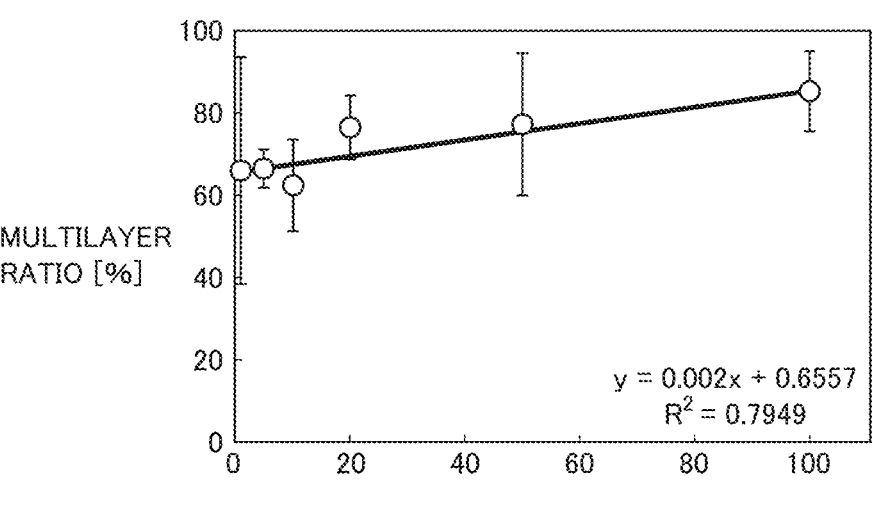
FIG. 33 is a view illustrating the relationship between the target concentration and the multilayer ratio under the defocus condition when the analyte is a CD9/CD63 complex epitope.

FIG. 33 is a view illustrating the relationship between the target concentration and the multilayer ratio under the defocus condition when analyte X is the CD9/CD63 complex epitope. The measurement conditions were common to the case where analyte X was the CD80 described with reference to FIG. 29.

Referring to FIG. 33, the proportional relationship between the target concentration and the multilayer ratio could be confirmed in a wide range of target concentrations. However, when the target concentration was extremely low, the measurement error was large as indicated by the large error bar. The binding force (affinity) between the CD9/CD63 complex epitope and beads B1, B2 is considered to be weaker than the binding force between the CD80 and beads B1, B2.

Example 9

<Relationship Between Channel Width and Irradiation Spot Diameter>

The relationship between the width of microchannel 92 and the diameter of the laser spot in microchannel 92 was optimized in order to reduce the measurement error when the target concentration is extremely low. Hereinafter, sometimes the width of microchannel 92 is abbreviated as a "channel width W". Furthermore, the diameter of the laser spot on the bottom surface of microchannel 92 is described as an "irradiation spot diameter φ", and distinguished from a "minimum spot diameter $\varphi_0$" that is the diameter of the laser spot in the beam waist. In Example 9, three kinds of detection kits 90 having different channel widths W were prepared, and the light-induced acceleration was measured under the downward irradiation condition. The three types of microchannels 92 are referred to as first to third microchannels.

Figure 34:
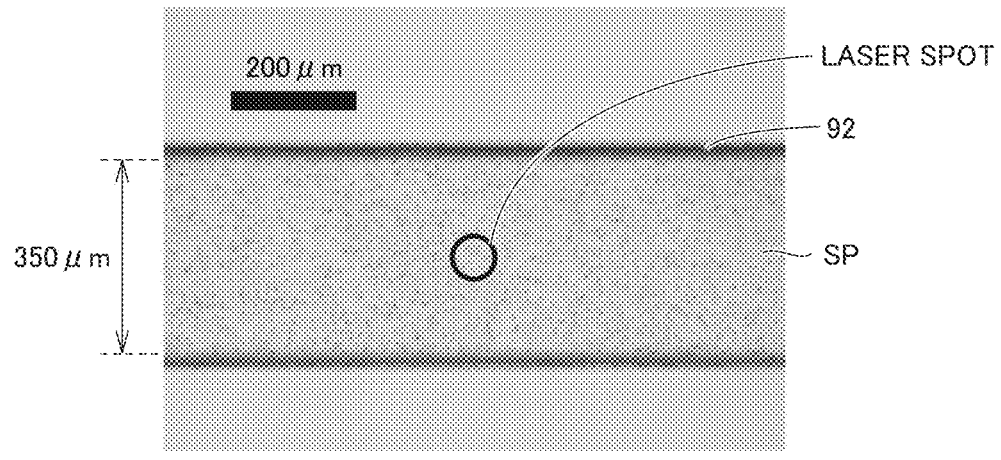
FIG. 34 is an image obtained by capturing three kinds of detection kits.
Figure 34:
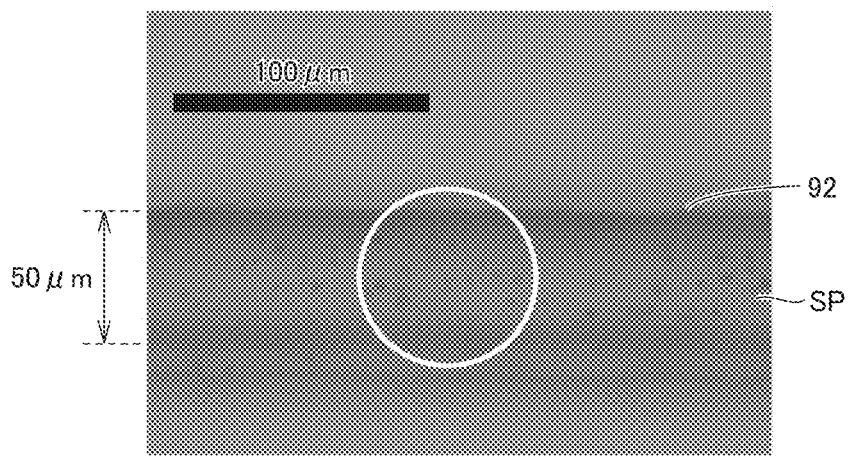
Figure 34:
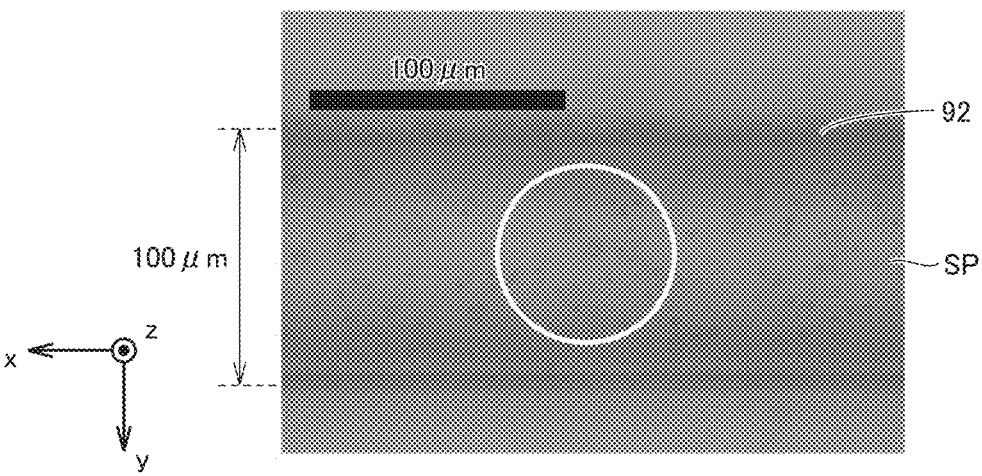

FIG. 34 is an image obtained by capturing three kinds of detection kits 90. FIG. 34 illustrates the first to third microchannels in order from the top. Each microchannel has a rectangular (including square) shape. Channel width W of the first microchannel was 350 μm. Channel width W of the second microchannel was 50 μm. Channel width W of the third microchannel was 100 μm. A circle described in the center of each image represents the size (irradiation spot diameter φ) of the laser spot on the bottom surface of microchannel 92.

Figure 35:
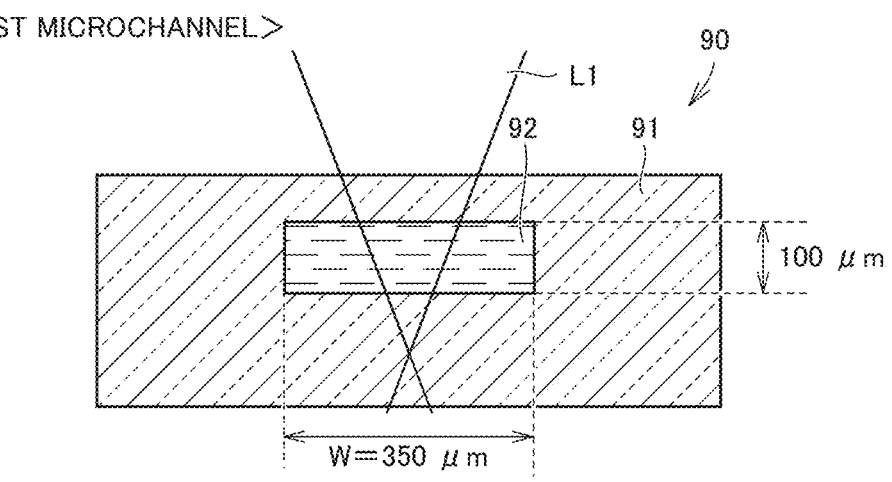
FIG. 35 is a sectional view of the three types of detection kits.
Figure 35:
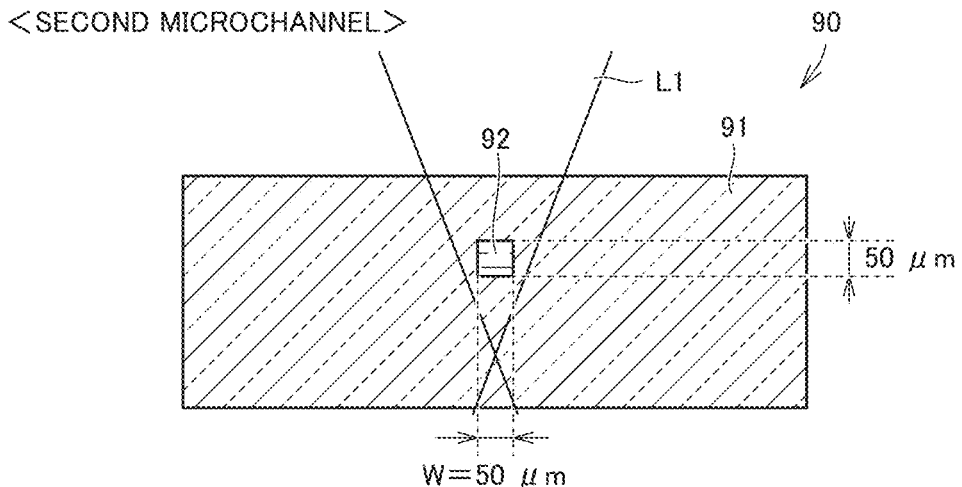
Figure 35:
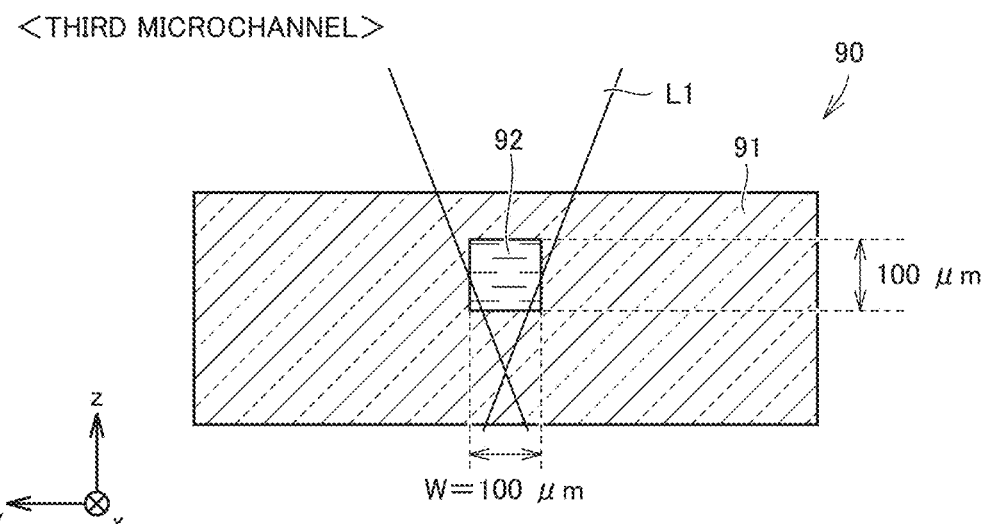
Figure 36:
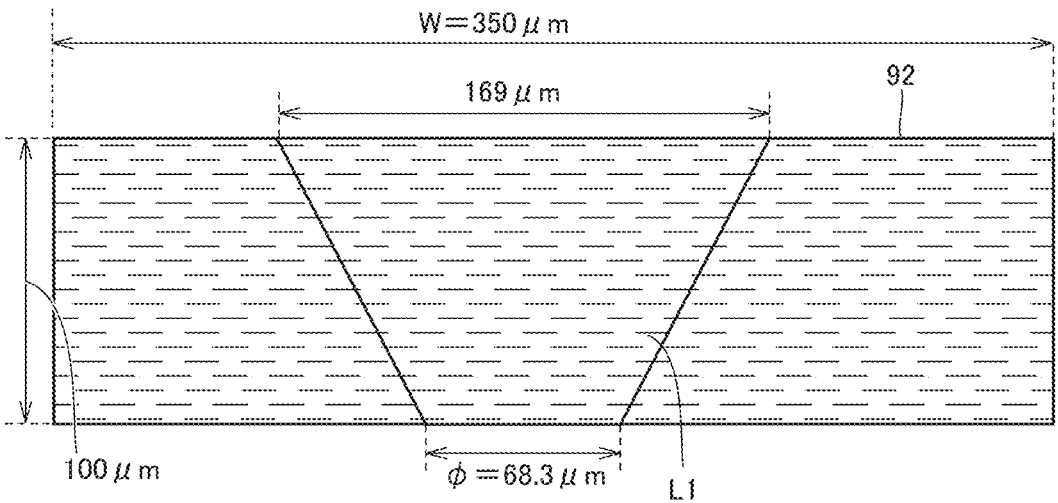
FIG. 36 is an enlarged sectional view illustrating a relationship between a channel width and an irradiation spot diameter for each of first to third microchannels.
Figure 36:
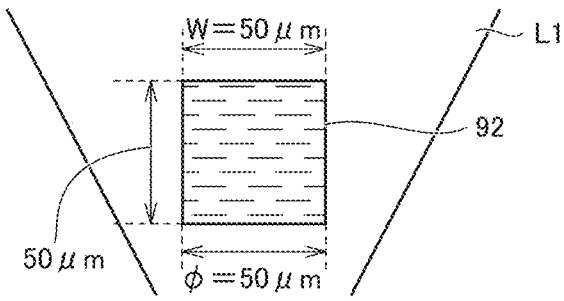
Figure 36:
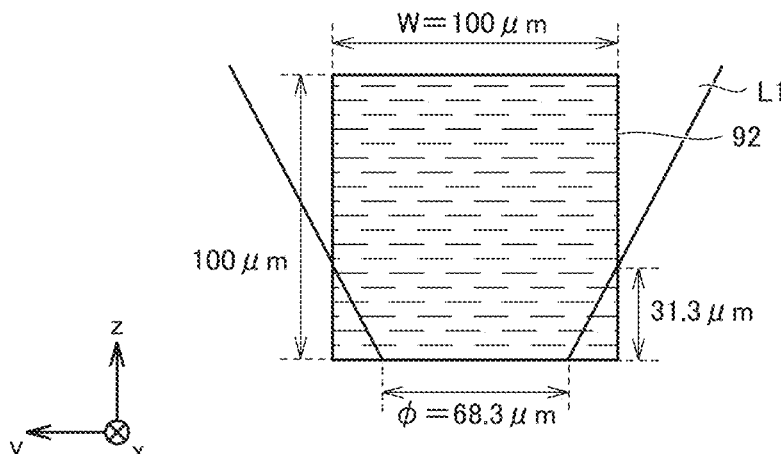

FIG. 35 is a sectional view of the three types of detection kits 90. FIG. 36 is an enlarged sectional view illustrating the relationship between channel width W and irradiation spot diameter φ for each of the first to third microchannels. Referring to FIGS. 35 and 36, in the first microchannel, irradiation spot diameter φ was 68.3 μm for channel width W of 350 μm. In this case, because channel width W is significantly larger than irradiation spot diameter φ, only a part of the section of the first microchannel (specifically, about 34% of the sectional area) is irradiated with laser beam L1.

In the second microchannel, irradiation spot diameter φ was 50 μm with respect to channel width W of 50 μm. Accordingly, in the second microchannel, the entire section is irradiated with laser beam L1.

In the third microchannel, irradiation spot diameter φ was 68.3 μm with respect to channel width W of 100 μm. This measurement is performed under the downward irradiation condition in which the laser spot becomes smaller toward the lower side, and the entire upper surface of microchannel 92 is irradiated with laser beam L1. Considering this point, it can be said that channel width W and the size of the laser spot are about the same. Almost the entire section of the third microchannel (specifically, about 95% of the sectional area) is irradiated with laser beam L1, but there is a small area that is not irradiated with laser beam L1 (remaining about 5%).

As a result of studies by the present inventors, it has become clear that highly efficient aggregation and highly accurate quantification can be achieved when the region that is not irradiated with laser beam L1 remains locally like the third microchannel. The reason can be described as follows. First, in the first microchannel, channel width W is significantly larger than the size of the laser spot. For this reason, the ratio of beads B1, B2 passing through the laser spot without being irradiated with laser beam L1 is high. Accordingly, there is room for improving the aggregation efficiency of beads B1, B2. On the other hand, in the second or third microchannel, because the entire or substantially the entire section is irradiated with laser beam L1, beads B1, B2 are easy to aggregate. The present inventors have found that high quantitative accuracy can be achieved particularly using the third microchannel in the second and third microchannels.

Figure 37:
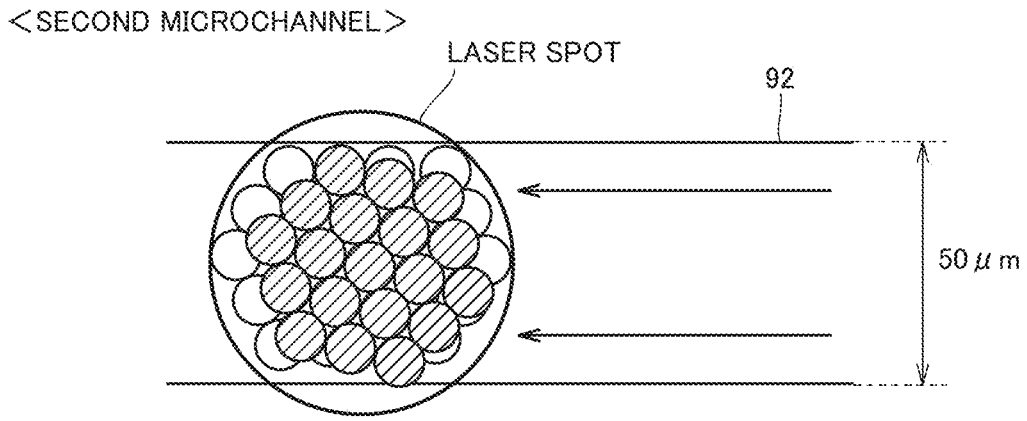
FIG. 37 is a view illustrating a difference in a mechanism between the second microchannel and the third microchannel.
Figure 37:
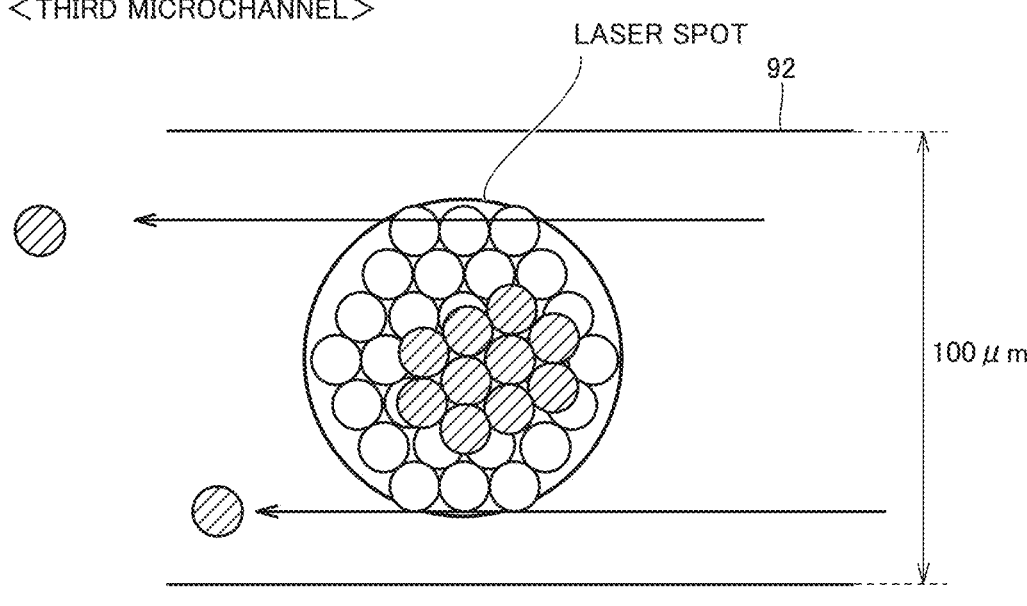
Figure 37:
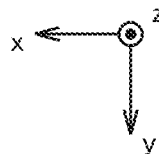
Figure 38:
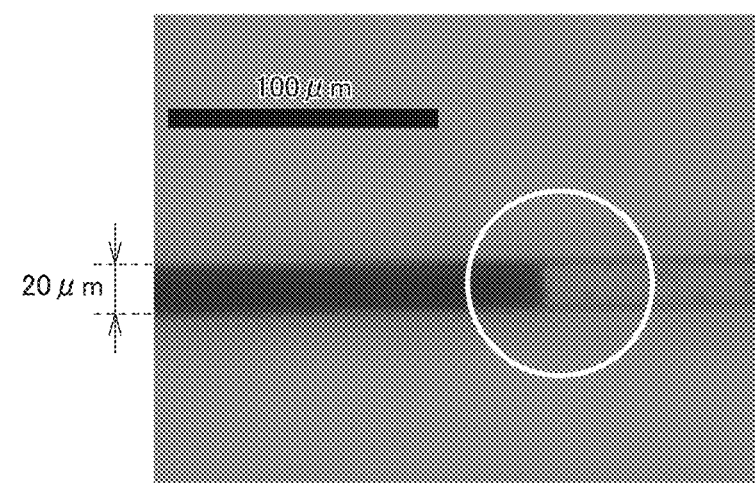
FIG. 38 is a view illustrating an image obtained by capturing a state in which the latex bead is blocked when the channel width is narrower than that of the second microchannel.
Figure 38:
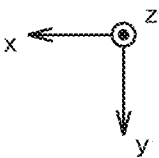

FIG. 37 is a view illustrating a difference in a mechanism between the second microchannel and the third microchannel. In the second microchannel, the entire section is irradiated with laser beam L1. Then, beads B1, B2 aggregate to form a multilayer structure of beads B1, B2. Originally, as described with reference to FIG. 31, the washing effect is generated in the distribution direction of sample SP, and beads B1, B2 that are not bound through analyte X are swept away in the distribution direction of sample SP. However, in the second microchannel, the flow of sample SP is easily blocked by beads B1, B2, and the washing effect is hardly obtained. That is, beads B1, B2 that are not bound through analyte X also remain easily without being swept away in the distribution direction of sample SP. Then, because the region where the multilayer structure is formed and the region where beads B1, B2 bound through analyte X exist are not necessarily matched with each other, the target concentration is hardly quantified with high accuracy from the multilayer ratio. FIG. 38 illustrates an image obtained by capturing the state in which beads B1, B2 are blocked when channel width W is narrower (W=20 μm) than the second microchannel.

On the other hand, in the third microchannel, the region that is not irradiated with laser beam L1 locally exists near a channel side surface. This region functions as what is called an "escape" or a "loophole" of the flow of sample SP. Accordingly, in the third microchannel, blocking by beads B1, B2 hardly occurs, and the washing effect is easy to obtain. As a result, the region where the multilayer structure is formed and the region where beads B1, B2 bound through analyte X exist are well matched with each other. Consequently, the target concentration can be quantified with high accuracy from the multilayer ratio.

Figure 39:
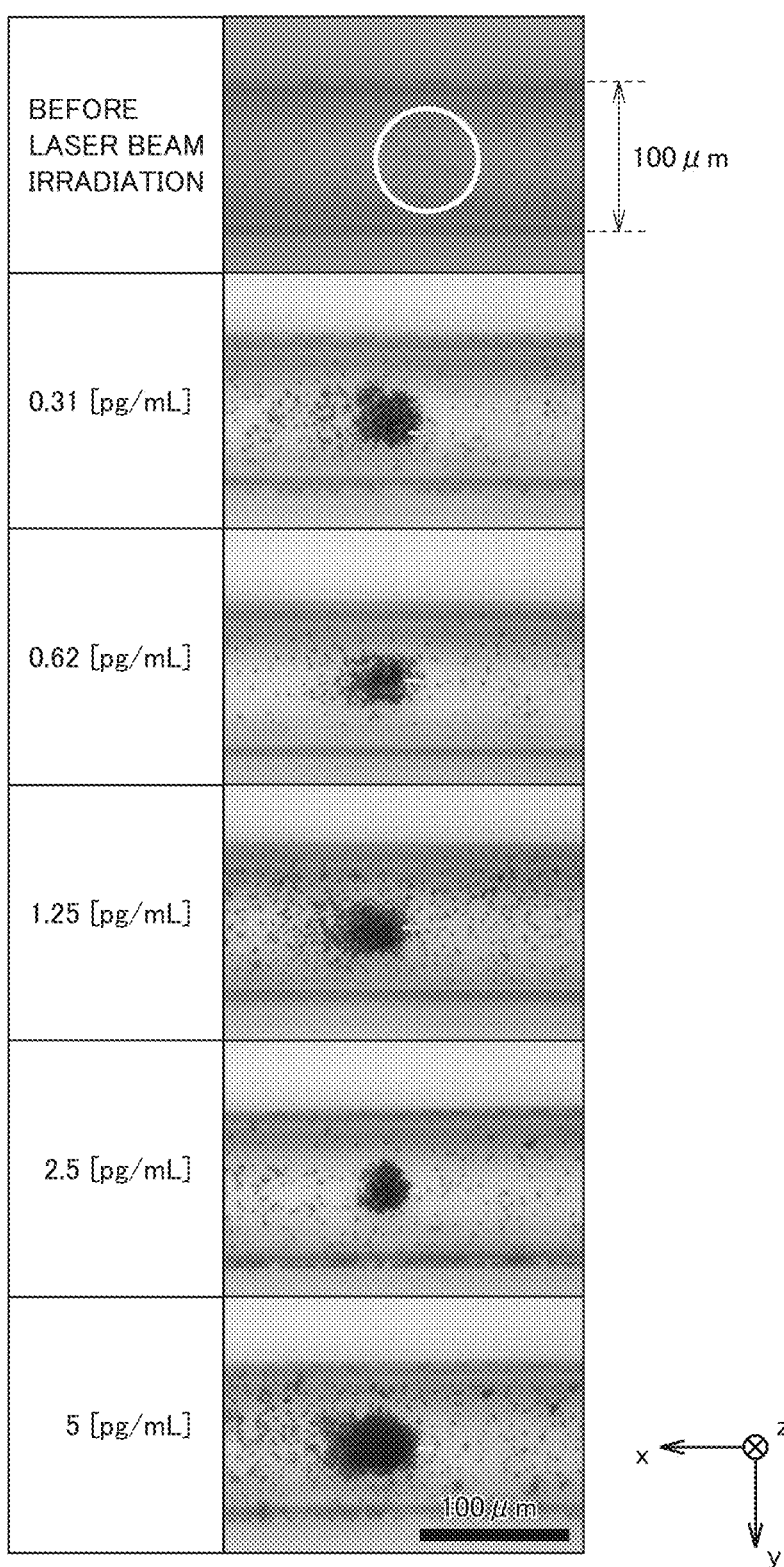
FIG. 39 is a view illustrating an image of the aggregates generated on the bottom surface of the third microchannel.

FIG. 39 is a view illustrating an image of the aggregates generated on the bottom surface of the third microchannel. In this measurement, the beam waist was adjusted downward by 65 μm from the bottom surface of microchannel 92 ($D_{btm}$=−65 μm). The laser output after the transmission through the 40-power magnifying lens was 0.27 W. In this case, the dissipative force on the channel wall surface of the third microchannel is calculated to be 3.37 pN. The CD9/CD63 complex epitope was used as analyte X. Flow velocity V of sample SP was set to 119 [μm/s].

When FIG. 39 is observed well, it can be confirmed that the deep color region increases in the contour of the aggregates of beads B1, B2 as the target concentration increases.

Figure 40:
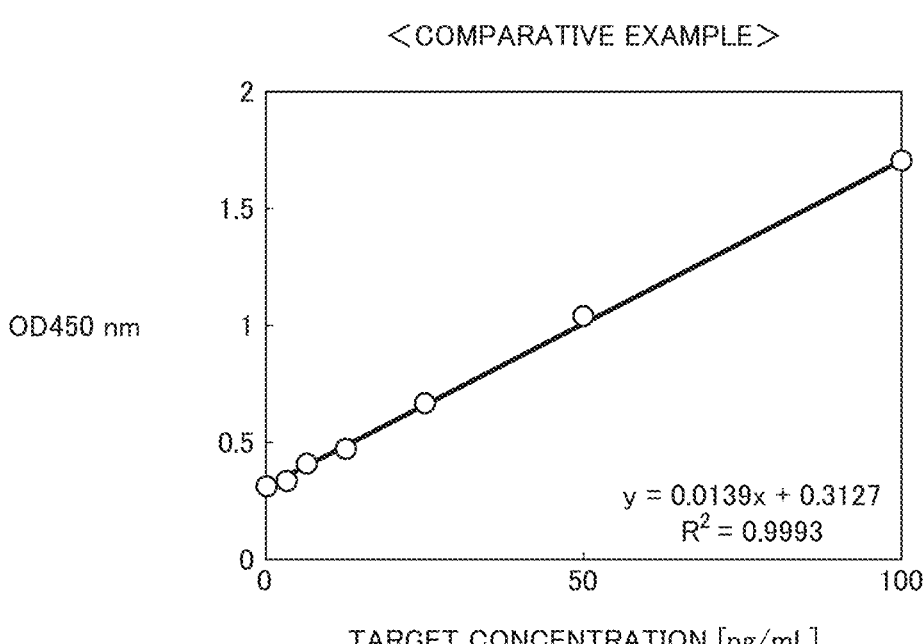
FIG. 40 is a view illustrating the calibration curve obtained by an ELISA method as a comparative example.
Figure 41:
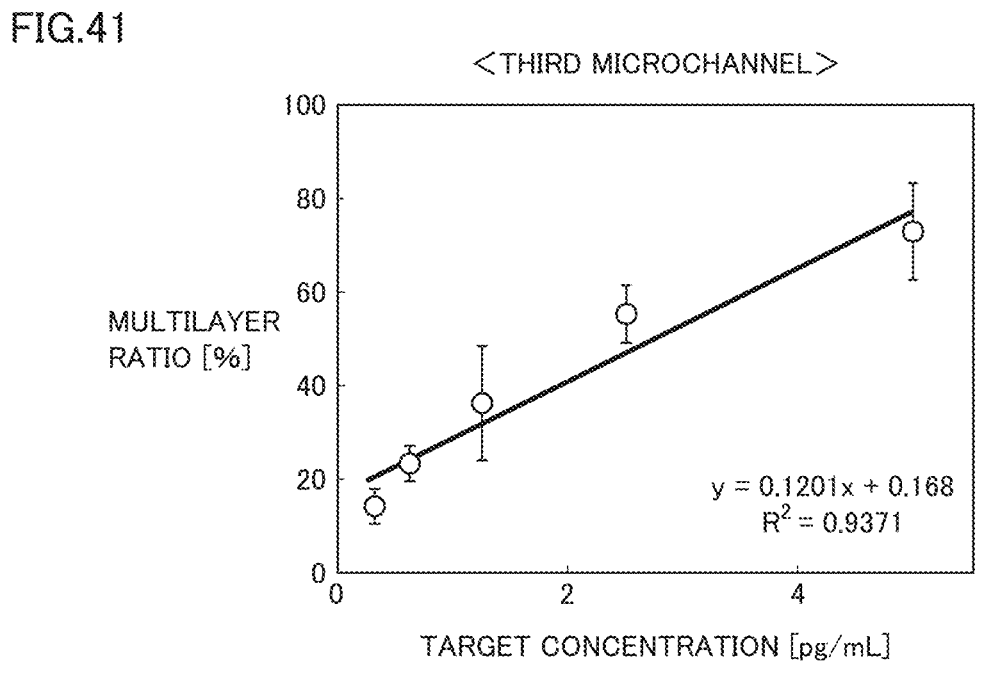

FIG. 40 is a view illustrating the calibration curve obtained by the ELISA method as a comparative example. Similarly to FIG. 39, the CD9/CD63 complex epitope was used as analyte X. The vertical axis in FIG. 40 (and FIG. 42 described later) represents the optical density (OD value) at the wavelength of 450 nm. FIG. 41 is a view illustrating the calibration curve obtained using the third microchannel.

As illustrated in FIG. 40, the calibration curve illustrating the high linear curve could also be obtained by the ELISA method (determination coefficient $R^2$=0.9993). However, the range of the target concentration measurable by the ELISA method was 3.1 [pg/mL] to 200 [pg/mL]. When the target concentration was lower than the lower limit value of the concentration range, the error bar was large, and sufficiently high quantitative accuracy could not be obtained. The sample volume was 100 μL. The measurement including pretreatment such as sample preparation required about 5 hours.

On the other hand, in Example 9, as illustrated in FIG. 41, when the CD9/CD63 complex epitope is used as analyte X, the calibration curve illustrating a high linear curve could be obtained in the concentration range of 0.31 [pg/mL] to 5.0 [pg/mL], namely, at the concentration equivalent to the lower limit of the concentration range to which the ELISA method can be applied or lower one order of magnitude ($R^2$=0.9371). The sample amount may be less than or equal to 1 μL, and the time required for the measurement was within five minutes.

The measurement result using the exosome derived from the lung cancer cell (specifically, commercially available lung cancer cell line A549) as analyte X will be described below. The measurement condition of the optical system is common to the condition described in FIG. 39. An exosome stock solution having the concentration of 1000 [μg/mL] was diluted with a phosphate buffer (mixed aqueous solution of sodium dihydrogen phosphate and disodium hydrogen phosphate) to obtain sample SP. The concentration of the phosphate buffer was 10 [mM] and the pH of the phosphate buffer was 7.0. First, the measurement results in the ELISA method will be described.

Figure 42:
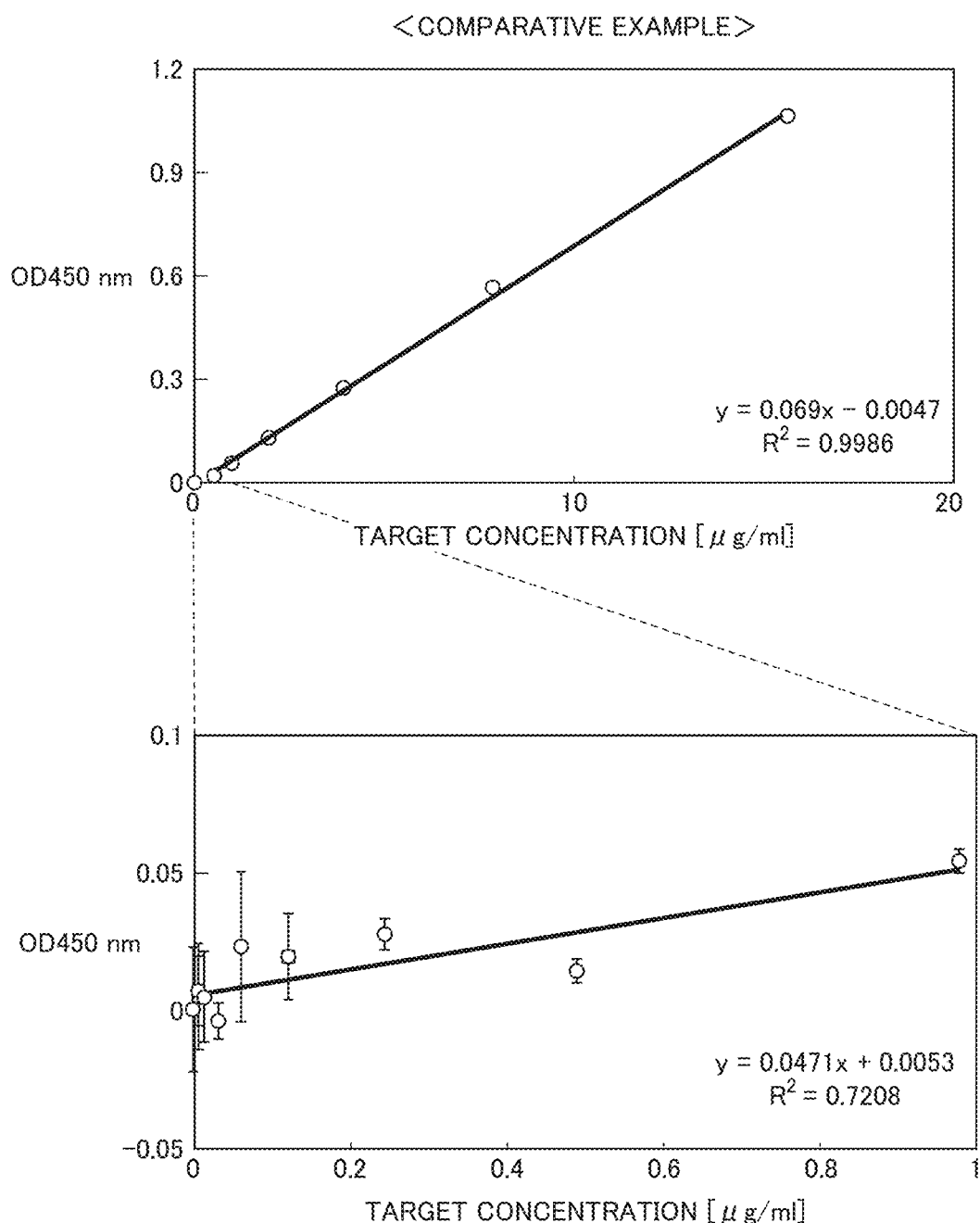
FIG. 42 is a view illustrating the calibration curve obtained by the ELISA method as the comparative example when the analyte is an exosome.

FIG. 42 is a view illustrating the calibration curve obtained by the ELISA method as the comparative example when analyte X is the exosome. According to the ELISA method, when the target concentration was within the concentration range of 1.0 [μg/mL] to 50 [μg/mL], the calibration curve illustrating the high linear curve was obtained ($R^2$=0.9986) (see the upper view). However, when the target concentration was less than or equal to 1.0 [μg/mL], the quantitative accuracy was significantly degraded ($R^2$=0.7208) (see the lower view). It took five hours to perform the measurement.

Figure 43:
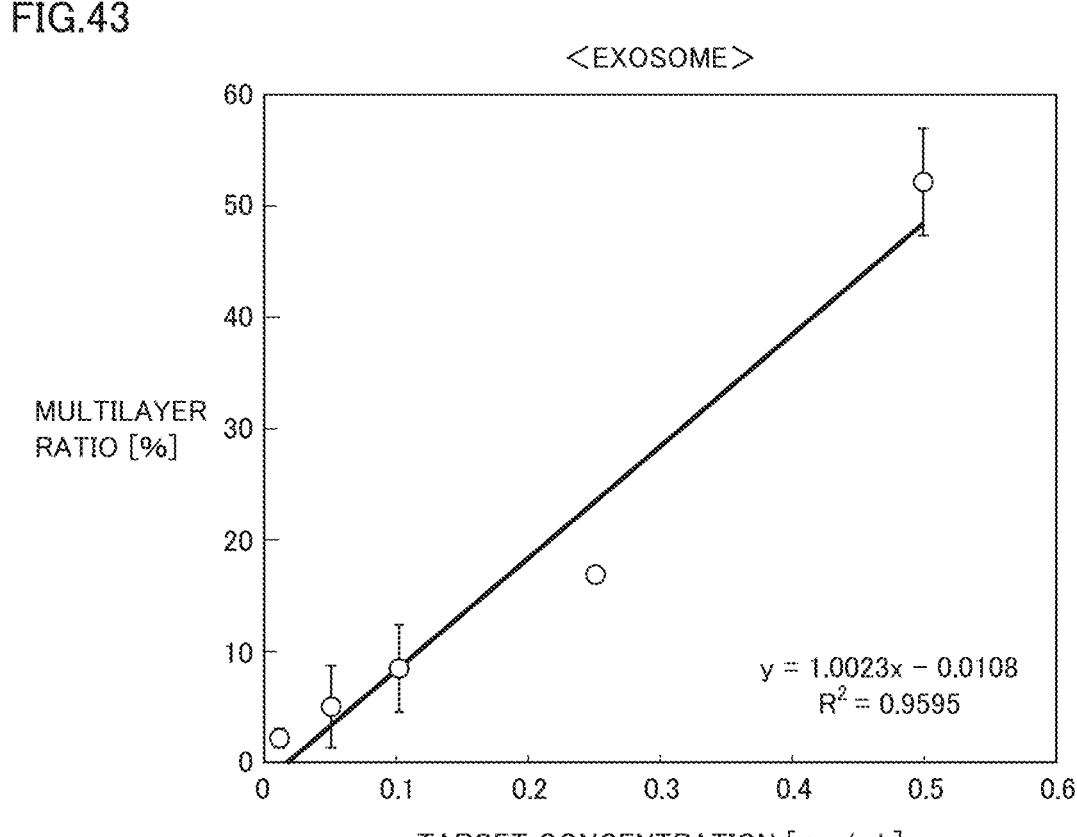
FIG. 43 is a view illustrating the calibration curve obtained when the analyte is the exosome in Example 9.

FIG. 43 is a view illustrating the calibration curve obtained when analyte X is the exosome in Example 9. In Example 9, the calibration curve illustrating the high linear curve could be obtained in the concentration range of 0.01 [μg/mL] to 0.5 [μg/mL], namely, even at the concentration that is at least two orders lower than the lower limit of the concentration range to which the ELISA method can be applied ($R^2$=0.9595). The time required for the measurement was also about five minutes, and the two-order time reduction could be achieved.

As described in FIG. 2, the exosome is the spherical material that has the membrane protein on the surface of the exosome and has the diameter of about 30 nm to about 150 nm. On the other hand, a new coronavirus (SARS-CoV-2) is also a spherical material that has S (spike) protein on the surface of the new coronavirus and has the diameter of about 100 nm. Accordingly, the measurement result in FIG. 43 illustrating that the exome can be detected with high sensitivity and quickly suggests that SARS-CoV-2 can also be detected. That is, it is suggested that Example 9 can be applied to a test for the novel coronavirus infection (COVID-19).

Example 10

<Influence of Syringe Pump>

In Example 10, measurement results using two different types of syringe pumps 30 are compared. Flow velocities V of the first and second syringe pumps were adjusted so as to be equal to each other in the calculation based on the specification values of the respective syringe pumps. Specifically, when the width x height of the section of the microchannel was 100 μm×100 μm, flow velocity V was adjusted to 167 [μm/s].

The measurement conditions other than syringe pump 30 are the same as the conditions described in FIGS. 39, 41, and 43. The exosome derived from a colorectal cancer cell (specifically, a commercially available colorectal cancer cell line HCT116) was used as analyte X. The exosome stock solution having the concentration of 1000 μg/mL was diluted with the phosphate buffer to obtain sample SP. The concentration of the phosphate buffer was 10 [mM] and the pH of the phosphate buffer was 7.0.

Figure 44:
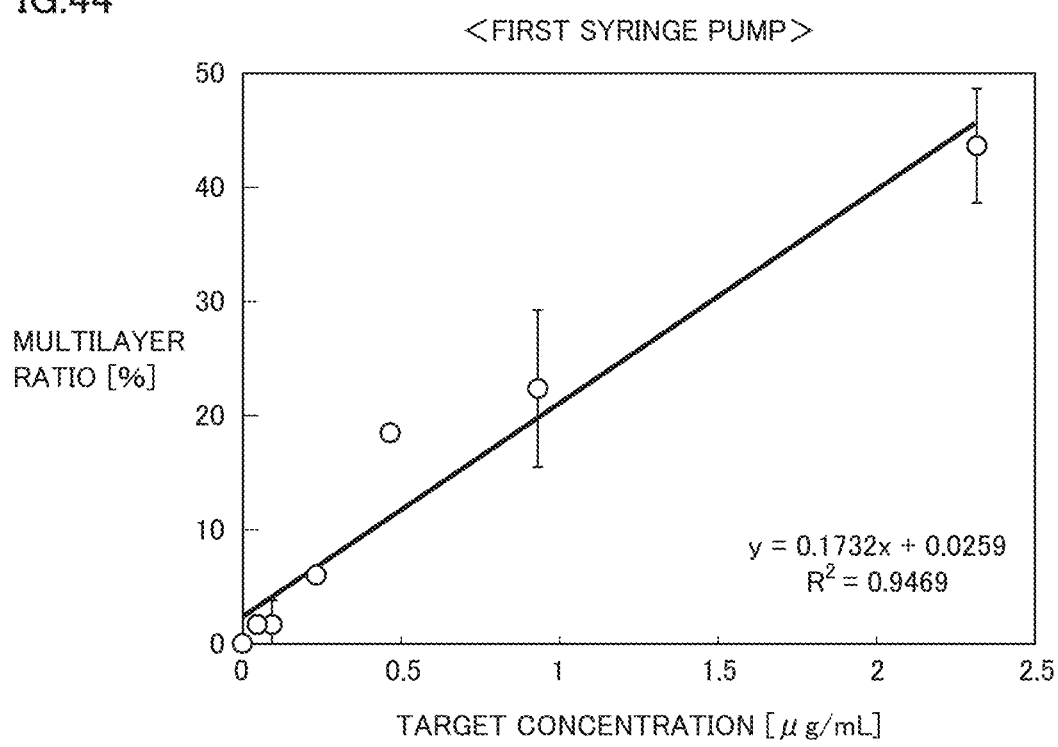
FIG. 44 is a view illustrating calibration curves obtained using two types of syringe pumps.
Figure 44:
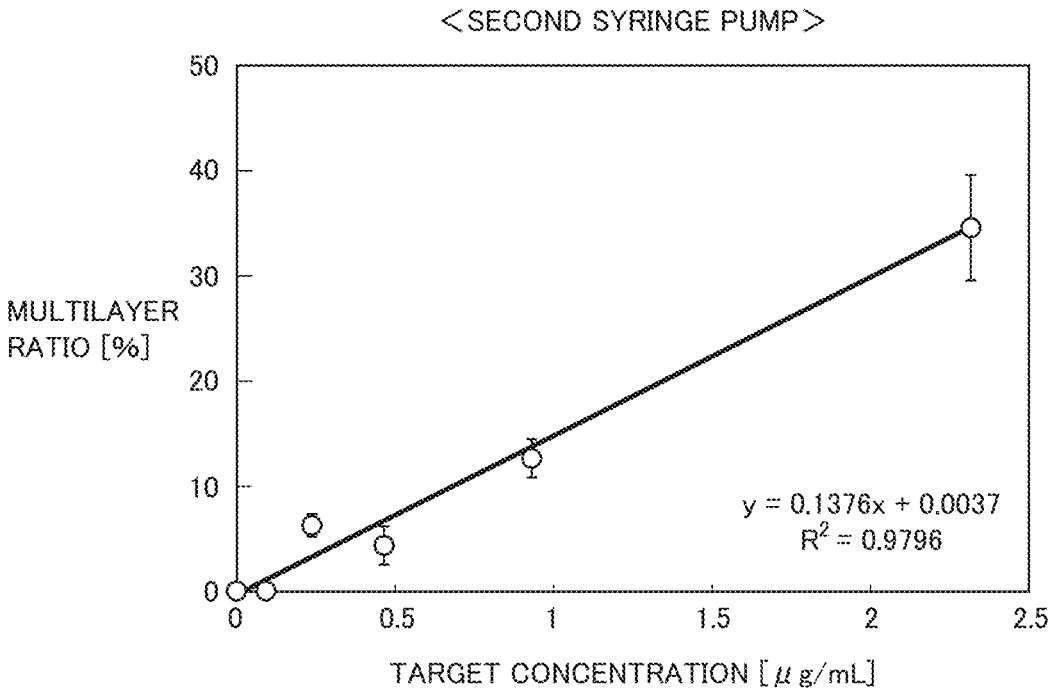

FIG. 44 is a view illustrating calibration curves obtained using two types of syringe pumps. The calibration curve obtained using the first syringe pump is illustrated in the upper part of FIG. 44, and the calibration curve obtained using the second syringe pump is illustrated in the lower part of FIG. 44. It has been confirmed that the flow velocity of the second syringe pump is more stable than that of the first syringe pump.

It was confirmed that the calibration curve illustrating the high linearity with respect to the exosome derived from the colorectal cancer cell can be obtained when either the first or second syringe pumps is used. However, particularly when compared in the low concentration range less than 1 [μg/mL], it can be read that the linearity of the calibration curve is further improved while the measurement error is reduced in the case of using the second syringe pump capable of generating a more stable flow velocity as compared with the case of using the first syringe pump. As described in Example 2 (see FIG. 16), flow velocity V of sample SP is desirably adjusted to an optimum flow velocity at which the growth of the aggregates of beads B1, B2 and analyte X easily proceeds. The more ideal calibration curve can be produced by selecting syringe pump 30 capable of generating a stable pressure driven flow suitable for implementing the optimum flow velocity.

As described above, in the first embodiment, sample SP that contains analyte X (the CD80, the exosome, and the like) and beads B1, B2 and flows through microchannel 92 is irradiated with laser beam L1 that is non-resonant light to beads B1, B2. By implementing the "light-induced acceleration" using the light-induced force of laser beam L1, in the existence of analyte X, beads B1, B2 aggregate in a short time (for example, several minutes) even when analyte X is an extremely small amount (for example, sub to several [pg/mL]). The existence of analyte X can be detected by determining the existence of the aggregates of beads B1, B2 based on the image captured by camera 60 (first antigen detection process). In particular, the target concentration can be calculated from aggregation area A by preparing previously the correspondence relationship between the area (aggregation area A) of the aggregates of beads B1, B2 and the concentration (target concentration) of analyte X as the calibration curve (second antigen detection process). Consequently, according to the first embodiment, analyte X can be detected quickly and with high sensitivity. The same applies to the combination of analyte Y (the FDP or the like) and bead B3.

Second Embodiment

In a second embodiment, a configuration in which the light-induced acceleration is applied to three-dimensional fluorescence observation will be described.

Figure 45:
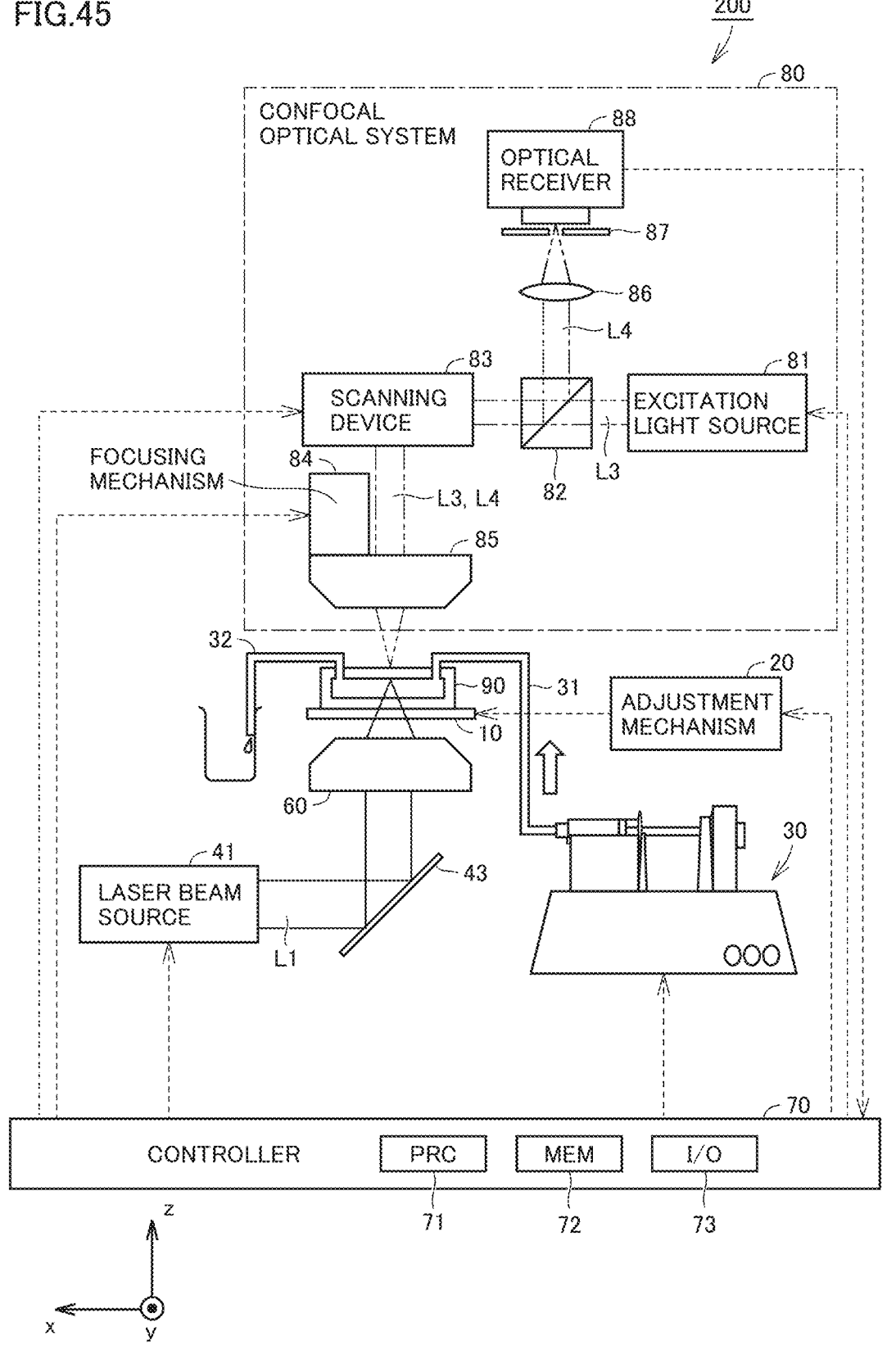
FIG. 45 is a schematic diagram illustrating an overall configuration of an antigen detection system according to a second embodiment.

FIG. 45 is a schematic diagram illustrating an overall configuration of an antigen detection system of the second embodiment. An antigen detection system 200 of the second embodiment is different from the antigen detection system 100 of the first embodiment (see FIG. 4) in including a confocal optical system 80 that is an optical system of a confocal laser microscope. Confocal optical system 80 includes an excitation light source 81, a beam splitter 82, a scanning device 83, a focusing mechanism 84, an objective lens 85, an imaging lens 86, a pinhole (confocal diaphragm) 87, and an optical receiver 88.

Excitation light source 81 emits a laser beam L3 to observe sample SP. Laser beam L3 has a wavelength capable of exciting a fluorescent dye included in sample SP. Hereinafter, the fluorescence to be observed emitted from sample SP is also referred to as "fluorescence L4".

Beam splitter 82 is configured to transmit laser beam L3 from excitation light source 81 and reflect fluorescence L4 from sample SP.

In response to the command from controller 70, scanning device 83 scans laser beam L3 from excitation light source 81 in the direction (xy-direction) orthogonal to the optical axis. For example, a galvano mirror, a polygon mirror, or an acousto-optic deflector (AOD) can be used as scanning device 83.

Focusing mechanism 84 changes the distance in the optical axis direction (z-direction) between detection kit 90 and the focal position of objective lens 85 in response to the command from controller 70. Although FIG. 45 illustrates an example in which focusing mechanism 84 moves objective lens 85, focusing mechanism 84 may move XYZ-axis stage 10 on which detection kit 90 is disposed in the optical axis direction. That is, it is sufficient that focusing mechanism 84 can change the relative positional relationship between detection kit 90 and objective lens 85 in the optical axis direction. In addition, a spatial light modulator (SLM), a deformable mirror, or the like may be adopted instead of focusing mechanism 84.

Objective lens 85 irradiates sample SP with laser beam L3 from excitation light source 81, and transmits fluorescence L4 emitted from sample SP toward scanning device 83.

Imaging lens 86 condenses fluorescence L4 reflected by beam splitter 82 on pinhole 87.

Pinhole 87 is disposed at a position conjugate with the focal position of objective lens 85 between imaging lens 86 and optical receiver 88.

Optical receiver 88 detects fluorescence L4 passing through pinhole 87 and outputs the detection result to controller 70. Optical receiver 88 includes a light receiving element such as a photodiode, an avalanche photodiode (APD), or a photomultiplier tube.

The configuration of antigen detection system 200 other than the above is common to the corresponding configuration of antigen detection system 100. Accordingly, the detailed description will not be repeated. In addition, although not illustrated in order to avoid complication of the drawings, antigen detection system 200 is also configured to capture the optical microscope image as illustrated in the measurement results below.

Figure 46:
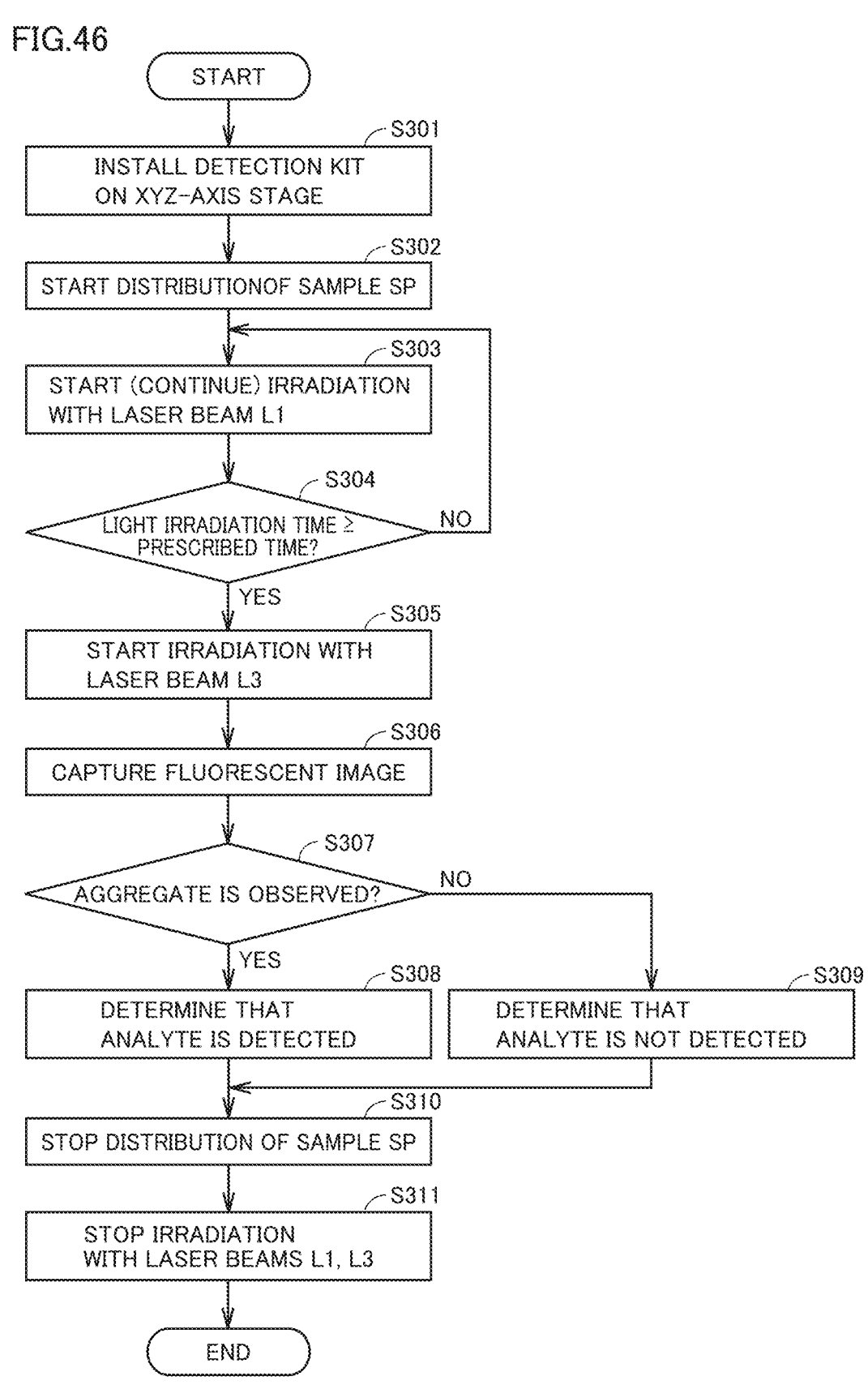
FIG. 46 is a flowchart illustrating first antigen detection process in the second embodiment.
Figure 47:
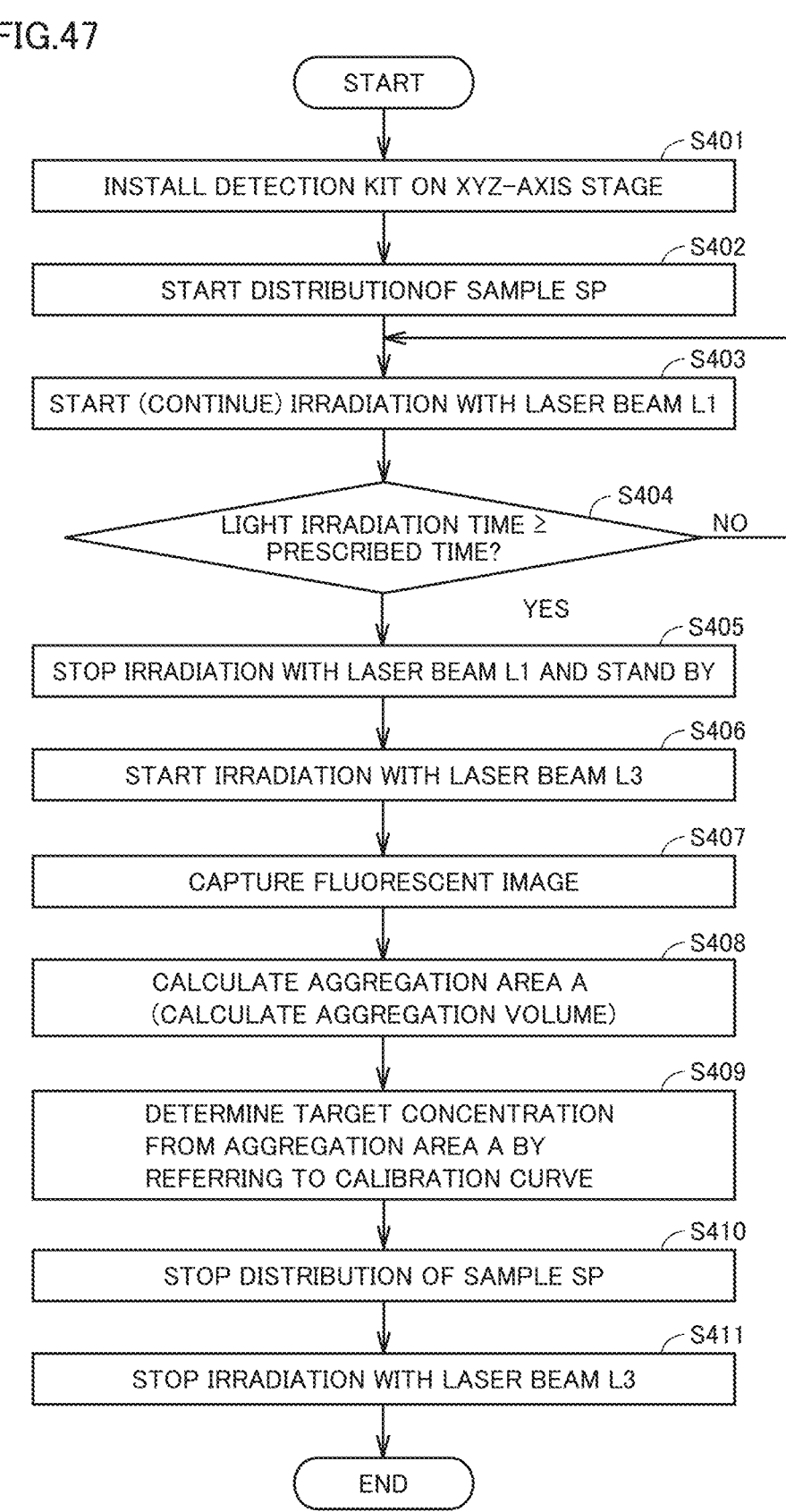
FIG. 47 is a flowchart illustrating second antigen detection process in the second embodiment.

FIG. 46 is a flowchart illustrating first antigen detection process in the second embodiment. FIG. 47 is a flowchart illustrating second antigen detection process in the second embodiment. Referring to FIGS. 46 and 47, the first or second antigen detection process in the second embodiment is different from the process in the first embodiment (see FIG. 12 or 13) in including process of emitting laser beam L3 (S305, S406) instead of process of emitting white light L2 (S105, S206), and including process of capturing a fluorescent image (S306, S407) instead of process of capturing the image (optical microscopic image) (S106, S207). Because process other than these is equivalent, the description will not be repeated.

Example 11

In Example 11, the CD9/CD63 complex epitope was used as analyte X. Because the CD9/CD63 complex epitope does not contain a fluorescent dye, a fluorescent bead was adopted for beads B1, B2 (bead body B0).

Figure 48:
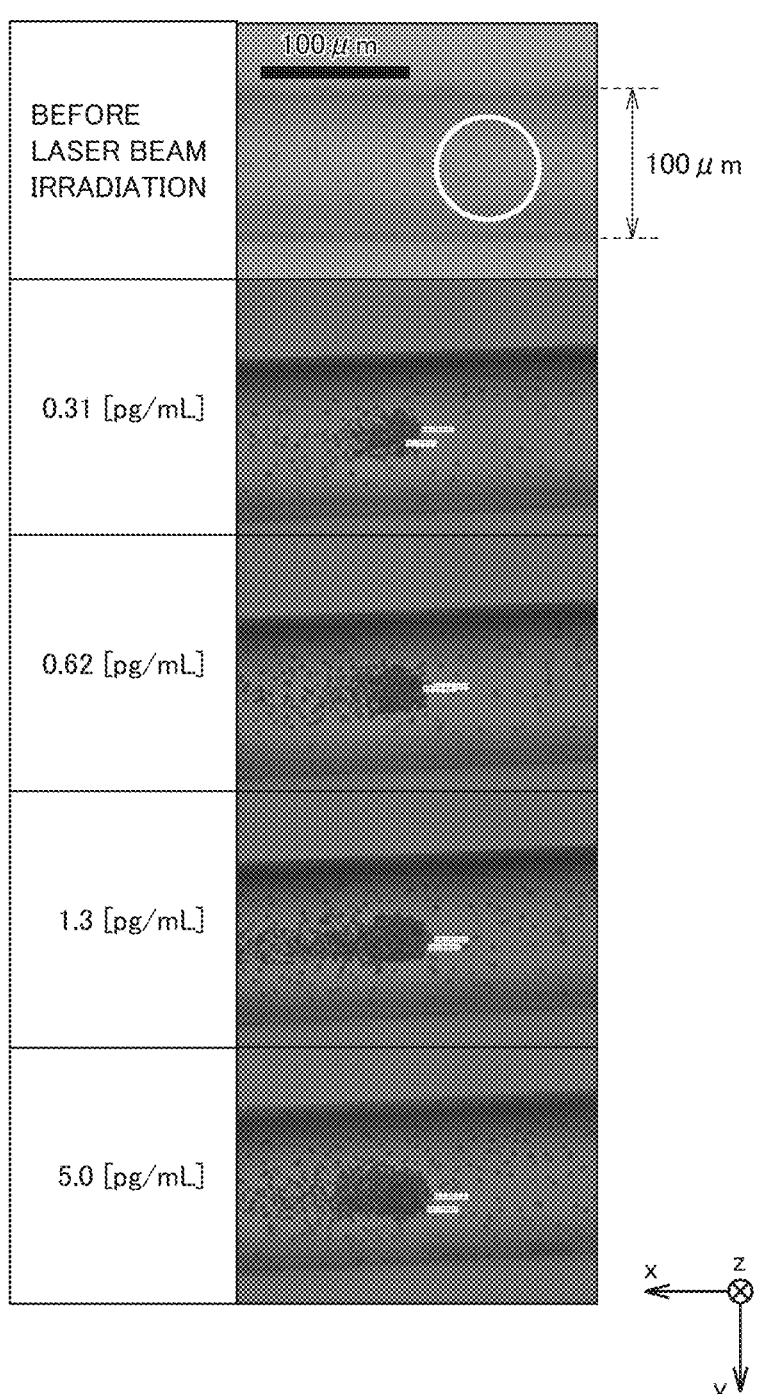
FIG. 48 is a view illustrating an optical microscope image of the aggregate formed in the microchannel when the analyte is the CD9/CD63 complex epitope and when the bead is a fluorescent bead.
Figure 49:
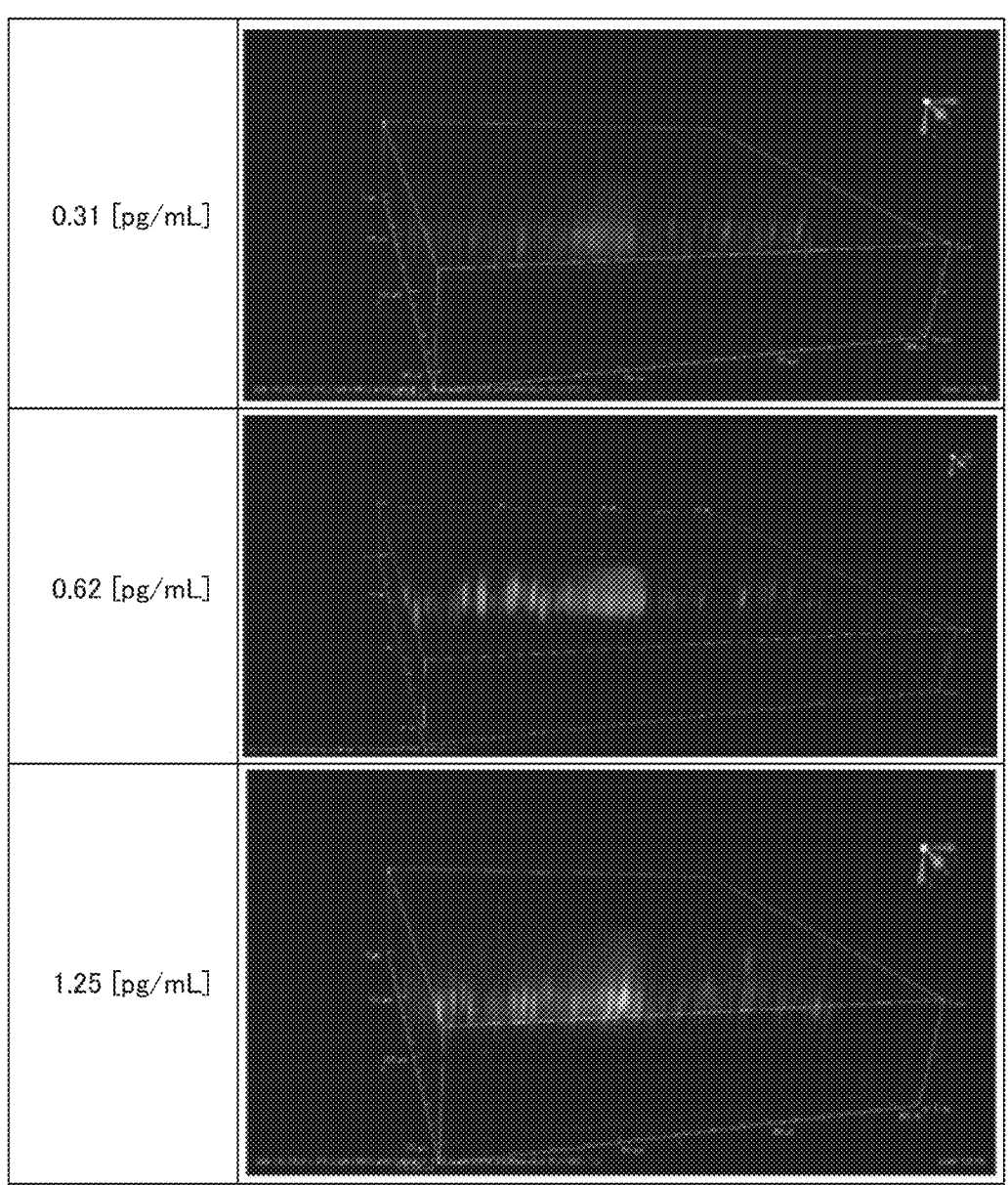
FIG. 49 is a view illustrating a three-dimensional fluorescence image of the aggregate formed in the microchannel when the analyte is the CD9/CD63 complex epitope and when the bead is the fluorescent bead.

FIG. 48 is a view illustrating an optical microscope image of the aggregate formed in microchannel 92 when the fluorescent bead is used. FIG. 49 is a view illustrating a three-dimensional fluorescence image of the aggregate formed in microchannel 92 when the fluorescent bead is used.

From the optical microscope image in FIG. 48, it was confirmed that aggregation area A of beads B1, B2 increased as the target concentration increased. Also in the three-dimensional fluorescence image of FIG. 49, it was observed that the state in which the region (volume) indicating higher fluorescence intensity spread as the target concentration increased.

The volume of the region indicating the high fluorescence intensity, so to speak, the aggregation volume of beads B1, B2 may be used instead of aggregation area A of beads B1, B2. The calibration curve between the aggregation volume and the target concentration is prepared, so that the target concentration can be calculated from the aggregation volume. The aggregate volume is another example of the "index representing the size of the aggregate" according to the present disclosure. Confocal optical system 80 is not essential for calculating the aggregation volume. The aggregation volume can also be calculated by observing the aggregate from at least two directions (for example, the vertical direction and the horizontal direction) using an optical system of a general optical microscope.

Furthermore, an elongated aggregate extending in the distribution direction of sample SP can be formed using a cylindrical lens instead of a convex lens as objective lens 50. In this case, the length of the region where beads B1, B2 are aggregated (the length in the distribution direction of sample SP) can also be used as the "index representing the size of the aggregate". As described above, the "index representing the size of the aggregate" may be any of the length (one-dimensional parameter), the area (two-dimensional parameter), and the volume (three-dimensional parameter).

Example 12

In Example 12, a non-fluorescent exosome derived from a lung cancer cell line A549 was used as analyte X. The protein concentration (target concentration) of the non-fluorescent exosome was set to two ways of 0.1 [μg/mL] and 1 [μg/mL]. The concentration of the phosphate buffer was 10 [mM] and the pH of the phosphate buffer was 7.0. Fluorescent beads were used as beads B1, B2.

Figure 50:
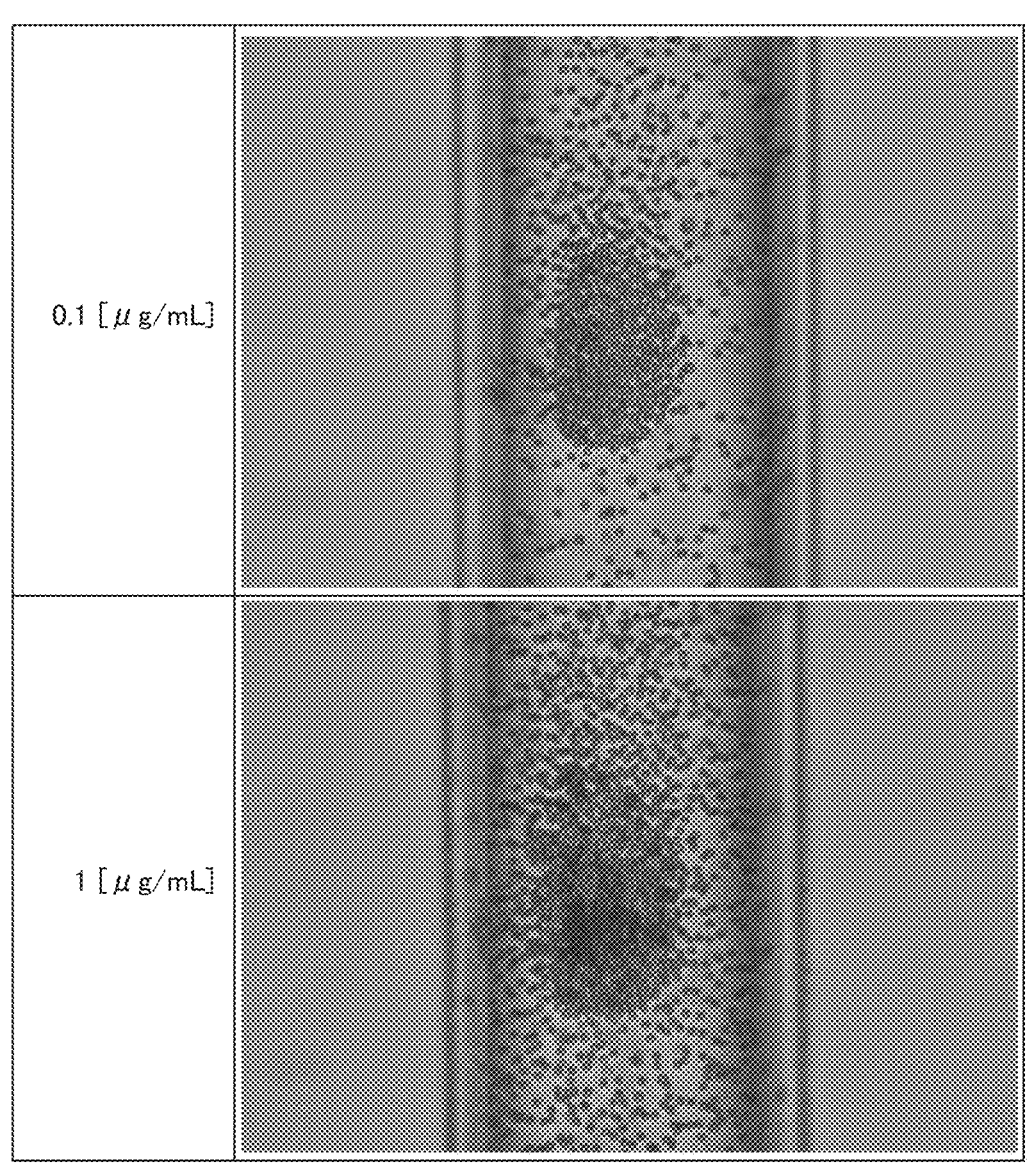
FIG. 50 is a view illustrating an optical microscope image of the aggregate formed in the microchannel when the analyte is a non-fluorescent exosome and when the bead is the fluorescent bead.
Figure 51:
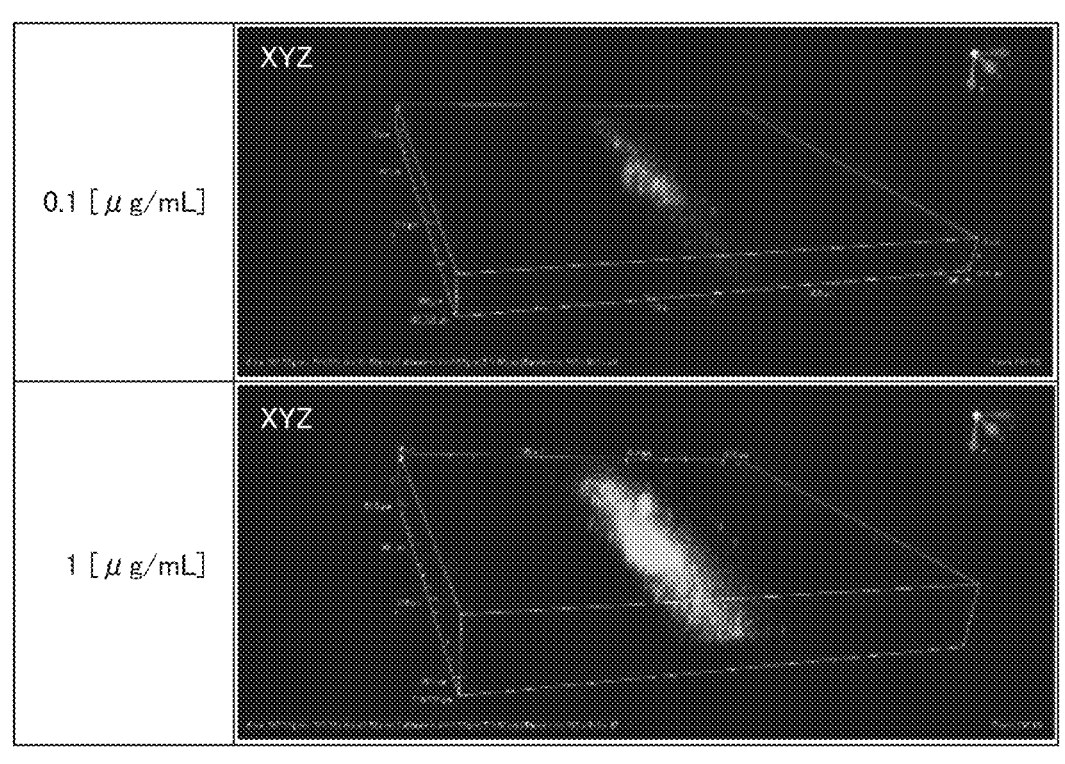
FIG. 51 is a view illustrating a three-dimensional fluorescence image of the aggregate formed in the microchannel when the analyte is the non-fluorescent exosome and when the bead is the fluorescent bead.

FIG. 50 is a view illustrating an optical microscope image of the aggregate formed in microchannel 92 when analyte X is the non-fluorescent exosome and when the beads B1, B2 are the fluorescent bead. FIG. 51 is a view illustrating a three-dimensional fluorescence image of the aggregate formed in microchannel 92 when analyte X is the non-fluorescent exosome and when the beads B1, B2 are the fluorescent bead.

Similarly to Example 11, in the optical microscope image (FIG. 50), aggregation area A of beads B1, B2 increased as the target concentration increased. Also in the three-dimensional fluorescence image (FIG. 51), the volume of the region having the high fluorescence intensity increased as the target concentration increased.

Example 13

In Example 13, a fluorescent exosome (CD63-GFP-HeLa-exosome) was used as analyte X. The protein concentration (target concentration) of the fluorescent exosome was 20 [μg/mL]. The concentration of the phosphate buffer was 10 [mM] and the pH of the phosphate buffer was 7.0. The non-fluorescent beads were used as beads B1, B2.

Figure 52:
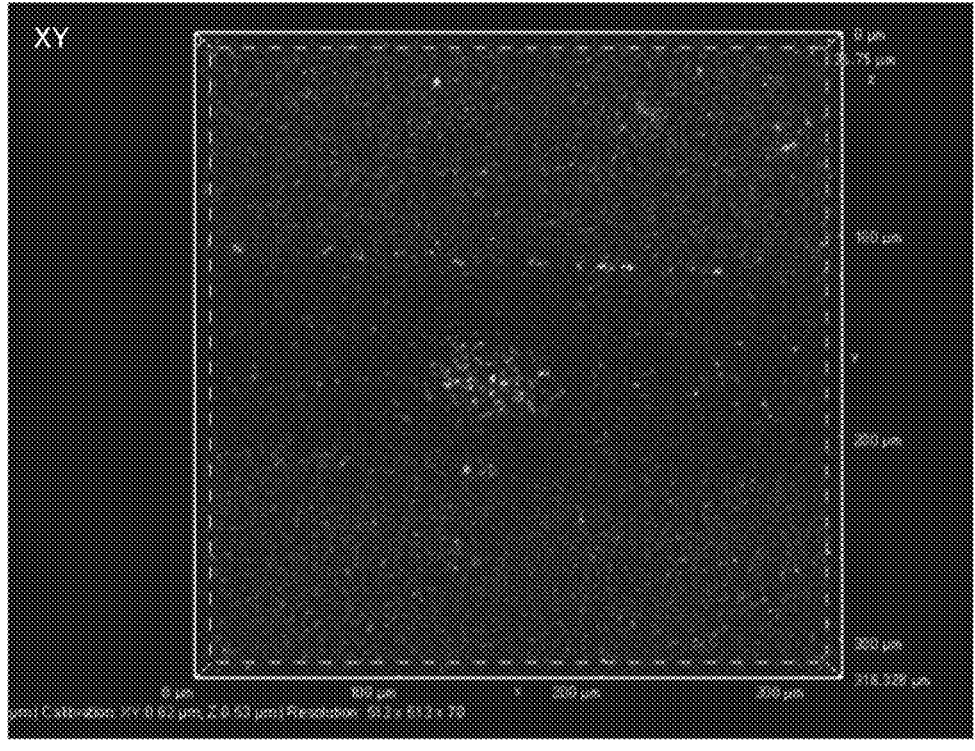
FIG. 52 is a view illustrating a two-dimensional fluorescence image of the aggregate formed in the microchannel when the analyte is a fluorescent exosome and when the bead is a non-fluorescent bead.

FIG. 52 is a view illustrating a two-dimensional fluorescence image of the aggregate formed in microchannel 92 when analyte X is the fluorescent exosome. With reference to FIG. 52, even when beads B1, B2 were the non-fluorescent beads, the fluorescence from the fluorescent exosome specifically bound to beads B1, B2 could be confirmed.

In Examples 11 to 13, the example in which only one of analyte X and beads B1, B2 contains the fluorescent dye has been described. However, also when both analyte X and beads B1, B2 contain the fluorescent dye, it is apparent from the above measurement results that the size of the region indicating the high fluorescence intensity (≈aggregation area A) is determined according to the target concentration.

As described above, in the second embodiment, at least one of analyte X and beads B1, B2 contains the fluorescent dye, and the antigen detection system 200 includes confocal optical system 80 capable of observing the fluorescence. The existence of analyte X can be detected by determining the existence of the aggregates of beads B1, B2 based on whether the region indicating the fluorescence is observed in the two-dimensionally or three-dimensionally captured fluorescence image (first antigen detection process). In addition, the target concentration can be calculated from aggregation area A by preparing previously the correspondence relationship between the size of the region where the fluorescence is observed (that is, aggregation area A) and the target concentration as the calibration curve (second antigen detection process). Accordingly, in the second embodiment, similarly to the first embodiment, analyte X can be detected quickly and with high sensitivity. The same applies to the combination of analyte Y and bead B3.

The first embodiment and the second embodiment can be appropriately combined. Fluorescence observation can be performed in consideration of the upward irradiation and the downward irradiation, the defocus condition, the relationship between channel width W and irradiation spot diameter φ, the flow velocity adjustment, and the like described in the first embodiment.

It should be considered that the disclosed embodiments are an example in all respects and not restrictive. The scope of the present disclosure is defined by not the description of the embodiments, but the claims, and it is intended that all changes within the meaning and scope of the claims are included in the present invention.

The invention claimed is:

1. A method for increasing a sensitivity of detection of an analyte, the method comprising:
    pumping, by using a pump, a flow of a liquid sample through a microchannel, the flow of the liquid sample containing a plurality of fine particles each of which is modified with a host molecule that specifically binds to the analyte, the microchannel including an upper surface and a bottom surface, and the microchannel being filled with the flow of the liquid sample;
    irradiating the liquid sample flowing through the microchannel with non-resonant light outside a wavelength range of electronic resonance of the plurality of fine particles such that an aggregate of the analyte and the plurality of the fine particles is formed, the irradiating including:
        irradiating the liquid sample with the non-resonant light under a condition that a focal point of the non-resonant light is located further behind the upper surface or the bottom surface of the microchannel, the focal point located behind the microchannel in an irradiation direction of the non-resonant light; and
        applying a force induced by the non-resonant light in a same direction as the irradiation direction to press the plurality of fine particles against the upper surface or the bottom surface behind which the focal point is located;
    capturing, via an optical receiver that receives light from the liquid sample, an image of the liquid sample;

image-processing the image of the liquid sample, thereby determining a size of an aggregate formed by aggregation of the analyte and the plurality of fine particles contained within the liquid sample; and
    detecting a concentration of the analyte contained in the liquid sample based on the size of the aggregate and a previously-obtained correspondence relationship between concentrations of the analyte and sizes of aggregates.

2. The method for increasing the sensitivity of detection of the analyte according to claim 1, wherein:
    the optical receiver includes a camera that captures the image of the liquid sample;
    the image-processing includes calculating, based on the image, an index representing the size of the aggregate; and
    the detecting includes calculating, by referring to the previously-obtained correspondence relationship, the concentration of the analyte contained in the liquid sample based on the calculated index.

3. The method for increasing the sensitivity of detection of the analyte according to claim 1, further comprising stopping the irradiation with the non-resonant light after the irradiating, and wherein:
    the detecting includes detecting the concentration of the analyte based on a signal acquired from the optical receiver after standby for a period of time required to wash the aggregate formed within the flow of the liquid sample after the irradiation with the non-resonant light is stopped, and
    washing the aggregate includes sweeping away, from the aggregate, fine particles which are not bound to the aggregate in a flow direction of the liquid sample.

4. The method for increasing the sensitivity of detection of the analyte according to claim 1, wherein the detecting includes determining whether the analyte is contained in the liquid sample based on a change in intensity of a signal acquired from the optical receiver while the irradiating with the non-resonant light is continued.

5. The method for increasing the sensitivity of detection of the analyte according to claim 1, wherein:
    specific gravity of each of the plurality of fine particles is larger than specific gravity of a dispersion medium of the plurality of fine particles, and
    the irradiating includes irradiating the liquid sample with the non-resonant light from above to below of the liquid sample.

6. The method for increasing the sensitivity of detection of the analyte according to claim 1, wherein the irradiating includes irradiating the liquid sample with the non-resonant light so that a region of the microchannel through which the liquid sample flows is not irradiated with the non-resonant light.

7. The method for increasing the sensitivity of detection of the analyte according to claim 1, further comprising, prior to the irradiating, adjusting a flow velocity of the liquid sample to a flow velocity at which the analyte and the plurality of fine particles can be prevented from splitting after aggregation.

8. The method for increasing the sensitivity of detection of the analyte according to claim 1, wherein at least one of the analyte or the plurality of fine particles is modified with a fluorescent dye.

9. The method for increasing the sensitivity of detection of the analyte according to claim 1, wherein a combination of diameters of the plurality of fine particles and a wavelength range of the non-resonant light is determined such that the non-resonant light causes Mie scattering when the plurality of fine particles are irradiated with the non-resonant light.

\* \* \* \* \*